US012569509B2

(12) United States Patent
Thompson

(10) Patent No.: US 12,569,509 B2
(45) **Date of Patent: \*Mar. 10, 2026**

(54) METHOD AND COMPOSITION FOR PREVENTING AND TREATING VIRAL INFECTIONS

(71) Applicant: GLOBAL BIOLIFE INC., Bethesda, MD (US)

(72) Inventor: Daryl Thompson, Winter Haven, FL (US)

(73) Assignee: Global Biolife Inc., Bethesda, MD (US)

(\*) Notice: Subject to any disclaimer, the term of this patent is extended or adjusted under 35 U.S.C. 154(b) by 856 days.

This patent is subject to a terminal disclaimer.

(21) Appl. No.: 17/729,711

(22) Filed: Apr. 26, 2022

(65) Prior Publication Data

US 2022/0249530 A1 Aug. 11, 2022

Related U.S. Application Data

(63) Continuation-in-part of application No. 16/642,976, filed as application No. PCT/US2017/048892 on Aug. 28, 2017, now Pat. No. 11,311,563.

(51) Int. Cl.

| | |
|---|---|
| *A61K 31/7048* | (2006.01) |
| *A61K 31/192* | (2006.01) |
| *A61K 31/352* | (2006.01) |
| *A61P 31/12* | (2006.01) |

(52) U.S. Cl.
CPC ........ *A61K 31/7048* (2013.01); *A61K 31/192* (2013.01); *A61K 31/352* (2013.01); *A61P 31/12* (2018.01)

(58) Field of Classification Search
None
See application file for complete search history.

(56) References Cited

U.S. PATENT DOCUMENTS

| | | | | |
|---|---|---|---|---|
| 6,555,523 | B1 * | 4/2003 | Prendergast | ............ A61P 33/06 514/27 |
| 10,383,842 | B2 | 8/2019 | Thompson | |
| 2004/0198672 | A1 * | 10/2004 | Qazi | ...................... A61K 31/00 514/27 |

| | | | | |
|---|---|---|---|---|
| 2008/0119545 | A1 | 5/2008 | Hensley et al. | |
| 2012/0022010 | A1 * | 1/2012 | Brand | ...................... A61P 31/06 514/27 |
| 2016/0367517 | A1 | 12/2016 | Thompson | |
| 2020/0306281 | A1 | 10/2020 | Thompson | |

OTHER PUBLICATIONS

Badhani, B., Sharma, N., & Kakkar, R. (2015). Gallic acid: a versatile antioxidant with promising therapeutic and industrial applications. Rsc Advances, 5(35), 27540-27557. (Year: 2015).*

Tsai, F. J., Lin, C. W., Lai, C. C., Lan, Y. C., Lai, C. H., Hung, C. H., . . . & Lin, Y. J. (2011). Kaempferol inhibits enterovirus 71 replication and internal ribosome entry site (IRES) activity through FUBP and HNRP proteins. Food chemistry, 128(2), 312-322. (Year: 2011).*

Von Itzstein, M. (2007). The war against influenza: discovery and development of sialidase inhibitors. Nature reviews Drug discovery, 6(12), 967-974. (Year: 2007).*

Anderson, M. E., & Siahaan, T. J. (2003). Targeting ICAM-1/LFA-1 interaction for controlling autoimmune diseases: designing peptide and small molecule inhibitors. Peptides, 24(3), 487-501. (Year: 2003).*

International Search Report and Written Opinion of the International Searching Authority for PCT/US2023/065834 dated Aug. 29, 2023.

International Preliminary Report on Patentability for PCT/US2023/065834 dated Nov. 7, 2024.

Decision of Refusal in Japanese Patent Application No. 2020-511973 dated Jun. 7, 2022.

Choi, et al, "Anti-Human Rhinovirus Activity of Gallic Acid Possessing Antoxidant Capacity", 2010, vol. 24, No. 9, pp. 1292-1296, Phytotherapy Research.

Muller Kratz, et al, "Anti-HSV-1 and anti-HIV-1 activity of gallic acid and pentyl gallate", Aug. 2008, vol. 103, No. 5, pp. 437-442, Memoras do Instituto Oswaldo Cruz.

\* cited by examiner

*Primary Examiner* — Dale R Miller

(74) *Attorney, Agent, or Firm* — Stephen J. Weyer, Esq.; Stites & Harbison, PLLC

(57) ABSTRACT

A method and composition for treating viral infections using a combination of naturally occurring compounds is provided. The method includes administering to a patient at risk of or diagnosed with a viral infection a composition including therapeutically effective amounts of a helicase ATPase inhibitor, a sialidase enzyme inhibitor, an ICAM-1 inhibitor and gallic acid which each also down regulate the immune response. The composition may further include a permeation enhancer.

8 Claims, 49 Drawing Sheets

Virus Cycle

Entry
ICAM-1
VCAM-1

Replication
Helicase
ATPase

Budding
Neuraminidase

The synergistic action of Equivir/Nemovir blocks multiple viral mechanisms

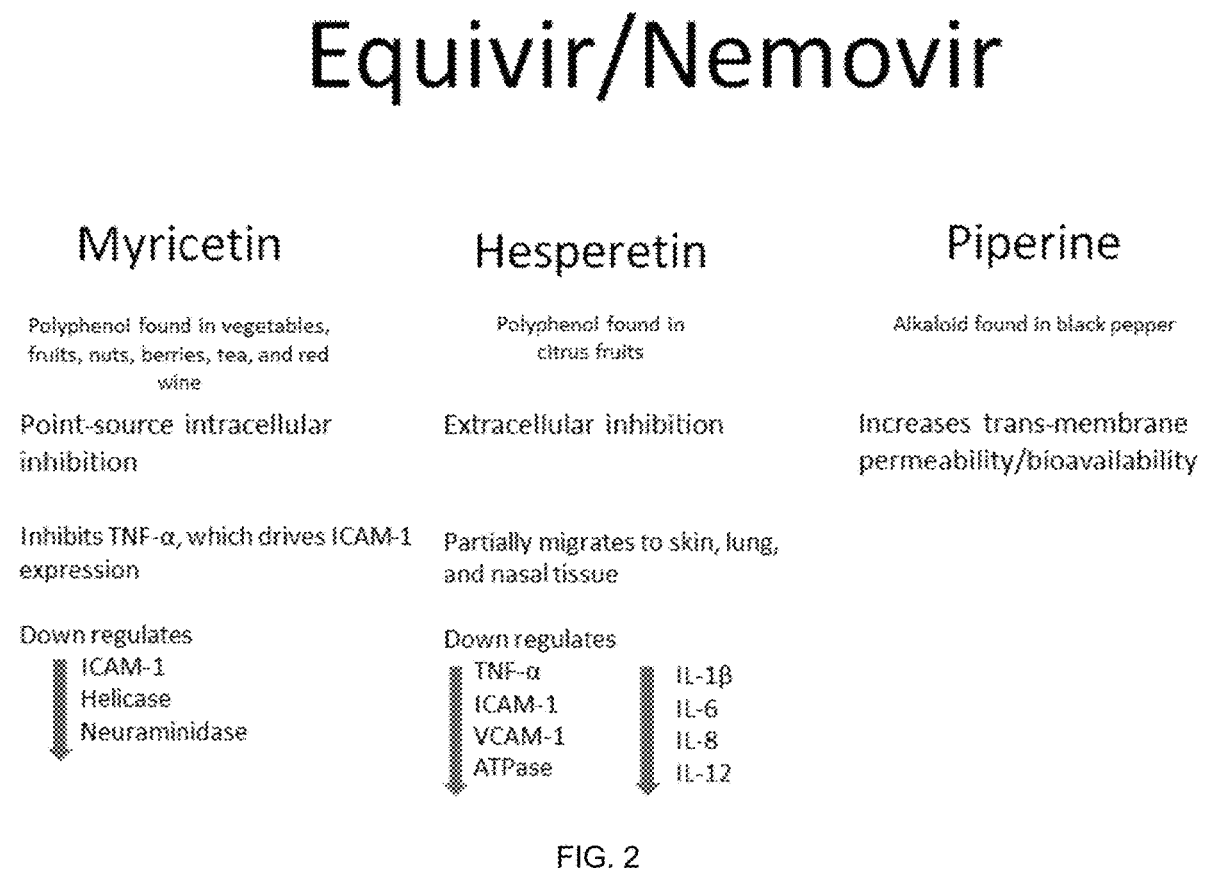

Equivir/Nemovir

Myricetin

Polyphenol found in vegetables, fruits, nuts, berries, tea, and red wine

Point-source intracellular inhibition

Inhibits TNF-α, which drives ICAM-1 expression

Down regulates
  - ICAM-1
  - Helicase
  - Neuraminidase

Hesperetin

Polyphenol found in citrus fruits

Extracellular inhibition

Partially migrates to skin, lung, and nasal tissue

Down regulates
  - TNF-α
  - ICAM-1
  - VCAM-1
  - ATPase
  - IL-1β
  - IL-6
  - IL-8
  - IL-12

Piperine

Alkaloid found in black pepper

Increases trans-membrane permeability/bioavailability

FIG. 2

Day-1

| Vehicle-High | 100 ug /ml |
|---|---|
| 50 ug /ml | 25 ug /ml |
| 12.5 ug /ml | 6.25 ug /ml |
| 3.12 ug /ml | 1.56 ug /ml |
| 0.78 ug /ml | Vehicle-Low |

FIG. 3

Day-2

Days-3

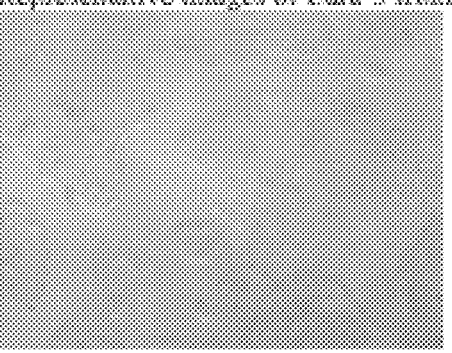
FIG. 14a
Representative images of Calu-3 from D2 and D3 (48 and 72hr PI)
Untreated/uninfected
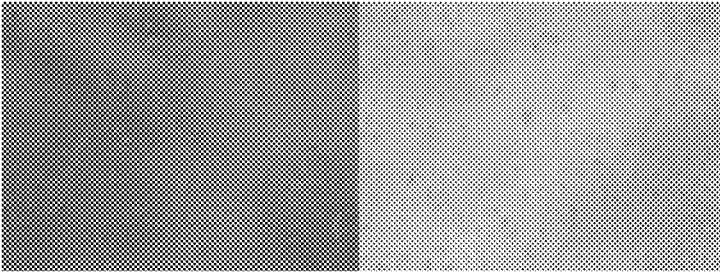
FIG. 14b Uninfected Infected Untreated Infected 50uM Equivir Representative images of Calu-3 from D0 (untreated cells)

Representative images of Treated Calu-3 from D2/D3 (48/72hr PI)
-2hr group: Treatments were added to cells 2 hours prior to infection with SARS-CoV-2.

Untreated/uninfected

Equivir 200 µg/ml treated cells 48 / 72 hours

Equivir 150 µg/ml treated cells 48 / 72 hours

Equivir 100 µg/ml treated cells 48 / 72 hours

Equivir 50 μg/ml treated cells 48 / 72 hours

Equivir 25 μg/ml treated cells 48 / 72 hours

Equivir (200 μg/ml) + Gallic Acid (20 μg/ml)

Equivir (150 µg/ml) + Gallic Acid (15 µg/ml)

Equivir (100 µg/ml) + Gallic Acid (10 µg/ml)

Equivir (50 µg/ml) + Gallic Acid (5 µg/ml)

Equivir (25 µg/ml) + Gallic Acid (2.5 µg/ml)

+2hr Group: Treatment was added 2 hours after infection with SARS-CoV-2
Equivir 200 µg/ml +2hr Group: Treatment was added 2 hours after infection with SARS-CoV-2
Equivir 150 µg/ml +2hr Group: Treatment was added 2 hours after infection with SARS-CoV-2
Equivir 100 µg/ml +2hr Group: Treatment was added 2 hours after infection with SARS-CoV-2
Equivir 50 µg/ml +2hr Group: Treatment was added 2 hours after infection with SARS-CoV-2
Equivir 25 µg/ml +2hr Group: Treatment was added 2 hours after infection with SARS-CoV-2
Equivir (200 μg/ml) + Gallic Acid (20 μg/ml)

+2hr Group: Treatment was added 2 hours after infection with SARS-CoV-2
Equivir (150 μg/ml) + Gallic Acid (15 μg/ml)

+2hr Group: Treatment was added 2 hours after infection with SARS-CoV-2
Equivir (100 μg/ml) + Gallic Acid (10 μg/ml)

+2hr Group: Treatment was added 2 hours after infection with SARS-CoV-2
Equivir (50 μg/ml) + Gallic Acid (5 μg/ml)

+2hr Group: Treatment was added 2 hours after infection with SARS-CoV-2
Equivir (25 μg/ml) + Gallic Acid (2.5 μg/ml)

METHOD AND COMPOSITION FOR PREVENTING AND TREATING VIRAL INFECTIONS

CROSS REFERENCE TO RELATED APPLICATIONS

This application is a continuation-in-part of application Ser. No. 16/642,976, filed Feb. 28, 2020, issuing on Apr. 26, 2022 as U.S. Pat. No. 11,311,563 which is the National Stage of International Application No. PCT/US2017/048892, filed Aug. 28, 2017 (all hereby incorporated by reference).

FIELD OF THE INVENTION

The present disclosure relates generally to limiting the occurrence of and/or treating viral infections, and more particularly to a therapeutic method and a therapeutic composition having a helicase ATPase inhibitor, a sialidase enzyme inhibitor, an ICAM-1 inhibitor and gallic acid, advantageously administered to a patient at risk of, or diagnosed with, a viral infection.

BACKGROUND OF THE INVENTION

Many human diseases result from infection by microscopic organisms called viruses. Infection by viruses can give rise to symptoms that vary from mild to severe. Viral infections can result in large numbers of deaths. Examples of such pandemics include the Spanish flu of 1918-1919 that killed approximately 40 million people and the HIV/AIDS epidemic that has killed almost 2 million people.

Viruses require host organisms in order to replicate and viruses are transmitted from an infected host to an uninfected host through a number of mechanisms. A virus will first attach itself to a host cell. It will then enter the cell and release its genetic code (i.e., RNA or DNA). The virus makes use of the host cell's functional proteins and enzymes in order to replicate. Eventually, the host cell may die because the mechanisms it needs to survive are controlled by the virus. After death of the cell, the replicated viruses are released, allowing them to attack new host cells and continuing the replication process. Some viruses cause modification of the host cells leading to cancer, while other viruses can remain dormant in the host for an extended period prior to the infection becoming symptomatic in the host.

The symptoms that result from viral infections can vary from virus-to-virus as any one virus typically will infect only certain types of cells. This observation also means that a specific virus will typically infect only certain species, although mutation of a virus can allow it to extend the number of species that any one virus is able to infect.

Host species have developed a number of defense mechanisms to protect themselves from viral infections. The first lines of defense are mechanisms that prevent viral entry into the host. The skin provides an impermeable barrier to entry. Viruses typically enter the body through body cavities and can pass through the mucosal surfaces that line these cavities. Once a virus is in the body and detected by the body's immune system, lymphocytes and monocytes in the blood learn how to attack the invader. Invaded cells release cytokines such as the interferons (for example IL 1, IL 6, IL 12, IL 16), tumor necrosis factor (TNF-a), and interferons (typically interferons a and g). The role of these cytokines is to increase the resistance of other host cells to the invading virus. Many of the symptoms of viral infection experienced by the host results from the extensive release of cytokines, commonly referred to as the cytokine storm.

The white blood cells are able to remember how to combat viruses that have previously invaded the body. So if the host survives the initial attack of the virus, the immune system is able to respond much more quickly to subsequent infections of the same virus. The body has developed an immunity to the virus. Such immunity can also be induced by presenting the immune system with a surrogate (vaccine) for the virus in a process known as immunization.

Antiviral drugs are known in the art to assist the immune system in overcoming a viral infection in a patient. Most antiviral drugs work by slowing the replication of the virus in the infected patient's body thus allowing the body's immune system to launch an effective response when the disease symptoms are less severe. Antiviral drugs may work specifically on one or two viruses or may be effective across a broad spectrum of viruses. There are many known mechanisms by which antiviral agents can slow viral replication. One antiviral strategy is to slow or prevent the virus infiltrating a target cell, for example by binding to a receptor on the target cell which is required by the virus to enter the cell or by coating the virus so preventing its ability to bind to the target receptor(s). Other antiviral agents can slow viral replication once the virus particle has entered the target cell. Such mechanisms are well known in the art.

SUMMARY OF THE INVENTION

The present invention relates to a method and composition for treating viral infections using a combination of naturally occurring compounds. In one embodiment, the method includes administering to a patient at risk of or diagnosed with a viral infection a composition including therapeutically effective amounts of a helicase ATPase inhibitor, a sialidase enzyme inhibitor an ICAM-1 inhibitor and gallic acid. The composition may further include a permeation enhancer.

The composition is effective in combating a viral infection by reducing replication rates for the virus and by reducing the virus's ability to stimulate the immune response of the host, thereby preserving cellular integrity. Specifically, the composition is effective in inhibiting the ATPase activity of the replication enzyme helicase on the cell surface by docking site competition. Moreover, the composition is effective in inhibiting the sialidase and ICAM-1 enzymes, which are involved in the entry and release stages of intercellular virus particles. Although not wishing to be limited to one function, it is believed that gallic acid will function as an inflammation and pain inhibitor, e.g. targeting TNF-α and nociceptors, respectively.

In one aspect of the invention there is provided a method of preventing and treating viral infections including administering a including therapeutically effective amounts of a helicase ATPase inhibitor, a sialidase composition enzyme inhibitor, an ICAM-1 inhibitor and gallic acid to a patient at risk of or diagnosed with a viral infection.

In another aspect of the invention there is provided a composition for treating viral infections including therapeutically effective amounts of a helicase ATPase inhibitor, a sialidase enzyme inhibitor, an ICAM-1 inhibitor and gallic acid.

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

In another embodiment, the helicase ATPase inhibitor includes a naturally occurring compound, a synthetic derivative of a naturally occurring compound or a combination thereof.

In another embodiment, the naturally occurring ATPase inhibitor compound includes a flavonoid, a flavonoid derivative or a combination thereof.

In another embodiment, the flavonoid ATPase inhibitor is myricetin.

In another embodiment, the I-CAM 1 inhibitor includes a flavonoid, a flavonoid derivative or a combination thereof.

In another embodiment, the ICAM-1 inhibitor is myricetin.

In another embodiment, the sialidase enzyme inhibitor includes a naturally occurring compound, a synthetic derivative of a naturally occurring compound or a combination thereof.

In another embodiment, the naturally occurring sialidase enzyme inhibitor compound includes a flavonoid, a flavonoid derivative or a combination thereof.

In another embodiment, the flavonoid sialidase enzyme inhibitor is hesperitin or hesperidin.

In another embodiment, the patient is a human.

In another embodiment, the composition further includes a permeation enhancer.

In another embodiment, the permeation enhancer is piperine.

In another embodiment, the helicase ATPase and ICAM-1 inhibitor is myricetin and the sialidase enzyme inhibitor is hesperitin.

In another embodiment, the composition further includes piperine.

In another embodiment, about 300 to about 700 mg myricetin; about 100 to about 500 mg hesperitin; about 5 to about 100 mg piperine and about 150 mg-300 mg gallic acid are present in the composition.

In another embodiment, about 450 to about 600 mg myricetin; about 250 to about 400 mg hesperitin; about 5 to about 50 mg piperine; and about 250-450 mg gallic acid are present in the composition.

In another embodiment, about 55 to about 75% weight myricetin; about 30 to about 50% hesperitin; and about 10% to 25% gallic acid, based on the total weight of the mixture, is present in the composition.

In another embodiment, the ratio of myricetin, hesperitin and gallic acid present in the composition is about (30-60): (30-60).

In another aspect of the invention there is provided a method of preventing and treating a viral infection in a human including administering a composition including 40% myricetin, 30% hesperitin, and 30% gallic acid, based on the total weight of the mixture, to a human at risk of or diagnosed with the viral infection.

In another aspect of the invention there is provided a composition for preventing and treating a viral infection including 60% myricetin, and 40% hesperitin collectively referred to herein as "Equivir", based on the total weight of the mixture. One advantageous therapeutic dose is about 1000 mg. The 4:3:3 ratio translates to 400 mg myricetin, 300 mg hesperitin and 300 mg gallic acid.

BRIEF DESCRIPTION OF THE DRAWINGS

FIG. 2 illustrates effects myricetin, hesperitin and piperine have on metabolic processes.

FIG. 3 illustrates the effect Equivir has on SARS-CoV-2 at various Equivir concentrations at Day 1.

FIG. 14a is an image of Calu-3 from DO (untreated cells).

FIG. 14b is an image showing untreated/unaffected representative of Calu-3 from D2 and D3 (48 and 72 hr PI).

FIGS. 56*a*-56*c* are graphs showing test compound induced cytokine secretions following 10 hour incubation with humans in which FIG. 56*a* is a graph for TNF-α, FIG. 56*b* is a graph for IL-1β and FIG. 56*c* is a graph for IL-6. Figure Key:

Neg=RPMI alone
DMSO=0.1% DMSO in RPMI
Myr=Myricetin
HES=Hesperidin
GA=Gallic Acid
MH=Myr+HES
GMH=GA+Myr+HES
*=p<0.0005 relative to Neg
Secretion of the cytokines TNF-α (A), IL-1β (B) and IL-6 (C) were measured in supernatant of PBMC cultured in the presence of test compounds using a Luminex platform with the Milliplex MAP Human High Sensitivity T Cell Panel Immunology Multiplex Assay. Results are represented as a mean from 3 separate donors in pg/mL.

Figure 57A:
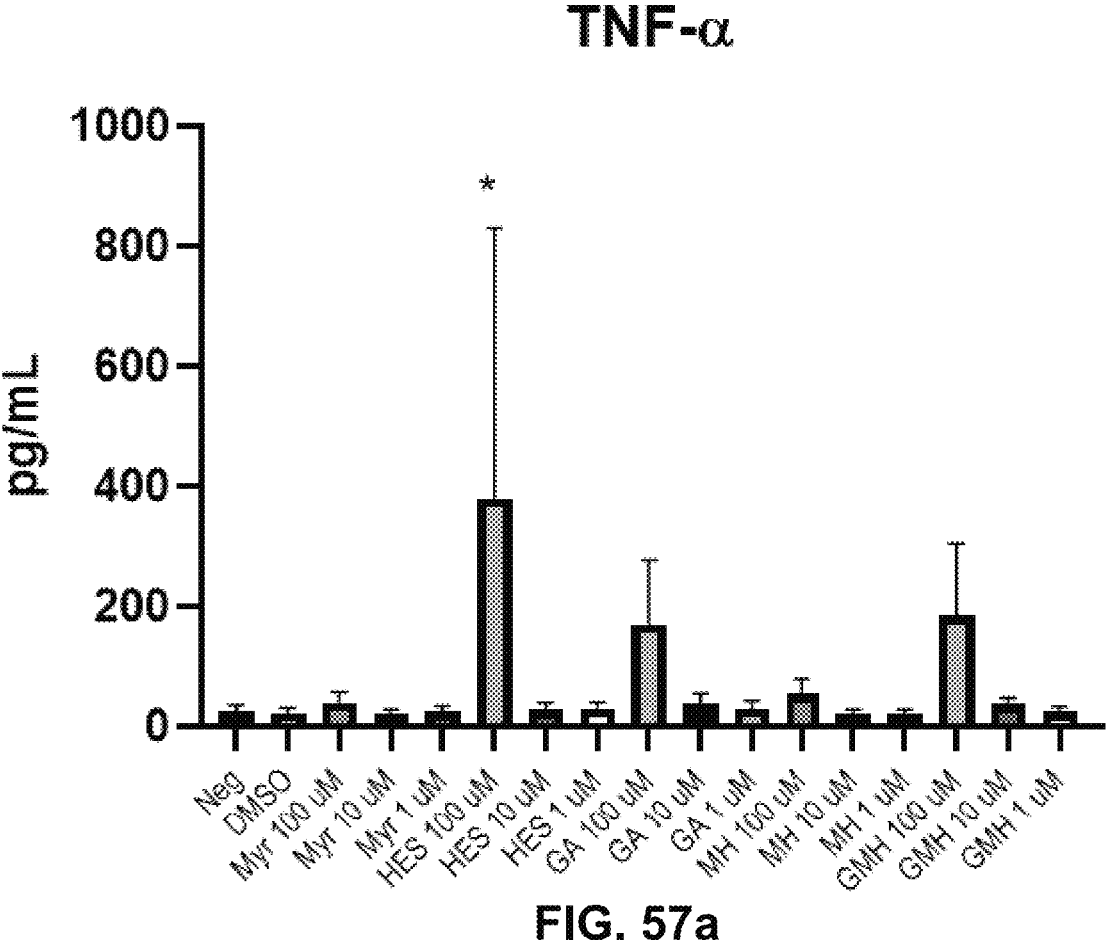
Figure 57B:
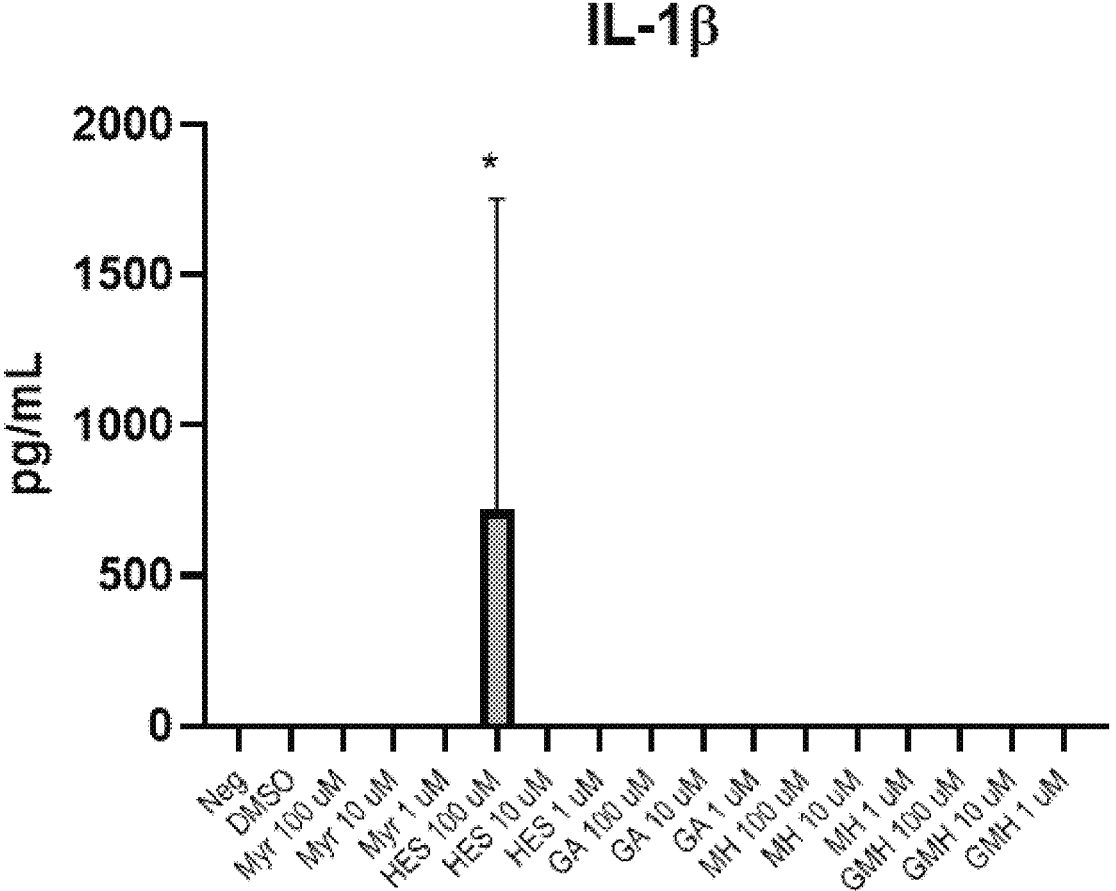
Figure 57C:
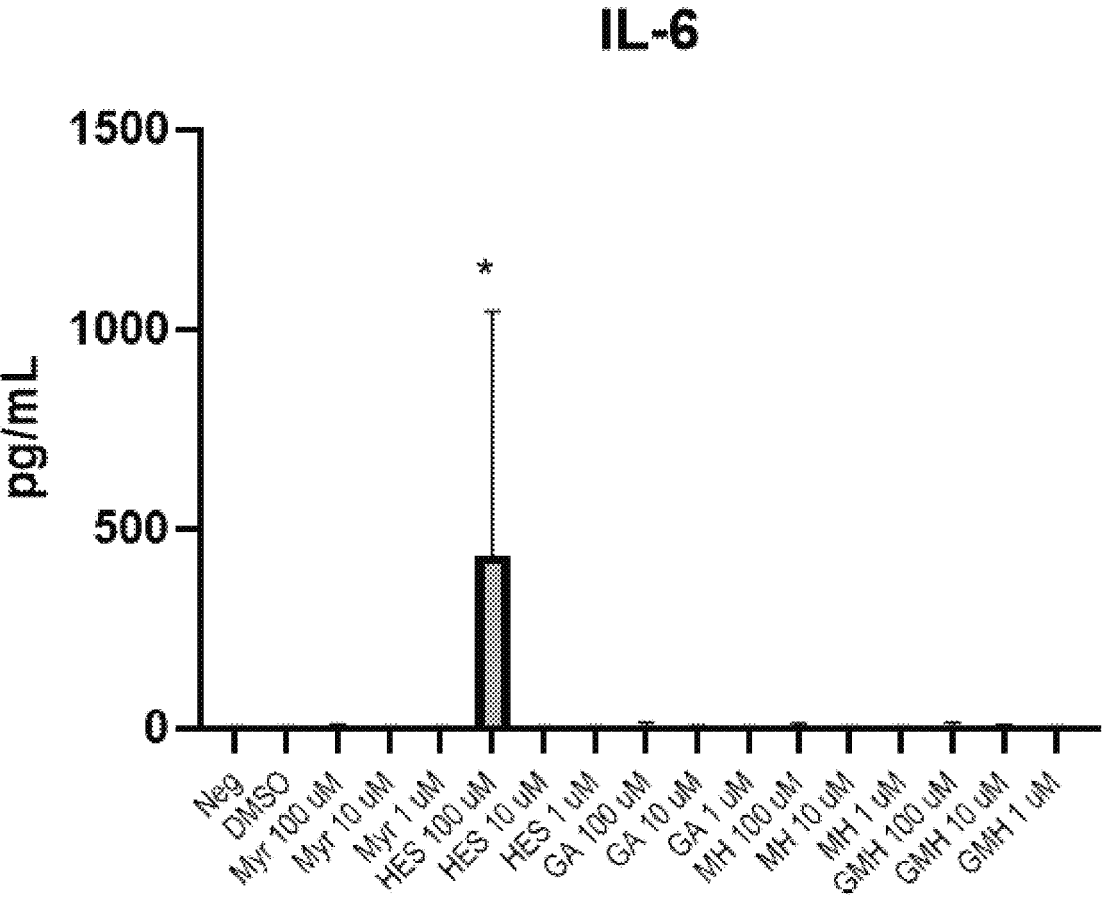

FIGS. 57*a*-57*c* are various graphs for test compound induced cytokine secretions following 26 hour incubation with human PBMCs in which FIG. 57*a* is for TNF-α, FIG. 57*b* is a graph for IL-1β and FIG. 57*c* is a graph for IL-6. Figure Key:

Neg=RPMI alone
DMSO=0.1% DMSO in RPMI
Myr=Myricetin
HES=Hesperidin
GA=Gallic Acid
MH=Myr+HES
GMH=GA+Myr+HES
*=p<0.0001 relative to Neg
Secretion of the cytokines TNF-α (A), IL-1β (B) and IL-6 (C) were measured in supernatant of PBMC cultured in the presence of test compounds using a Luminex platform with the Milliplex MAP Human High Sensitivity T Cell Panel Immunology Multiplex Assay. Results are represented as a mean from 3 separate donors in pg/mL.

Figure 58A:
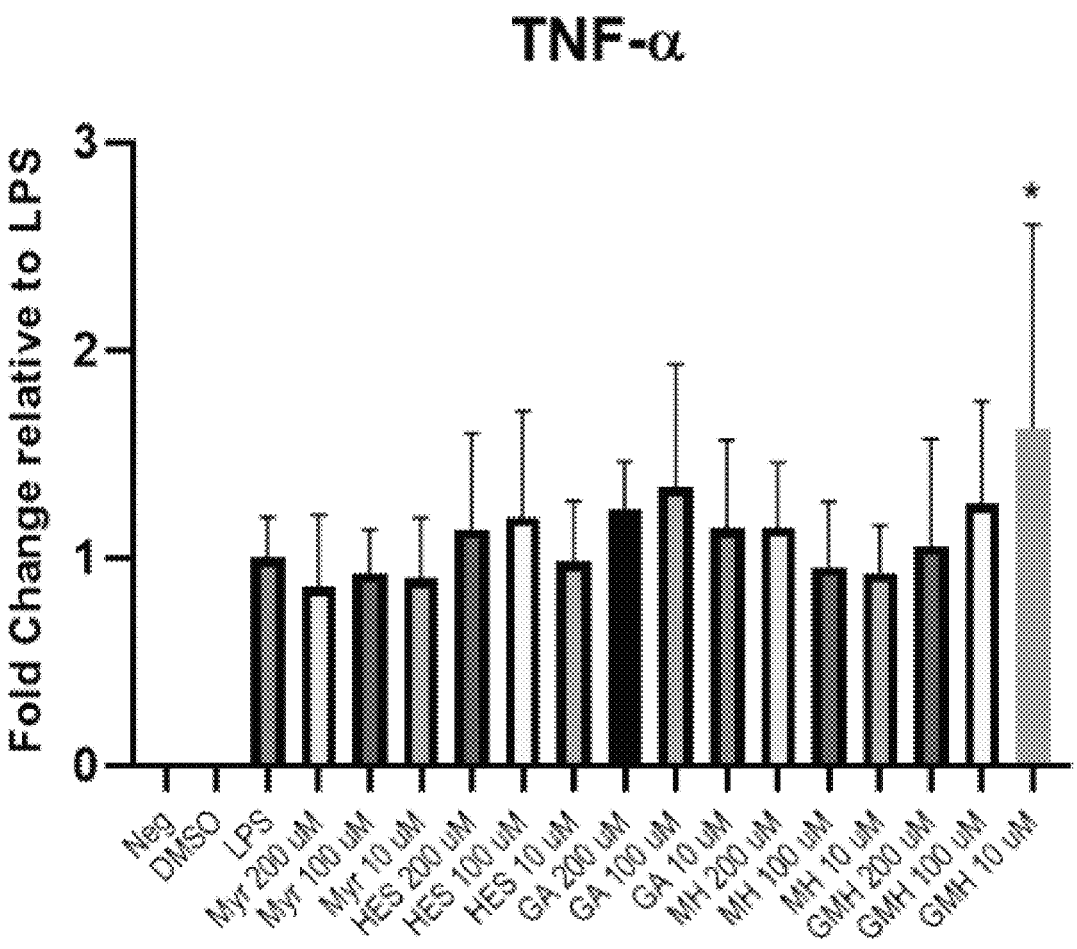
Figure 58B:
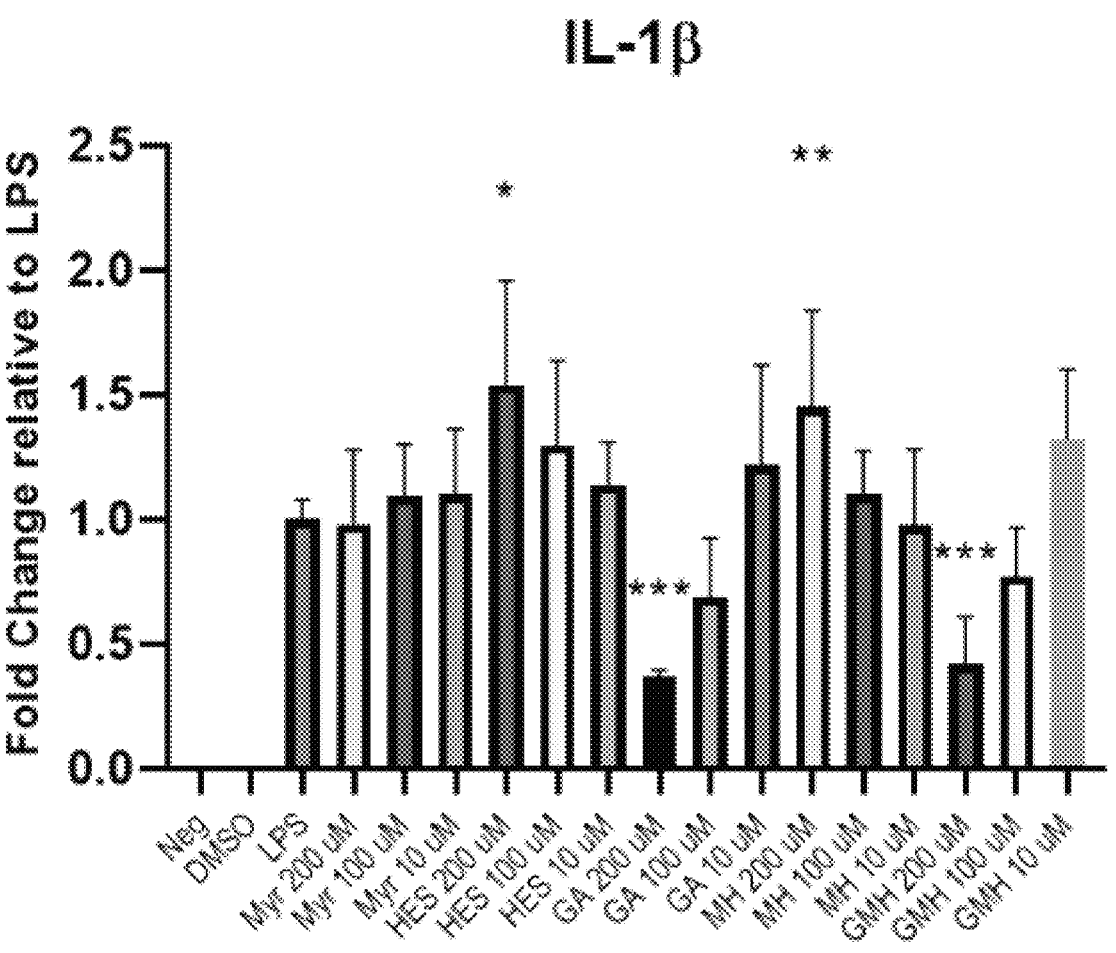
Figure 58C:
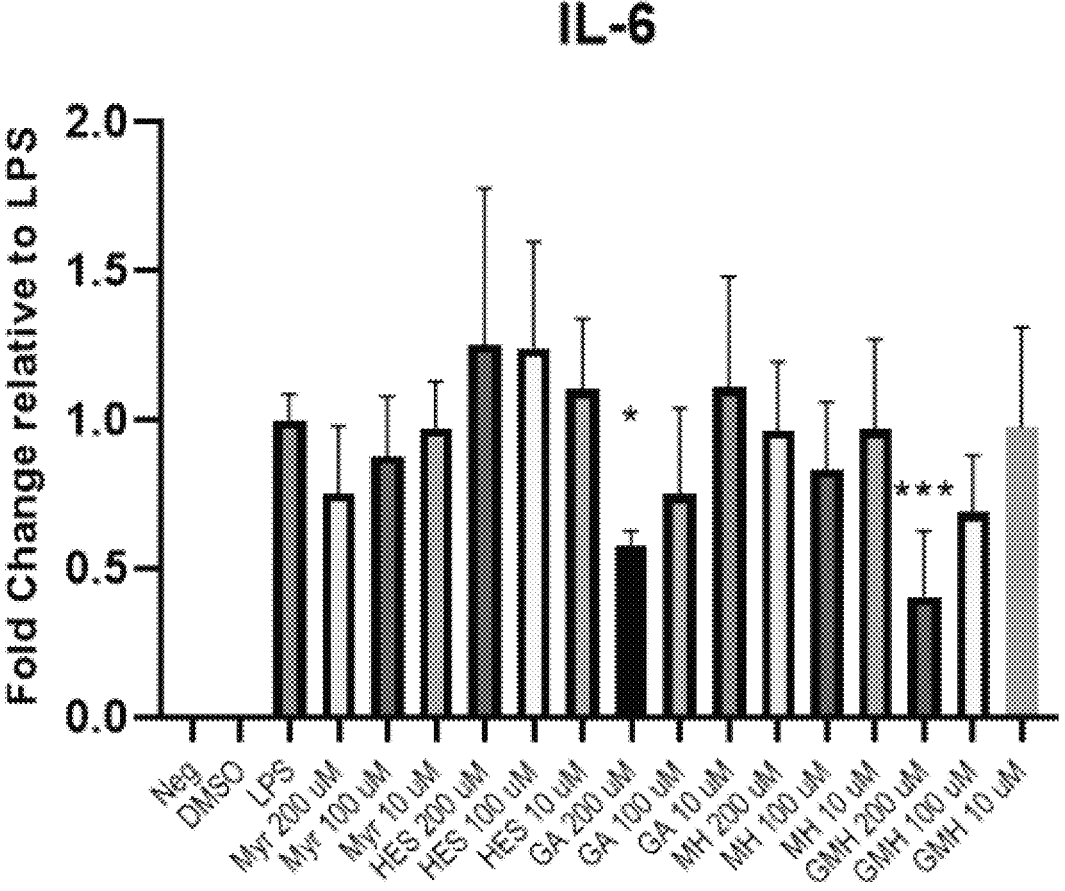

FIGS. 58*a*-58*c* are graphs for the effect of myricetin, hesperitin and gallic acid alone or in combination on human PBMC stimulated for 8 hours with LPS in which FIG. 58*a* is for TNF-α, FIG. 58*b* is a graph for IL-1β and FIG. 58*c* is a graph for IL-6.

FIGURE KEY

Neg=RPMI alone
DMSO=0.2% DMSO in RPMI
LPS=Lipopolysaccharide alone
Myr=Myricetin
HES=Hesperidin
GA=Gallic Acid
MH=Myr+HES
GMH=GA+Myr+HES
*=p<0.05, =p<0.005, *=p<00.0005
Relative to LPS treatment alone.
Note: All treatments simulated with 1 ng/ml LPS except for Neg and DMSO controls.
Secretion of the cytokines TNF-α (A), IL-1β (B) and IL-6 (C) in supernatant were measured using a Luminex platform with the Milliplex MAP Human High Sensitivity T Cell Panel Immunology Multiplex Assay. Results are represented as fold-change relative to LPS treatment alone for each cytokine calculated by means from 3 separate donors.

DETAILED DESCRIPTION

As used herein, the following terms and phrases shall have the meaning set forth below.

The phrase "naturally occurring" when referring to a compound means a compound that is in a form in which it can be found naturally. A compound is not in a form that is naturally occurring if, for example, the compound has been purified and separated from at least some of the other molecules that are found with the compound in nature. A "naturally occurring compound" refers to a compound that can be found in nature, i.e., a compound that has not been created or modified by man.

"Treating" a condition or disease refers to curing as well as ameliorating at least one symptom of the condition or disease.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the patient and disease or condition being treated, the weight and age of the patient, the severity of the disease or condition, the manner of administration and the like, which can readily be determined by one or ordinary skill in the art. For example, certain compositions described herein may be administered in a sufficient amount to produce a desired effect at a reasonable benefit/risk ratio applicable to such treatment.

The term "pharmaceutically acceptable carrier" means a carrier or diluent that does not give a stimulus to an organism and destroy the natures and bioactivities of an administered compound.

The present invention is directed to administering a composition comprising therapeutically effective amounts of a helicase ATPase inhibitor, a sialidase enzyme inhibitor, an ICAM-1 inhibitor, and gallic acid to a patient at risk of or diagnosed with a viral infection.

In one embodiment, the effective concentration for a composition consisting of a mixture by weight of a helicase ATPase inhibitor, a sialidase enzyme inhibitor, an ICAM-1 inhibitor and gallic acid, ranges from about 250 mg to about 1000 mg of the composition. In one embodiment, a single dose per day, taken at the beginning of the day, is about 750 mg, or about 1500 mg. In another embodiment, the composition is administered as a dose three times a day in an amount of about 750 mg per dose. The total amount of the composition administered daily, in one embodiment is at least 500 mg, or at least 750 mg, or at least 1000 mg or at least 2500 mg.

The helicase ATPase inhibitor of the present invention functions as a cellular replication inhibitor by inhibiting the ATPase activity of the replication enzyme helicase on the cell surface by docking site competition. This inhibition reduces viral un-packaging and replication rates and reduces mutation of viral strain due to the inhibiting activity taking place outside the cell.

In one embodiment, the helicase ATPase inhibitor includes a naturally occurring compound, a synthetic derivative of a naturally occurring compound or a combination thereof. There are several naturally occurring compounds that have an effect on viral infections.

In one embodiment, the naturally occurring ATPase inhibitor compound comprises a flavonoid, a flavonoid derivative or a combination thereof. Flavonoids are naturally-occurring antioxidant compounds for which several therapeutic uses have been demonstrated including diabetes, neurological disorders, thrombin inhibition, cancer, and antivirals. Generally, flavonoids generate few side-effects when administered and can safely be provided to patients in large doses. Two types of flavonoids that are useful are flavanones and flavones. Flavanones have the structure (I) shown below and flavones have the similar structure (II) shown below:

Flavanones (I)

Flavones (II)

wherein R, $R_1$, $R_2$, $R_3$, $R_4$, $R_5$ and $R_6$ are each independently hydrogen, a hydroxy group, an alkoxy group, a rutinosyl group, a rhamnosyl group, a substituted alkoxy group or a substituted acyloxy group wherein the substituent is chosen from hydroxyl, alkoxy, aryloxy, phenyl, halogen, and amido group. Several examples of the flavonoids of formula (I) and (II) are shown below in Table 1.

TABLE 1

|  | R | $R_1$ | $R_2$ | $R_3$ | $R_4$ | $R_5$ | $R_6$ |
|---|---|---|---|---|---|---|---|
| FLAVONE |  |  |  |  |  |  |  |
| Flavone | H | H | H | H | H | H | H |
| Chrysin | OH | OH | H | H | H | H | H |
| Apigenin | OH | OH | H | H | H | OH | H |
| Luteolin | OH | OH | H | H | H | OH | H |
| Diosmin | -0-rutinose | OH | H | H | OH | $OCH_3$ | H |
| Fisetin | OH | H | OH | H | OH | OH | H |
| Kaempferol | OH | OH | OH | H | H | OH | H |
| Morin | OH | OH | OH | OH | H | OH | H |
| Quercetin | OH | OH | OH | H | OH | OH | H |

TABLE 1-continued

| | R | $R_1$ | $R_2$ | $R_3$ | $R_4$ | $R_5$ | $R_6$ |
|---|---|---|---|---|---|---|---|
| Myricetin | OH | OH | OH | H | OH | OH | OH |
| Rutin | OH | OH | -0-rutinose | H | OH | OH | H |
| Rhoifolin | R-G-[a] | OH | H | H | H | OH | H |
| FLAVANONE | | | | | | | |
| Galangin | OH | OH | OH | H | H | H | H |
| Hesperetin | OH | OH | H | H | OH | $OCH_3$ | H |
| Eriodictyol | OH | OH | H | H | OH | OH | H |
| Naringenin | OH | OH | H | H | H | OH | H |
| Naringin | R-G-[a] | OH | H | H | H | OH | H |
| Neohesperidin | R-G-[b] | OH | H | H | OH | $OCH_3$ | H |
| FLAVANONE | | | | | | | |
| Hesoeridin | R-G-[b] | OH | H | H | OH | $OCH_3$ | H |
| Narirutin | R-G-[b] | OH | H | H | H | OH | H |
| Prunin | Glucose- | OH | H | H | H | OH | H |

[a]rhamnose-glucose, L-rhamnose is linked α 1–>2 to D-glucose
[b]rhamnose-glucose, L-rhamnose is linked α 1–>6 to D-glucose In one embodiment, the helicase ATPase inhibitor is the flavonoid myricetin.

Myricetin is a flavonoid found in most berries, including cherry, cranberry and bilberry, and other plants, including parsley and rutabagas. In addition to inhibiting the enzyme helicase, myricetin functions as a powerful and broad cytokine signaling inhibitor and immune-modulator. Myricetin down-regulates cytokine activity and TNF-A. This includes, for example, lymphokines, interleukines and chemokines, particularly interleukins IL-IL-36 and TNF-A.

Naturally occurring flavonoids, such as myricetin, are commonly substituted at variable positions, mainly by hydroxyl, methoxyl, isoprenyl and glycosyl groups. The introduction of halogens in these molecules show strong biological activities, including antiviral properties.

The ICAM-1 inhibitor of the present invention functions to slow viral replication inside the cell by inhibiting the ICAM-1 enzyme, which is involved in entry and release stages of intercellular virus particles.

In one embodiment, the ICAM-1 inhibitor is the flavonoid myricetin.

The sialidase of the present invention functions to slow viral replication inside the cell by inhibiting the sialidase enzyme, which is involved in entry and release stages of intercellular virus particles.

In one embodiment, the sialidase enzyme inhibitor comprises a naturally occurring compound, a synthetic derivative of a naturally occurring compound or a combination thereof. In another embodiment, the naturally occurring sialidase enzyme inhibitor compound comprises a flavonoid, a flavonoid derivative or a combination thereof.

In one embodiment, the sialidase enzyme inhibitor is the flavonoid hesperitin or hesperidin. Hesperidin is a flavonoid found in plants, mainly in citrus fruit peels.

Hesperitin is the aglycone form of hesperidin. In addition to inhibiting the sialidase enzyme, hesperitin and hesperidin function as cellular integrity agents by inhibiting cellular stratum acidification due to excessive histamine and histidine concentrations. Hesperitin and hesperidin further prevent integrin loss by inhibition of intracellular $H_2O_2$ production as well as activation of nuclear factor kB, phosphorylation of IkB (alpha), and inhibition of P-38 MAPK (mitogen activated kinase). Hesperitin and hesperidin further enhance cellular integrity by stimulating fibroblast collagen synthesis with associated enhancement of migration and proliferation.

There are several methods by which myricetin, hesperitin or hesperidin may be harvested from their original botanical sources. In one method, for example, extraction from botanical sources begins with a suitable seed material such as grape seeds or tomato seeds, pine bark or citrus rinds. The source material is macerated and flushed with water to separate the water soluble flavonoids from the bulkier pectins and fibers of the source material. This pulp wash is then treated with appropriate acids and bases as known in the art to cause precipitation. The precipitate is then washed again, dried and then concentrated to yield a fairly pure flavonoid composition. This composition may be further clarified to yield fractions containing the desired flavonoid product.

In another method, reverse osmosis may be used to remove the target flavonoid by filtering it out of juice streams from beverage manufacturing processes. The process of manufacturing fruit juices such as citrus, liberates the flavonoids from the rind and suspends them in the juice product. It is often desirable to remove these water soluble flavonoids because of their tendency to produce bitter or off flavors in the juice product.

For example, during the manufacture of grapefruit juice, the primary grapefruit flavonoid naringin is released into the juice stream. Because naringin has a very distinct bitter taste, it is necessary to remove it from the product stream via the use of resin coated reverse osmosis devices to restore the proper flavor profile of the grapefruit juice. The resultant flavonoid is finally collected and dried to yield a fairly pure product.

The flavonoids may also be manufactured by synthetic methods. Such methods may include an Allan-Robinson Reaction, which is a chemical reaction of o-hydroxylaryl ketones with aromatic anhydrides to form flavanones. Another example is Auwers Synthesis, which is a procedure that requires an acid catalyzed aldol condensation between benzaldehyde and a 3-oxypentanon to an o-hydroxychalcone. Further bromination of the alkene group gives a dibromo-adduct that rearranges to a flavanol by reaction with potassium hydroxide. A further example is a Baker-Venkataraman Rearrangement, which involves the reaction of 2-acetoxyacetophenones with base to form 1,3-diketones. The rearrangement reaction proceeds via enolate formation followed by an acyl transfer to form flavanones. An Algar-Flynn-Oyamada Reaction may also be used. In this reaction, a chalcone undergoes an oxidative cyclization to form a flavanol.

The present invention prevents and treats a wide variety of virus infections including, but not limited, to Cowpoxvirus, Herpesviridae, Herpes simplex viruses, Epstein-Barr virus, human adenoviruses, human papillomaviruses, hepatitis B virus, Retroviridae (such as human immunodeficiency virus), rotavirus, Filoviridae (such as Marburg virus and Ebola viruses), Dengue virus, influenza viruses, hanta virus, Severe acute respiratory syndrome coronavirus, Entero viruses, Rhino virus, Hepatitis virus, Norovirus, Norwalk virus, Alpha viruses, Chikungunya virus, Venezuelan equine encephalitis virus, Western equine encephalitis virus, Eastern equine encephalitis virus, St. Louis encephalitis virus, West Nile virus, Yellow fever virus, and Creutzfeldt-Jakob-Disease, Arbovirus, Flavivirus and RNA viruses.

In one embodiment, the viral infection is the Ebola virus. Viral Ebola's lethality is caused by the virus's ability to over stimulate the host's autoimmune response. The resulting saturation of the host's cytokine chemicals causes rapid cell adhesion loss due to the cytokine's destabilizing activity on integrin. The result is loss in cellular integrity and finally fatal hemorrhaging of vascular tissues and organs.

Ebola accomplishes this by secreting specific glycolproteins (e.g., secreted glycol-protein (sGP)) that interact with specific receptors on the cell surface to stimulate immune signaling response. The over-signaling initiates a cytokine response, which in turn initiates chemokine release. The resulting and overwhelming concentration of chemokines leads to integrin loss at the cellular level.

The present invention combats the Ebola virus by reducing replication rates for the virus and reducing the virus's ability to stimulate the immune response of the host, thereby preserving cellular integrity.

The composition of the present invention may be administered to patients at risk of viral infection, for example through exposure to patients known or suspected of having a viral disease, in order to prevent or lessen the severity of symptoms following infection and/or reduce the possibility of severe symptoms or death following infections.

The composition of the present invention may be administered to patients known or suspected of having a viral disease, in order to lessen the severity of symptoms and/or reduce the possibility of severe symptoms or death.

In one embodiment, the patient is a human. In other embodiments, the patient may be a mammal other than a human, such as a dog.

In one embodiment, the composition further includes a permeation enhancer. The permeation enhancer of the present invention functions to enhance oral uptake or cellular uptake of the helicase ATPase inhibitor, ICAM-1 enzyme inhibitor and the sialidase enzyme inhibitor.

In one embodiment, the permeation enhancer is piperine. Piperine is an alkaloid and is responsible for the pungency of black pepper and long pepper. Piperine is commercially available or may be extracted from black pepper using dichloromethane. Piperine increases the bioavailability of nutrients.

In one embodiment, the helicase ATPase inhibitor and ICAM-1 inhibitor is myricetin, the sialidase enzyme inhibitor is hesperitin and the composition further includes piperine and gallic acid.

In one embodiment, the composition includes about 300 to about 700 mg myricetin; about 100 to about 500 mg hesperitin; and about 5 to about 100 mg piperine. In another embodiment, the composition includes about 450 to about 600 mg myricetin; about 250 to about 400 mg hesperitin; about 5 to about 50 mg piperine, and about 100 to about 300 mg gallic acid.

In one embodiment, the composition includes a mixture of about 50 to about 80% weight myricetin; about 25 to about 55% hesperitin; about 0.5 to about 10% piperine; and about 10-30% gallic acid based on the total weight of the mixture. In another embodiment, the composition includes a mixture of about 55 to about 75% weight myricetin; about 30 to about 50% hesperitin; about 0.5 to about 5% piperine, and about 20-40% gallic acid based on the total weight of the mixture. In yet another embodiment, the composition includes a mixture of about 40% myricetin; about 30% hesperitin; 1% piperine, and 29% gallic acid based on the total weight of the mixture.

In one embodiment, the composition includes a ratio of piperine to myricetin to hesperitin of about 1:(2-4):(2-4), or about 1:(2-3):(2-3), or about 1:3:3. In another embodiment, the composition includes a ratio of piperine to myricetin to hesperitin to gallic acid of about 1:(20-75):(20-75):(20-75), or about 1:(30-60):(30-60):(30-60), or about 1:(40-55):(40-55).

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, each containing a predetermined amount of a compound of the present invention as an active ingredient.

In solid dosage forms of the invention for oral administration, the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the pharmaceutical compositions may also comprise buffering agents.

Embodiments of inventive compositions and methods are illustrated in the following examples. These examples are provided for illustrative purposes and are not considered limitations on the scope of inventive compositions and methods.

EXAMPLES

Example 1

A gelatin capsule containing 300 mg myricetin, 195 mg hesperitin, 5 mg piperine and 200 mg gallic acid is administered orally to a patient twice a day, taken with food.

Example 2

A tablet containing sodium citrate, 500 mg myricetin, 300 mg hesperitin, 10 mg piperine and 300 mg gallic acid is administered orally once a day upon rising.

Example 3

A powder containing 600 mg myricetin, 390 mg hesperitin, 10 mg piperine and 200 mg gallic acid is sprinkled onto foods such as, for example scrambled eggs after cooking but prior to consumption.

Example 4

A composition containing a blend of 50% by weight myricetin, 25% by weight hesperitin, 10% by weight piperine and 15% gallic acid is blended into a saline solution and is injected intravenously, such that there is 1 mg of the composition per 1 g of saline solution.

Experimental Goal of Studies 1-4

Goal:

To determine the effectiveness of "flavonoid compounds" in limiting the replication of SARS-CoV-2.

Brief Summary of Work:

Vero E6 cells will be treated with various concentrations of four compounds sent by GlobalIRDG to PSU. Treated and untreated cells will then be infected with a predetermined concentration of SARS-CoV-2 USA/WA1-2020 strain. These cells will be monitored for survival/health for up to 72 hours post-infection.

Modification: Change in maximum concentrations of the compounds to be tested.

Specific Experiments:

A. Determination of Efficacy of Compounds Against SARS-CoV-2:

1. Vero E6 cells will be grown to a density of 105 cells per well in 24 well plate.

2. Cells will be treated with four compounds at concentrations ranging from 0 μg/ml concentration to a maximum concentration of 100 μg/ml concentration for solid powder compound and maximum dilution of $\frac{1}{1000}$ to $\frac{1}{20000}$ of liquid compound with three wells per each concentration for 2 hours before infection.

3. Cells will be infected with SARS-CoV-2 (USA/WA1-2020) at a viral concentration of $5 \times 10^3$ TCID50.

4. Health of cells will be monitored by light microscopy every 24 hours for 72 hours post infection. Specifically look of cytopathic effects, rounding of cells, sloughing of cells from the bottom of wells.

5. Cell death will be measured by LDH release assay at 72 hours post-infection.

Studies

The present composition and method will now be described with reference to the following studies.

The following studies were conducted to demonstrate efficacy of Equivir against coronavirus:

Study #1

Objective:

To determine the effect of Equivir against SARS-CoV-2 in Vero E6 cells.

Figure 1:
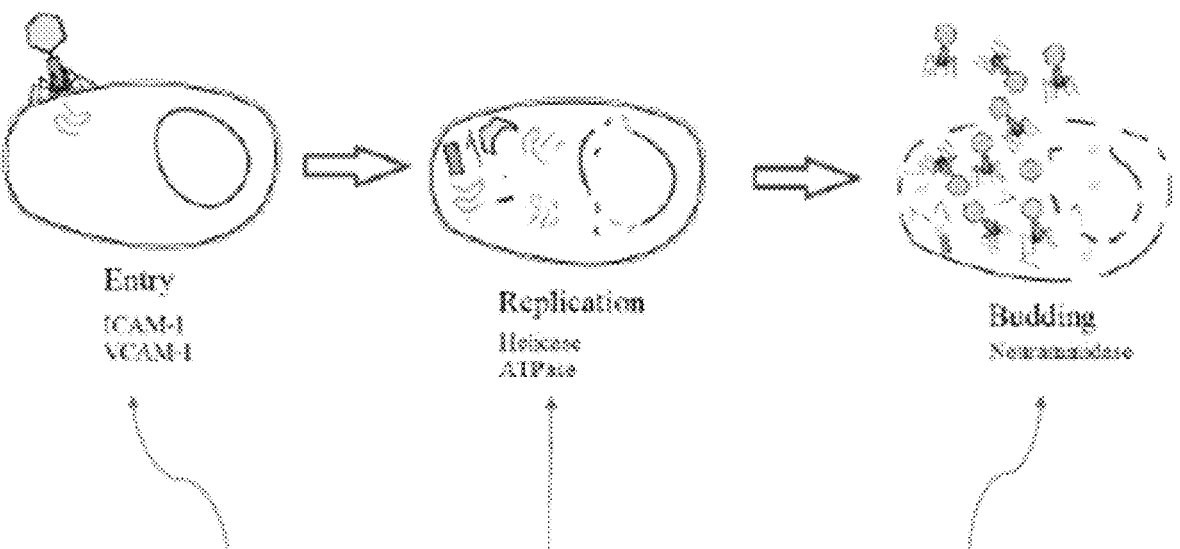
FIG. 1 shows a synergistic effect of Equivir on virus replication.
Figure 4:
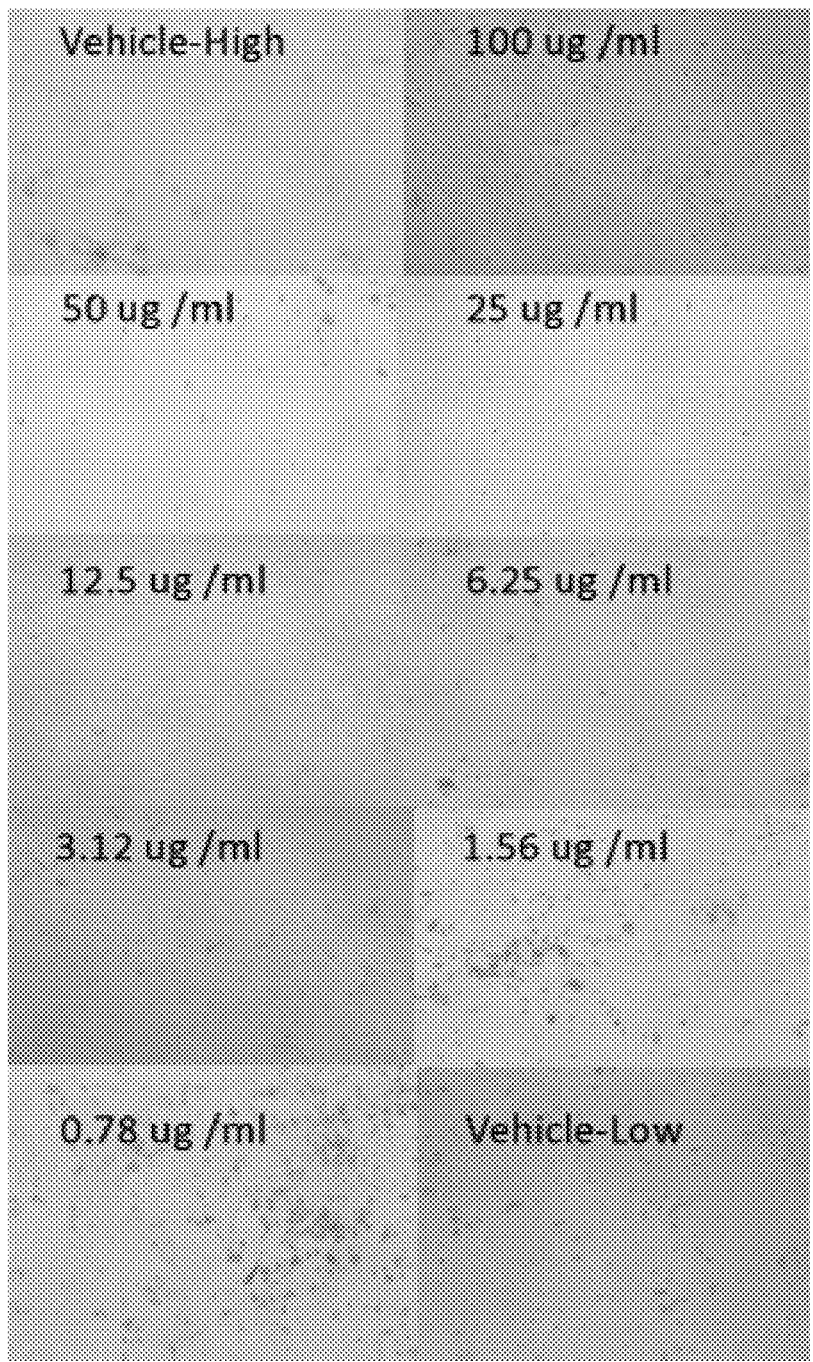
FIG. 4 illustrates the effect Equivir has on SARS-CoV-2 at various Equivir concentrations at Day 2.
Figure 5:
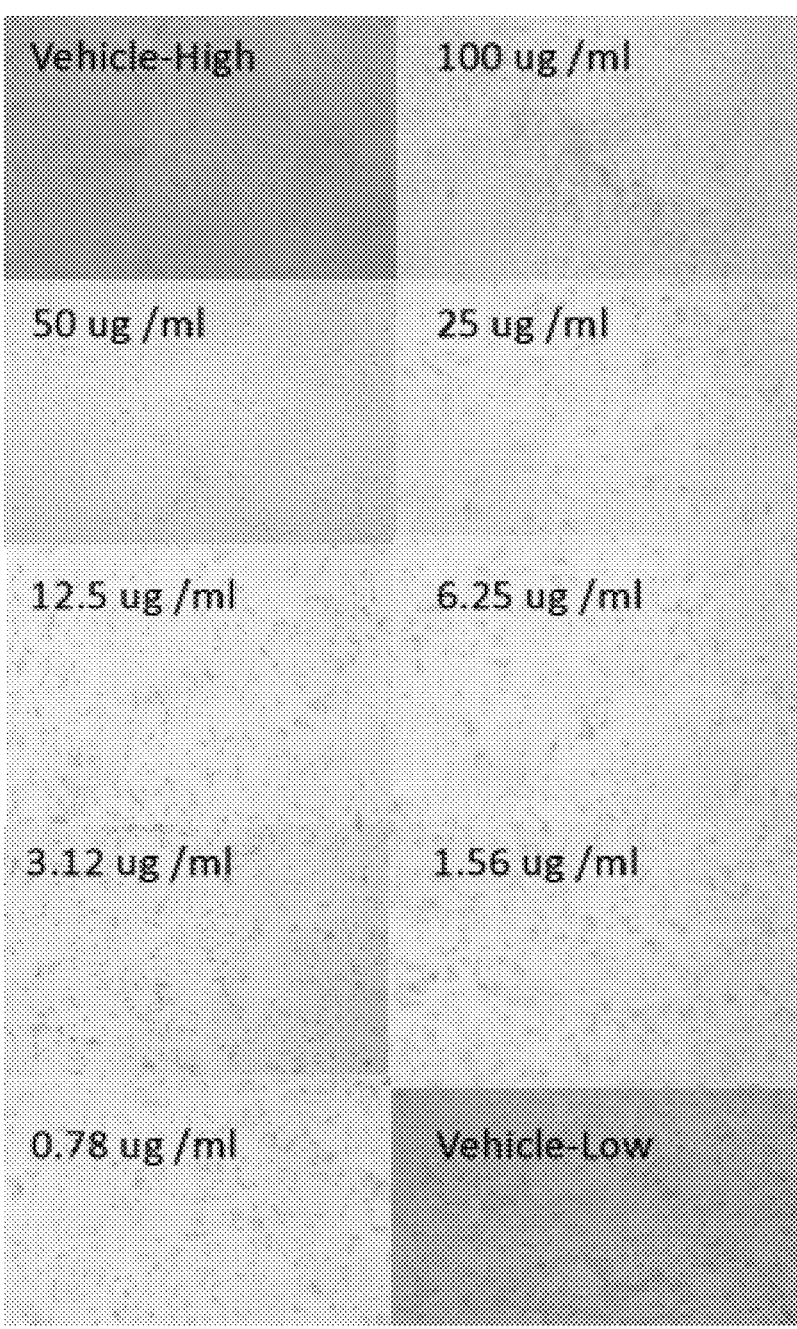
FIG. 5 illustrates the effect Equivir has on SARS-CoV-2 at various Equivir concentrations at Day 3.

Experimental Overview:

Vero E6 cells were seeded at a density of $1.5 \times 10^5$ cells/well in 24-well plates. Eight dilutions of each provided compound (Equivir, myricetin and hesperitin) and vehicle treatment (DMSO) were added simultaneously with SARS-CoV-2 (MOI: 0.03). Each concentration was tested in triplicate wells. Wells were imaged daily, and an LDH cytotoxicity assay was completed on the final day of the experiment (D3). FIGS. 3-5 are photographs representative of each concentrations on days 1-3, and are below. Representative protocol is shown below in Study 2.

Concentrations of Equivir Tested:

Equivir (μg/ml): 100, 50, 25, 12.5, 6.25, 3.125, 1.5625 and 0.78125.

Representative Protocol for Testing Equivir:

Protocol for Testing Compound LB-1

Day 1

Compound Stock Solution Preparation (Inside the BSC in MSC).

Weigh 20 mg of the compound and resuspend it in 1 ml of DMSO (cell culture grade).

Vortex well and make 10 aliquots of 100 μl. Label and store them at −20° C.

Seeding of Cells (Day before infection) (Inside BSC in Pell)

Resuspend Vero E6 cells to a final concentration of $1.5 \times 10^5$ cell/ml in MEM+10% FBS with 1× Penn/Strep.

Add 1 ml of cell suspension to each well in a 24-well plate.

Place them in $CO_2$ incubator at 37° C. O/N.

Day 0

Compound working solution preparation (Inside the BSC in MSC).

Prepare MEM with 2% serum plus 1× Pen/Strep.

Prepare one 10 ml sterile tube with 9.9 ml of medium. Label the tube as #1.

Prepare seven 10 ml sterile tubes with 5 ml of medium. Label the tubes as #2 to #8.

Thaw one of the tubes containing stock solution of the compound.

Add 100 μl stock solution to tube #1. Vortex well.

Transfer 5 ml from tube #1 to tube #2. Vortex well and repeat till tube #8.

Store the tubes on ice for transport to Pell.

Infection and Treatment (Inside the BSC in Pell).

Virus Preparation

Prepare Virus (SARS-CoV-2, WA1/USA-2020)

Virus Stock Concentration: $1 \times 10^{6.25}$ TCID50

Target infection MOI: 0.05 MOI

Resuspend 0.5 ml virus stock in 50 ml of MEM with 2% serum and 1× Pen/Strep (to a final concentration of $1 \times 10^{4.25}$ TCID50/ml.

Cell Preparation (Inside the BSC in Pell)

Observe under microscope and take a picture in Class IIA BSC

Transfer plates to Class IIB BSC

Remove O/M medium from the 24-well plates by suction

Add 0.5 ml virus suspension to each well (to all wells)

Add 0.5 ml of compound at each concentration to three wells from Tubes #1 to #8

Final concentration of Equivir show in in the table below:

| 100 μg/ml | 100 μg/ml | 100 μg/ml | 6.25 μg/ml | 6.25 μg/ml | 6.25 μg/ml |
|-----------|-----------|-----------|------------|------------|------------|
| 50 μg/ml | 50 μg/ml | 50 μg/ml | 3.125 μg/ml | 3.125 μg/ml | 3.125 μg/ml |

-continued

| 25 μg/ml | 25 μg/ml | 25 μg/ml | 1.5625 μg/ml | 1.5625 μg/ml | 1.5625 μg/ml |
|---|---|---|---|---|---|
| 12.5 μg/ml | 12.5 μg/ml | 12.5 μg/ml | 0.78125 μg/ml | 0.78125 μg/ml | 0.78125 μg/ml |

Mix media in the wells by gently swirling the plates.
Transfer plates to incubator.
Day 1
Remove plate from incubator.
Observe cells under microscope in Class IIA BSC
Take a picture of cells at each concentration.
Transfer plates to incubator.
Day 2
Remove plate from incubator.
Observe cells under microscope in Class IIA BSC
Take a picture of cells at each concentration.
Transfer plates to incubator.
Day 3
Remove plate from incubator.
Observe cells under microscope in Class IIA BSC licate wells. Wells were imaged daily, and an LDH cytotoxicity assay was completed on the final day of the experiment (D3). Representative images of each concentrations on day 3 are below.

Concentrations of Equivir Tested:

Equivir (μg/ml): 1000, 500, 250, 125, 62.5, 31.25, 15.625 and 7.8125.

Summary of Results:

Effectiveness of compounds against SARS-CoV-2 were tested by treating Vero E6 cells with various compounds added at the time of infection with a MOI of 0.01. Equivir was toxic at higher concentrations and not toxic at lower concentrations. Equivir was effective in inhibiting viral replication at non-toxic concentrations of 250, 125, and 62.5 μg/ml.

TABLE 3

| Baseline concentration | 25 μg/ml | 12.5 μg/ml | 6.25 μg/ml | 3.125 μg/ml | 1.5625 μg/ml | 0.78125 μg/ml | 0.39 μg/ml | 0.19 μg/ml |
|---|---|---|---|---|---|---|---|---|
| Equivir Concentration | 1000 μg/ml | 500 μg/ml | 250 μg/ml | 125 μg/ml | 62.5 μg/ml | 31.25 μg/ml | 15.625 μg/ml | 7.8125 μg/ml |
| Equivir effect | Toxic | Toxic | Effective | Effective | Effective | Not Effective | Not Effective | Not Effective |

Take a picture of cells at each concentration.
Transfer plate to Class IIB BSC
Remove 0.5 ml from each well and transfer to 1 ml eppendorff tubes. Label the tubes.
Set up centrifuge in Class IIB BSC.
Centrifuge tubes at 5,000 g for 5 min.
Transfer 100 μl from each tube to 96 well-plate
Perform LDH release assay as per the instruction of the kit.
Summary of Results:

Effectiveness of compounds against SARS-CoV-2 were tested by treating Vero E6 cells with various compounds added at the time of infection with a MOI of 0.03. Equivir showed no toxicity at tested concentrations and was effective in inhibiting viral replication at higher concentrations (100 and 50 μg/ml).

TABLE 2

| | Effectiveness of Equivir at different concentrations | | | | | | | |
|---|---|---|---|---|---|---|---|---|
| | 100 μg/ml | 50 μg/ml | 25 μg/ml | 12.5 μg/ml | 6.25 μg/ml | 3.125 μg/ml | 1.5625 μg/ml | 0.78125 μg/ml |
| Equivir | Effective | Effective | Effective | Not Effective | Not Effective | Not Effective | Not Effective | Not Effective |

Figure 6:
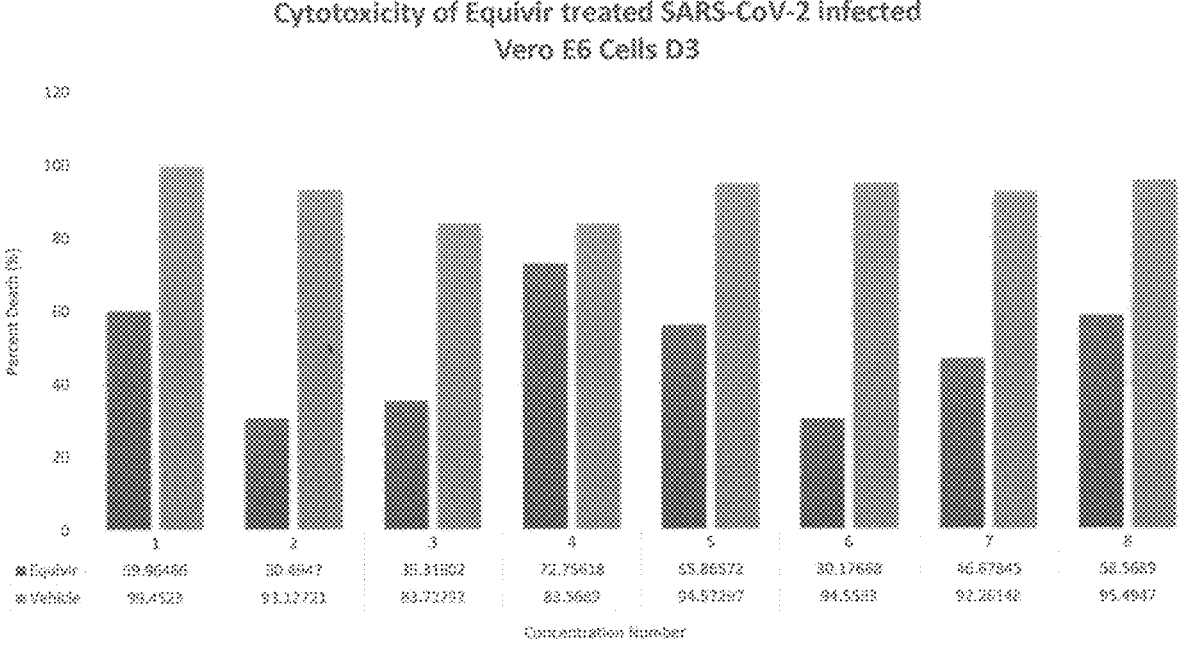
FIG. 6 is a graph showing cytotoxicity of Equivir treated SARS-CoV-2.

FIG. 6 is a graph that shows that Equivir is not toxic.
Study #2
Objective:

To determine the effect of Equivir against SARS-CoV-2 in Vero E6 cells.

Figure 7:
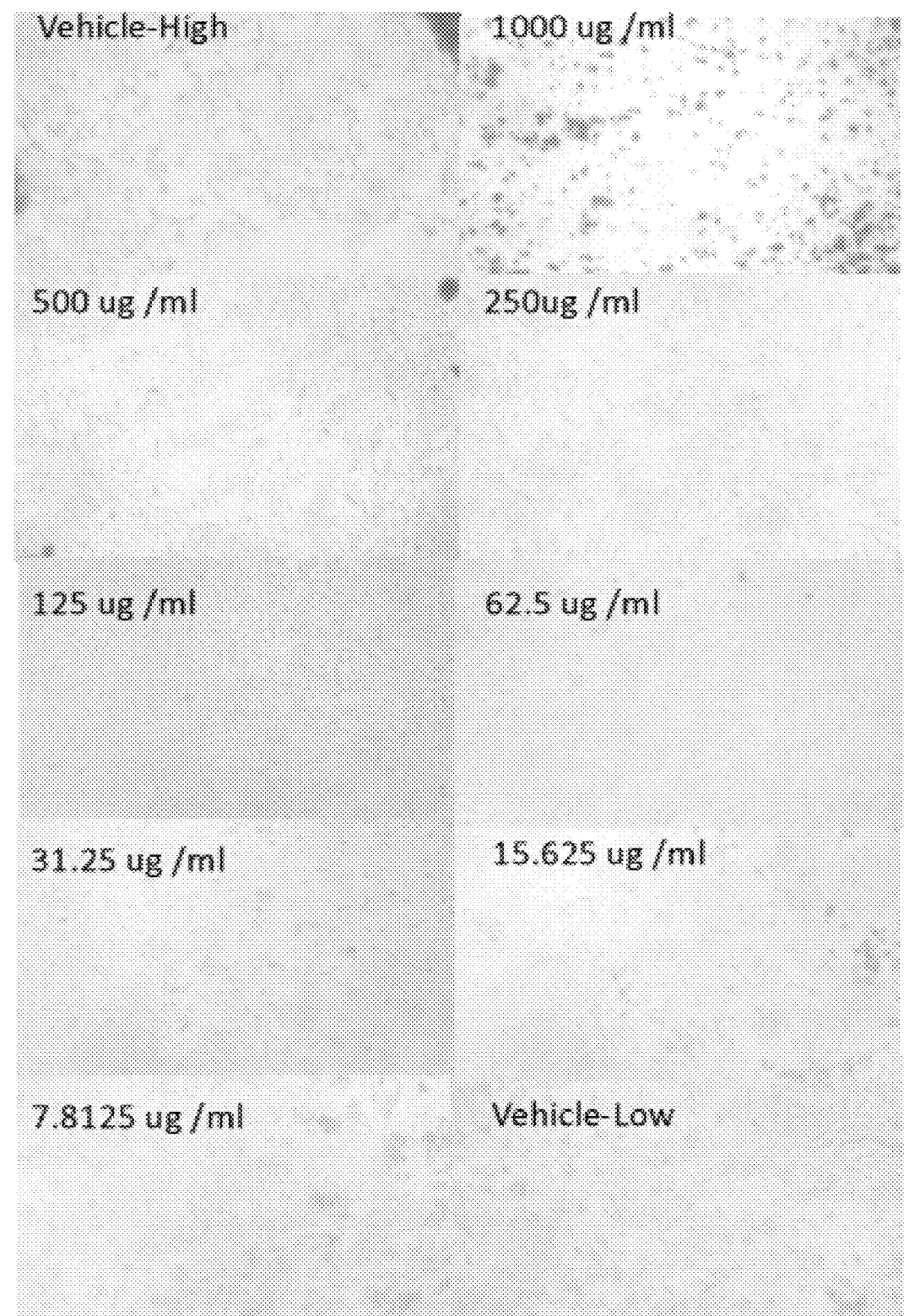
FIG. 7 illustrates effectiveness of various concentrations of Equivir against SARS-CoV-2.

Experimental Overview:

Vero E6 cells were seeded at a density of $5 \times 10^4$ cells/well in 96-well plates. Eight dilutions of Equivir and vehicle treatment (DMSO) were added simultaneously with SARS-CoV-2 (MOI: 0.01). Each concentration was tested in trip- FIG. 7 are photographs showing efficacy.

Figure 8:
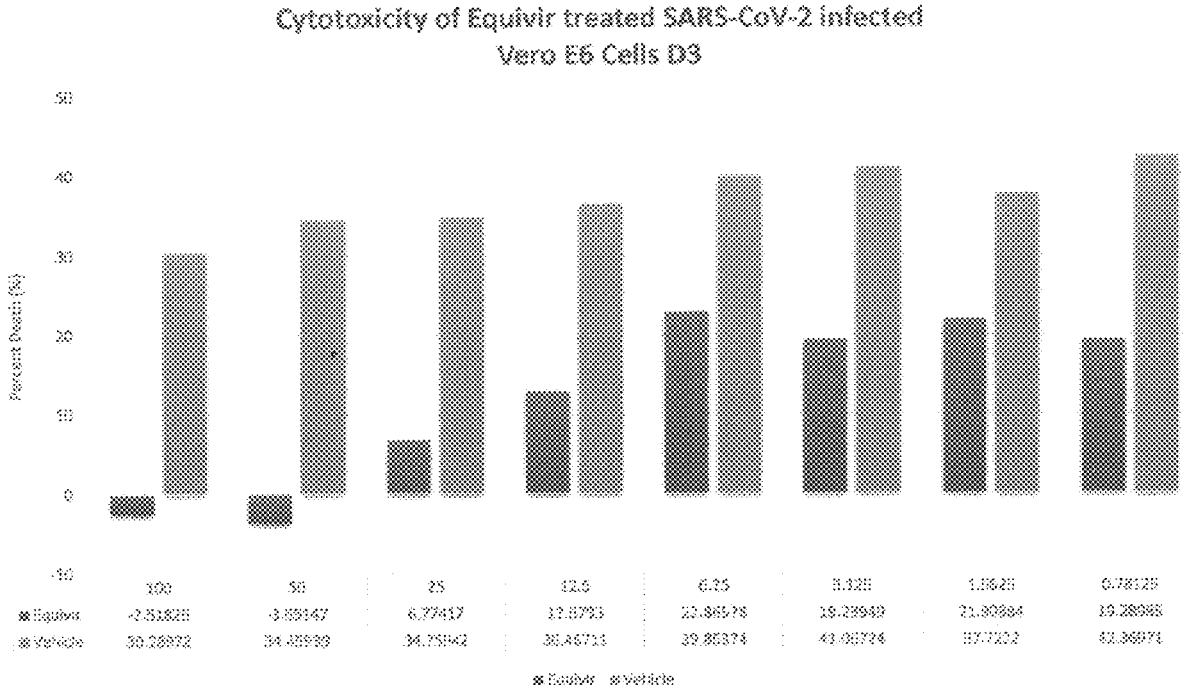
FIG. 8 is a graph showing cytotoxicity of Equivir treated SARS-CoV-2.

FIG. 8 is a graph showing cytotoxicity.

Study #3

Objective:

To determine the prophylactic and post-infection efficacy of Equivir treatment against SARS-CoV-2 in Vero E6 cells.

Experimental Overview:

Vero E6 cells were seeded at a density of $1.5 \times 10^5$ cells/well in 24-well plates. Four different concentrations of Equivir were added either 2 hours prior to or after infection with SARS-CoV-2 (MOI: 0.01). Each concentration was tested in triplicate wells. Wells were imaged daily, and an LDH cytotoxicity assay was completed on the final day of the experiment (D3). Representative images of each concentrations on day 3 are below.

Concentrations of Various Compounds Tested:

Equivir (μg/ml): 200, 100, 50, and 25.

These concentrations were chosen since no toxicity was observed at these concentrations and was effective when the virus and compound were added at the same time.

Figure 9:
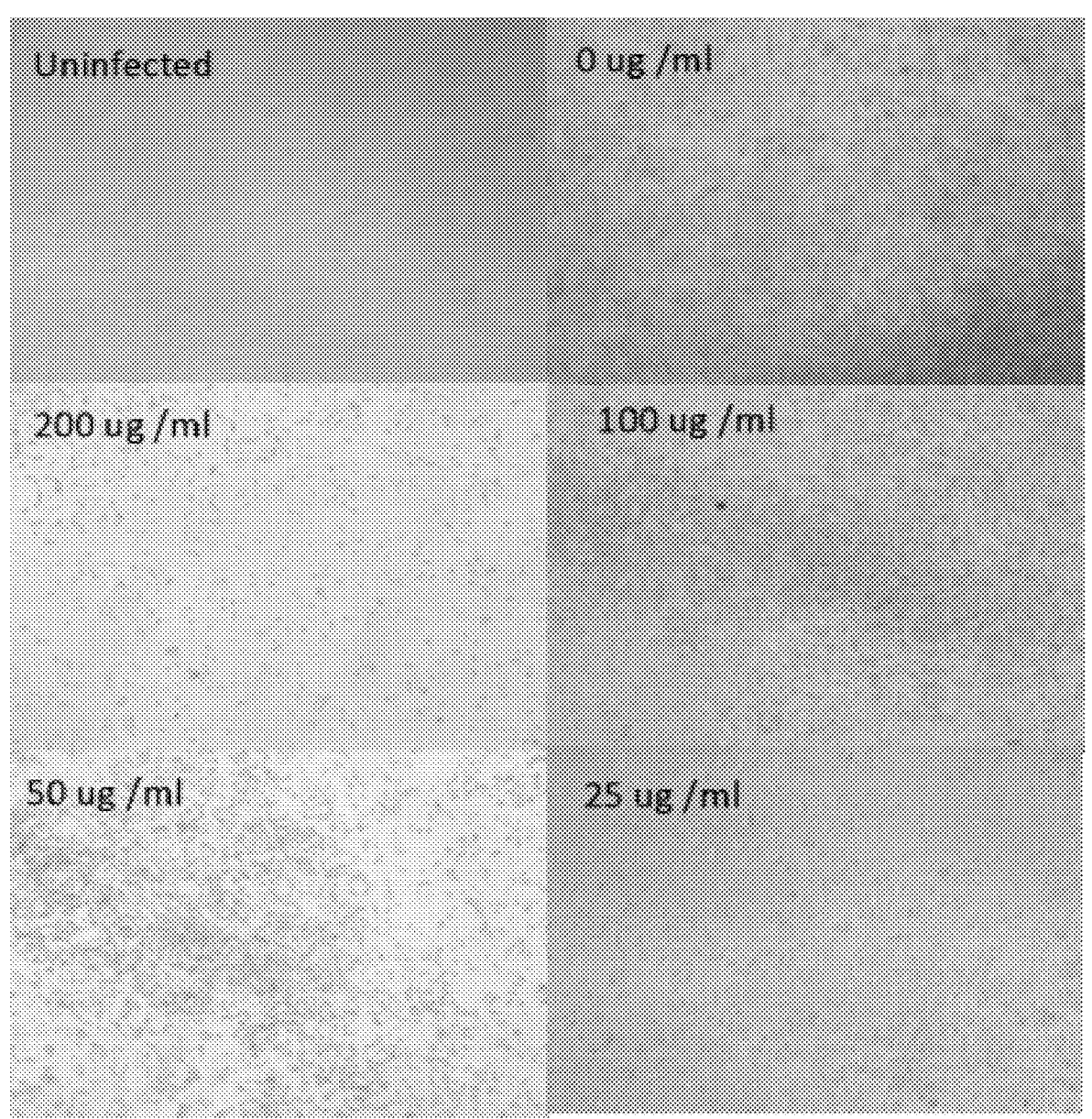
FIG. 9 shows the effectiveness of various concentrations of Equivir at less than 2 hours for various Equivir concentrations.
Figure 10:
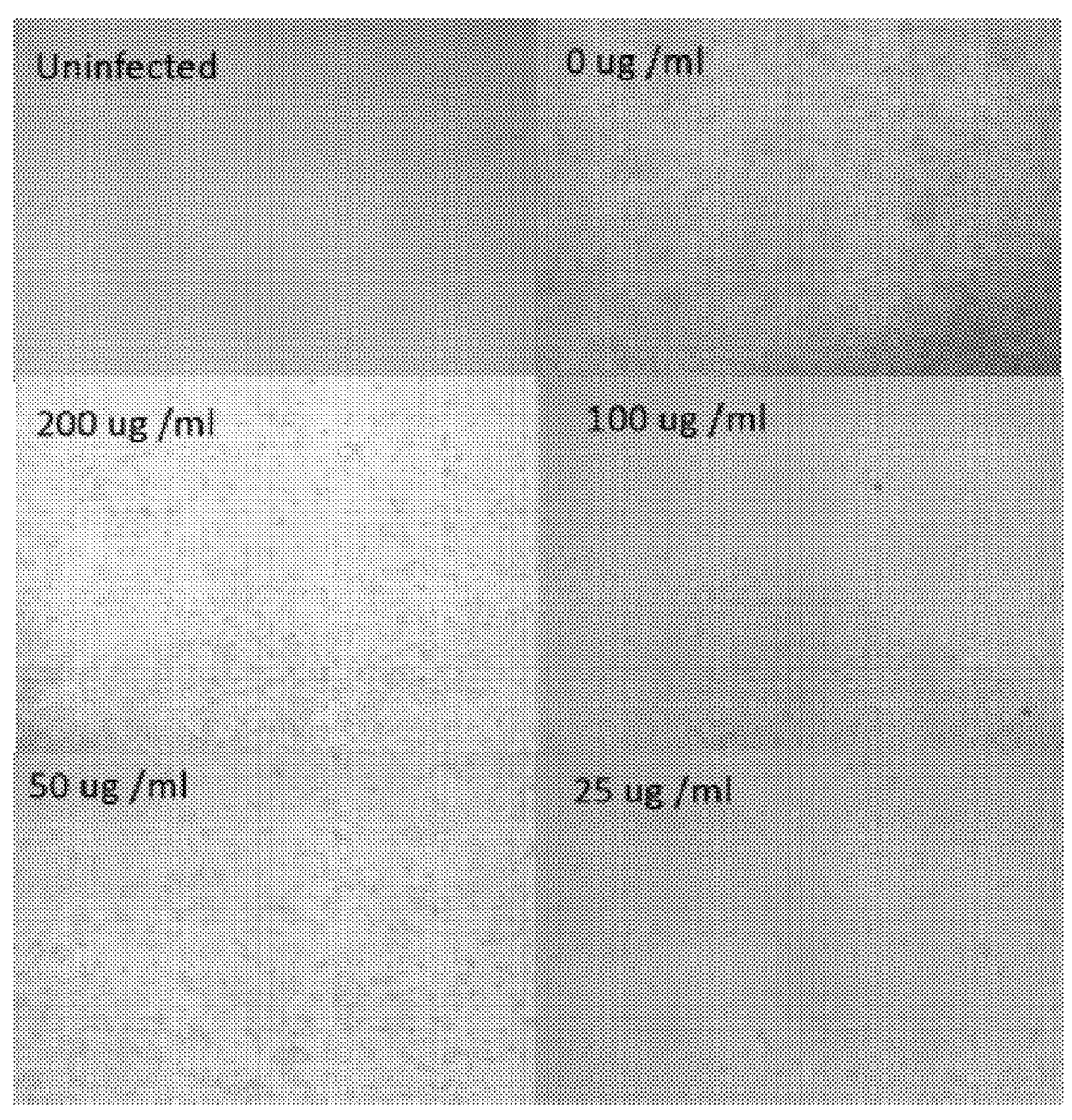
FIG. 10 illustrates effectiveness of various concentrations of Equivir at various concentrations for over 2 hours.
Figure 11:
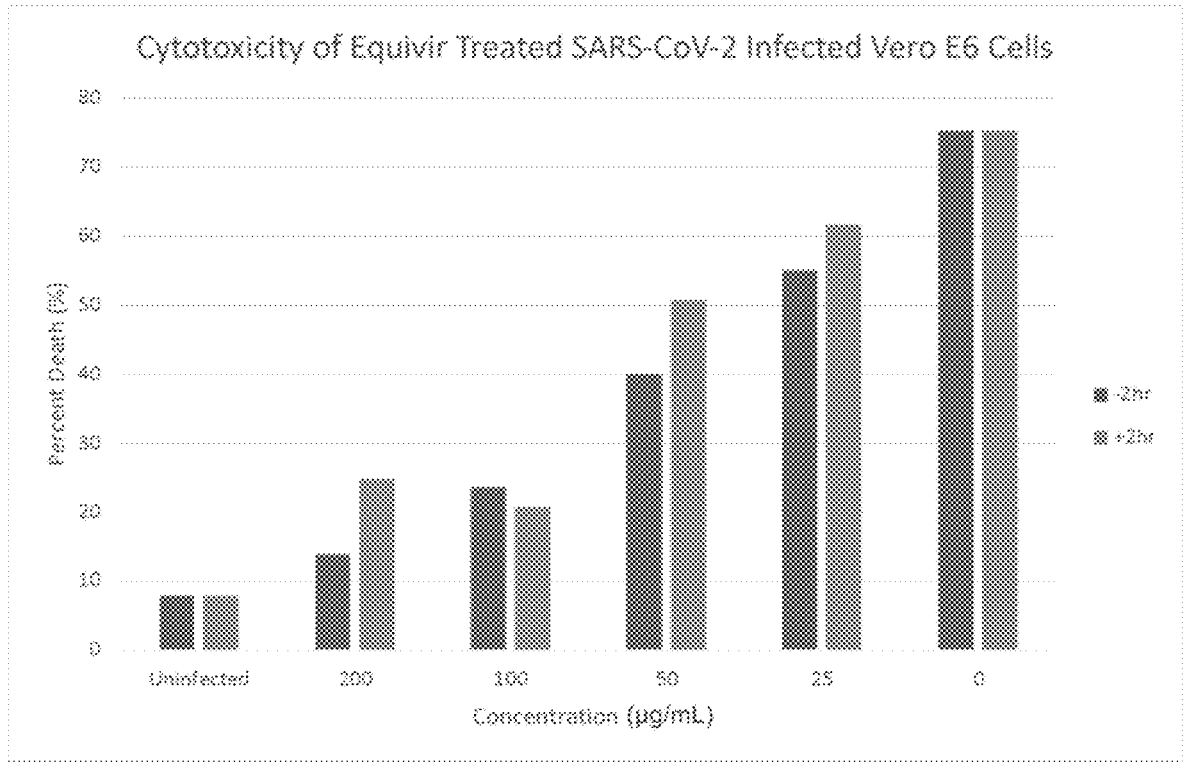
FIG. 11 is a graph comparing percent cell death versus Equivir concentration at under 2 hours and over 2 hours.

Summary of the Results:

Referring to FIGS. 9-11, effectiveness of Equivir against SARS-CoV-2 were tested by treating Vero E6 cells with various compounds added before and after infection with a MOI of 0.01. Equivir was not toxic at tested concentrations.

Equivir was effective in inhibiting viral replication at non-toxic concentrations of 200 and 100 µg/ml.

TABLE 4

|  | 200 µg/ml | 100 µg/ml | 50 µg/ml | 25 µg/ml |
|---|---|---|---|---|
| Effectiveness of Equivir at Various Concentrations | Effective | Effective | Not Effective | Not Effective |
| Equivir | Effective | Effective | Not Effective | Not Effective |

Study #4

Overall Summary of Studies:

Equivir is not toxic to Vero E6 cells below 250 µg/ml concentration.

Equivir is effective in inhibiting SARS-CoV-2 at a MOI of 0.01 in Vero E6 cells at doses ranging from 50 to 250 µg/ml when the virus and drug is added at the same time.

Equivir is effective in inhibiting SARS-CoV-2 at a MOI of 0.01 in Vero E6 cells at doses ranging from 100 to 200 µg/ml when the drug is added either 2 hours before or after the virus.

Experimental Goal of Studies 5-9

Goal:

To determine the efficacy of Equivir against SARS-CoV-2.

Brief Summary of Work:

Calu-3 (human lung adenocarcinoma cell line) cells infected with SARS-CoV-2 (WA1/USA-2020) will be treated with various concentrations of Equivir and the effectiveness of the drug will be determined by TCID50, qRT-PCR, and NP protein immunohistochemistry.

Specific Experiments:

A. Determination of Effectiveness of Equivir Against SARS-CoV-2:

1. Calu-3 cells will be grown in 24-well plate.

2. Cells will be infected with SARS-CoV-2 (WA1/USA-2020) at 0.05 MOI.

3. Cells will be treated with Equivir at concentrations of 25, 50, 100, 150, and 200 µg/ml at −2, 0, and +2 hours post-infection.

4. Health of cells will be monitored for 72 hours.

5. Supernatants from three wells will be used for estimation of viral growth by TCID50 assay at 48 hours under all conditions (four Equivir concentrations and three treatment periods).

6. Supernatants from three wells will be used for estimation of viral growth by qRT-PCR assay at 72 hours under all conditions (four Equivir concentrations and three treatment periods).

7. Three wells of Infected cells (at 48 hours post-infection with four different concentration of Equivir and three treatment conditions) will be fixed and stained with fluorescent labelled anti-NP antibody and imaged using fluorescent microscope.

8. The data from each assay will be compared with infected but not treated and treated but not infected cells.

9. Cell death will be measured by LDH release assay at 48-hour post-infection in all conditions.

B. Determination of Effectiveness of Equivir Against SARS-CoV-2:

10. Calu-3 cells will be grown in 24-well plate.

11. Cells will be infected with SARS-CoV-2 (WA1/USA-2020) at 0.05 MOI.

12. Cells will be treated with Equivir at concentrations of 50, 100, 200, and 250 µg/ml with 10% W/v gallic acid at −2, 0, and +2 hours post-infection.

13. Health of cells will be monitored for 72 hours.

14. Supernatants from three wells will be used for estimation of viral growth by TCID50 assay at 48 hours under all conditions (four Equivir concentrations and three treatment periods).

15. Supernatants from three wells will be used for estimation of viral growth by qRT-PCR assay at 48 hours under all conditions (four Equivir concentrations and three treatment periods).

16. Three wells of Infected cells (at 48 hours post-infection with four different concentration of Equivir and three treatment conditions) will be fixed and stained with fluorescent labelled anti-NP antibody and imaged using fluorescent microscope.

17. The data from each assay will be compared with infected but not treated and treated but not infected cells.

Deliverables:

1) TCID50 values at 48 hours following infection and treatment with Equivir.

2) Viral titers by q-RT-PCRT at 72 hours following infection and treatment with Equivir.

3) At least 3 images (40×) of fluorescent anti-NP staining of cells under each condition along with appropriate controls.

SARS-CoV-2 Infection Assay/$TCID_{50}$ General Protocol—MJN—Adapted from Sutton Lab:

1. Prepare stock solution at 20 mg/mL in DMSO. Aliquot and store at −20° C.

2. Seed designated cell type in either 24- or 96-well plate 24 hr prior to infection. Place in $CO_2$ incubator at 37° C.

3. On day of infection, prepare compound working solutions to specified concentrations and dilute viral stock for targeted MOI.

4. Add virus suspension, treatment, or combination of the two as necessary to individual wells at either −2 hr, 0 hr, or +2 hr timepoints.

5. Incubate virus with cells for 1 hr at 37° C., and then aspirate virus suspension.

6. Replace with treatment compound or plain media, and incubate cells for predetermined time.

7. Following incubation, collect supernatant from each well and spin down to purify.

8. For 24-well $TCID_{50}$, seed plated with Vero E6 cells 24 hr prior to assay. Place in $CO_2$ incubator at 37° C.

9. Serially dilute stock concentrations at 1:10 out to $10^{-10}$.

10. Aspirate old media from Vero E6 cells and add 900 µl/well of fresh media with 2% FBS.

11. Starting with the most dilute supernatant sample ($10^{-10}$), add 100 µl of each sample to four pre-labeled Vero E6 wells. Continue adding 100 µl of each sample to corresponding wells, working from the most dilute to the most concentrated samples.

12. Make sure to have untreated wells for negative controls.

13. Incubate at 37° C. for 72 hrs before reading cytopathic effects and calculating $TCID_{50}$ values.

SARS-CoV-2 qRT-PCR Protocol—MJN:

1. Isolate RNA from cells or tissue using a previously described protocol combining TRIzol and the Invitrogen PureLink RNA Mini Kit.

2. Confirm viral inactivation of samples via previously described protocols before taking processed RNA samples to BSL2 facility.

3. Nanodrop RNA samples for quality check and concentration values.

4. Normalize RNA concentrations across samples.

5. Generate cDNA with BioRad iScript cDNA Kit and dilute final product at 1:20 in RNase free water.

6. Perform qPCR for SARS-CoV-2 N2 protein using BioRad CFX Connect system. Add 5 μl of diluted cDNA of each sample to respective volumes of BioRad SsoAdvanced Universal SYBR Green SuperMix, IDT nCOV_N2 (SUN) Probe, and water. Include pre-calculated positive control samples.

Obtain quantification or threshold cycle value through CFX Manager™ Software, and calculate gene copy number based on the standard.

SARS-CoV-2 IFA Assay Protocol—MJN—adapted from Jose Lab:

1. Seed cells in 24-well plates with glass coverslips in the bottom of each well.

2. Perform infection assay with SARS-CoV-2 and incubate for 48-72 hrs.

3. Gently wash the infected cells with phosphate-buffered saline (PBS) three times before fixing.

4. Fix the cells using 3.7% paraformaldehyde (500 ul/well) in PBS for 30 min at room temperature.

5. Wash 3× in PBS (1 ml/well).

6. Permeabilize the cells using 0.1% Triton X-100 in PBS (500 μl/well) for 15 min.

7. 250 μl of Triton X-100 to 24.75 ml of 1×PBX to make 25 ml of 25 ml of 0.1% Triton X-100.

8. Wash 3× in PBS (1 ml/well) each 3 min.

9. Confirm viral inactivation of the plate via previously described protocols before taking fixed cells to BSL2 facility.—Keep plate at 4° C.

10. Blocking: 1 hr to overnight at 4° C. with PBS+10 mg/mL bovine serum albumin (500 ul/well).

11. Remove the blocking solution. Add 50 μl of Primary antibody for 1 hr (diluted in PBS+ with 10 mg/mL bovine serum. Rock on the rocker at room temperature for one hour.

12. Remove the solution, Wash 3× in PBS (500 μl/well).

13. From here, do all experiments under dark condition. Cover the plate using aluminum foil and turn off the lights in the hood. Incubate with 50 μl secondary antibody in PBS+10 mg/mL bovine serum. Rock on the rocker at room temperature for 1 hr.

14. Stain the nuclei using Hoechst stain (0.2 to 2 μg/mL) in PBS for 15 min.

15. Wash 3× in PBS (500 μl/well) each 3 min. Leave PBS on well plate.

16. Mount the cover slides onto glass slides with one drop of Fluorsave and use transparent nail polish to seal the slides.

17. Store in the dark at 4° C. until ready to image.

Study #5

Objective:

To determine the toxicity of Equivir on Calu-3 cells.

Experimental Overview:

Calu-3 cells (purchased from ATCC) were seeded at a density of 1.55 cells/well in 24-well plates. Equivir was added at final concentrations of 200, 150, 100, 50, 25, and 0 μg/ml. Each concentration was tested in triplicate wells. Wells were monitored daily, and an LDH cytotoxicity assay was completed on D2 and the final day of the experiment (D3).

Concentrations of Equivir Tested:

Equivir (μg/ml): 200, 150, 100, 50, 25 and 0.

Figure 12:
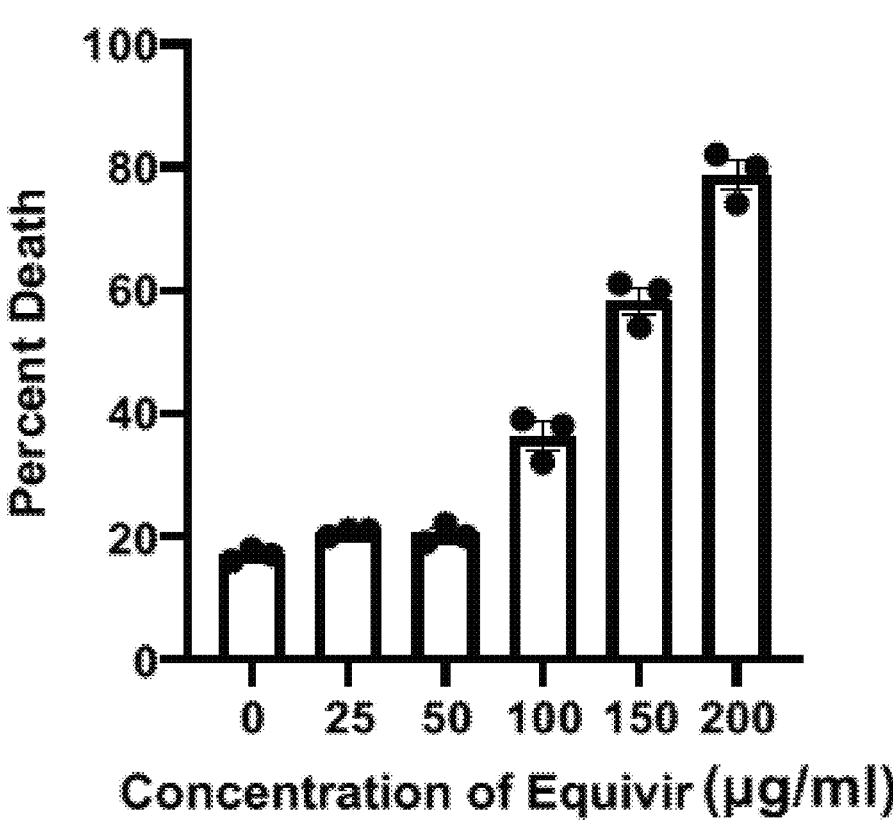
FIG. 12 is a graph showing percent cell death versus concentration of Equivir.
Figure 13:
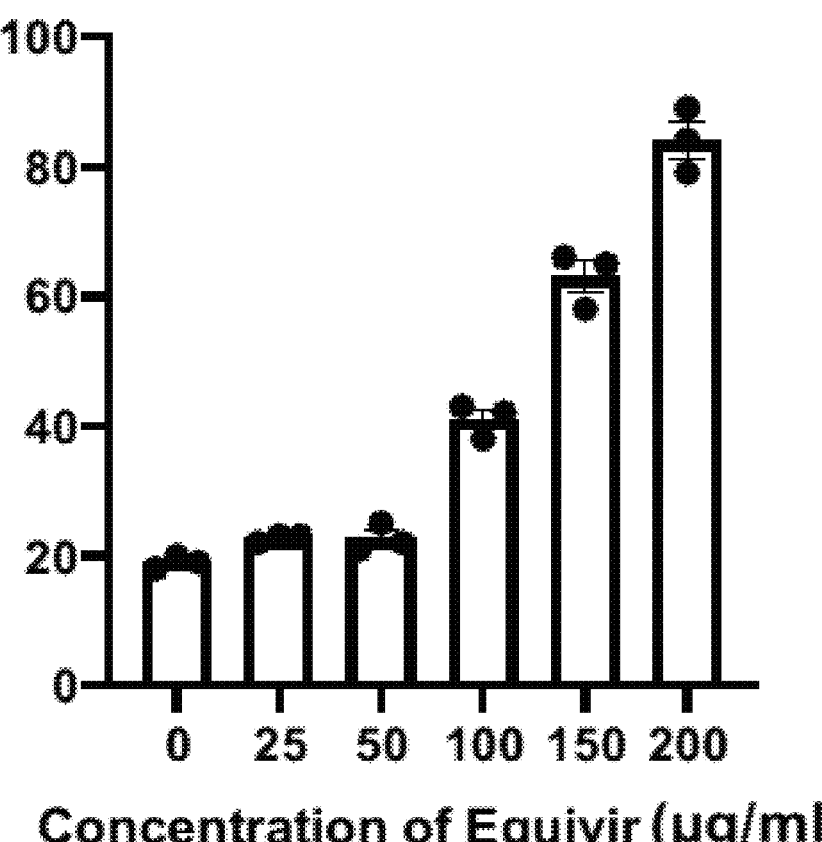
FIG. 13 is a graph showing percent cell death versus concentration of Equivir.
Figure 15A:
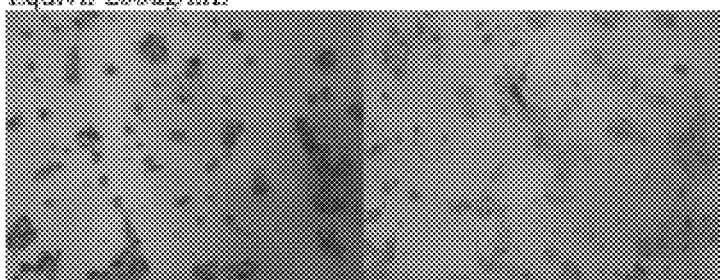
FIG. 15a are images of infected cells with Equivir 200 μg/ml.
Figure 15B:
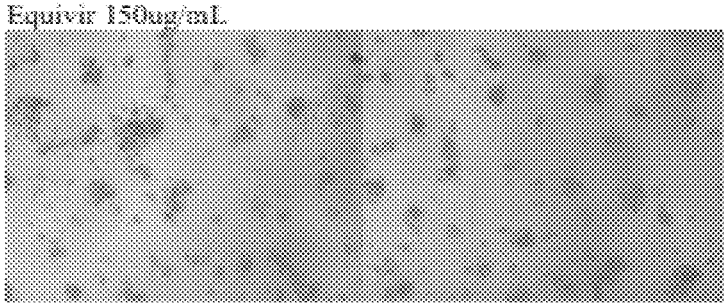
FIG. 15b are images of infected cells with Equivir 150 μg/ml.
Figure 15C:
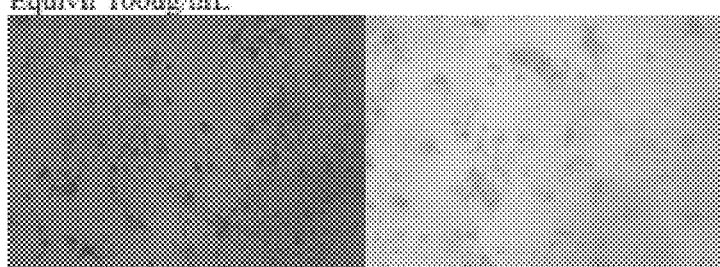
FIG. 15c are images of infected cells with Equivir 100 μg/ml.
Figure 15D:
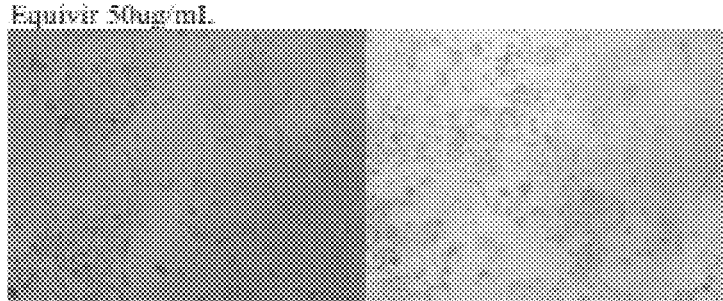
FIG. 15d are images of infected cells with Equivir 50 μg/ml.
Figure 15E:
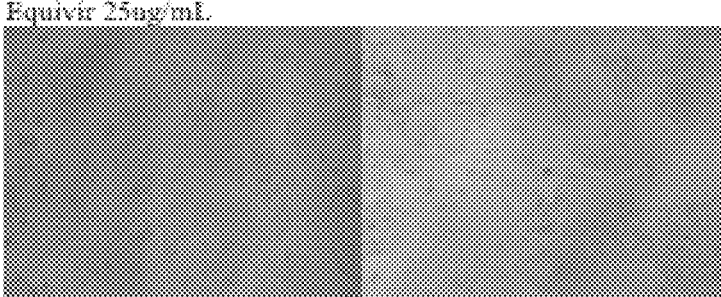
FIG. 15e are images of infected cells with Equivir 25 μg/ml.
Figure 16:
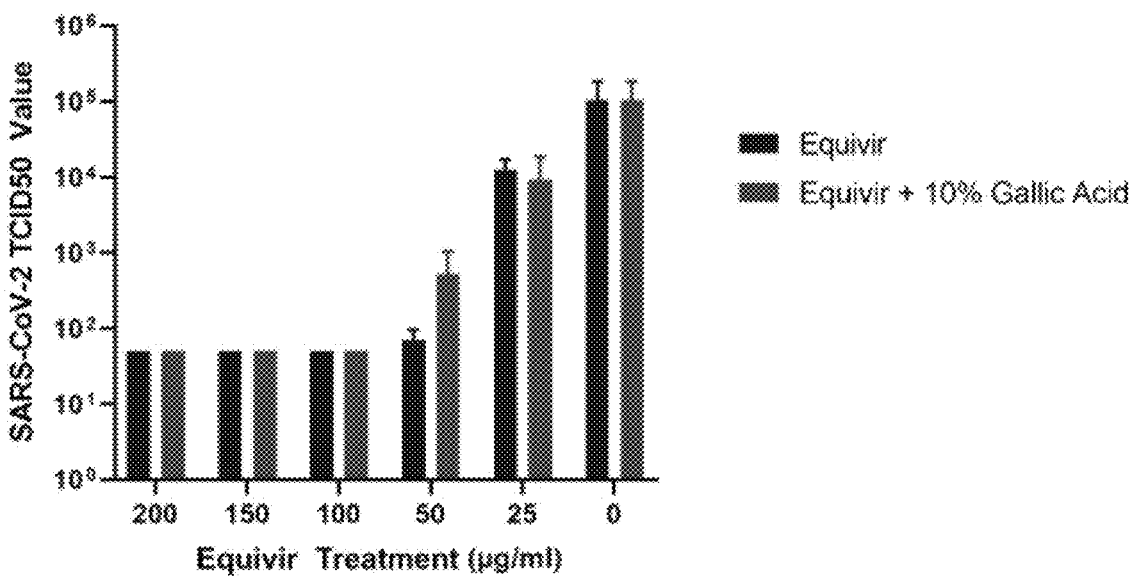
FIG. 16 is a graph of SARS-CoV-2 versus Equivir treatment.
Figure 17:
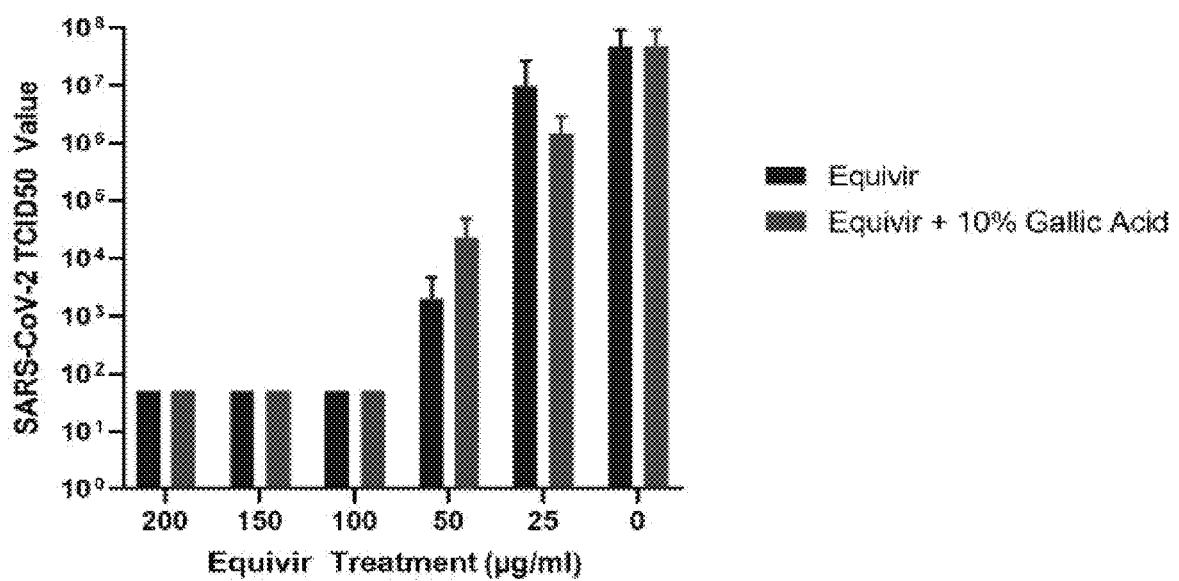
FIG. 17 is a graph showing SARS-CoV-2 versus Equivir concentration.
Figure 18A:
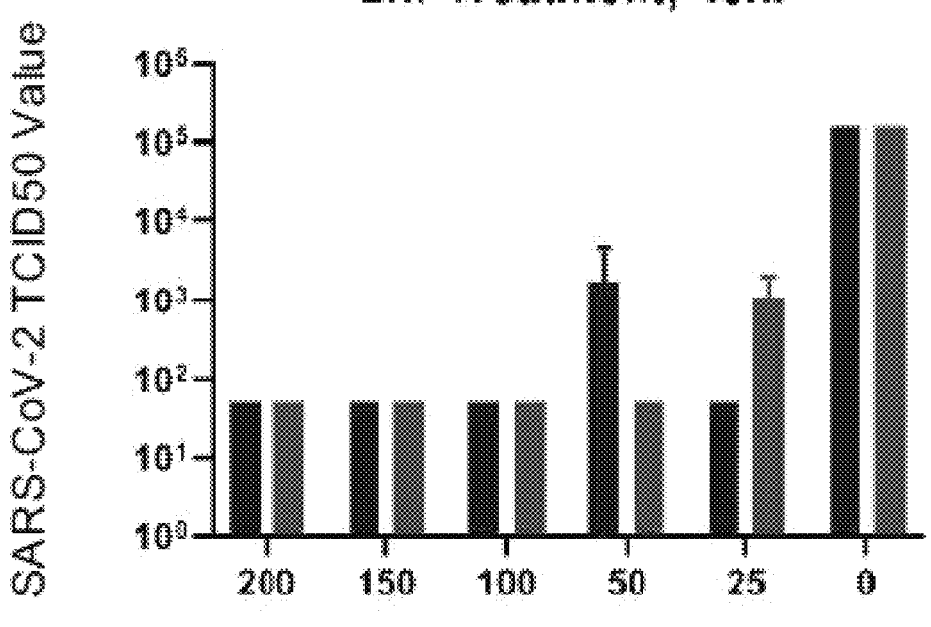
FIGS. 18a and 18b are graphs showing SARS-CoV-2 with Equivir treatment less than 2 hours at 48 hours and 72 hours, respectively.
Figure 18B:
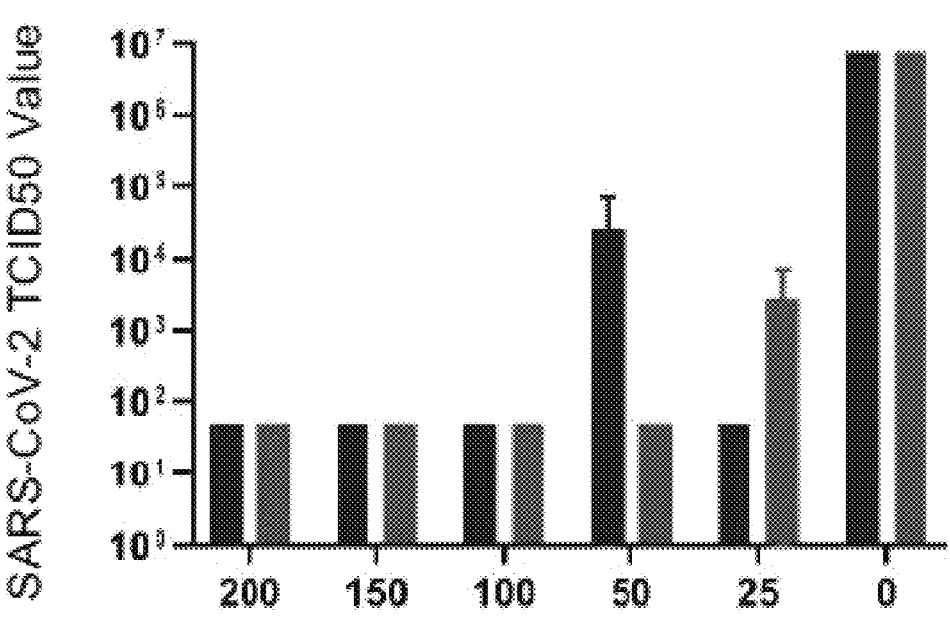
Figure 19A:
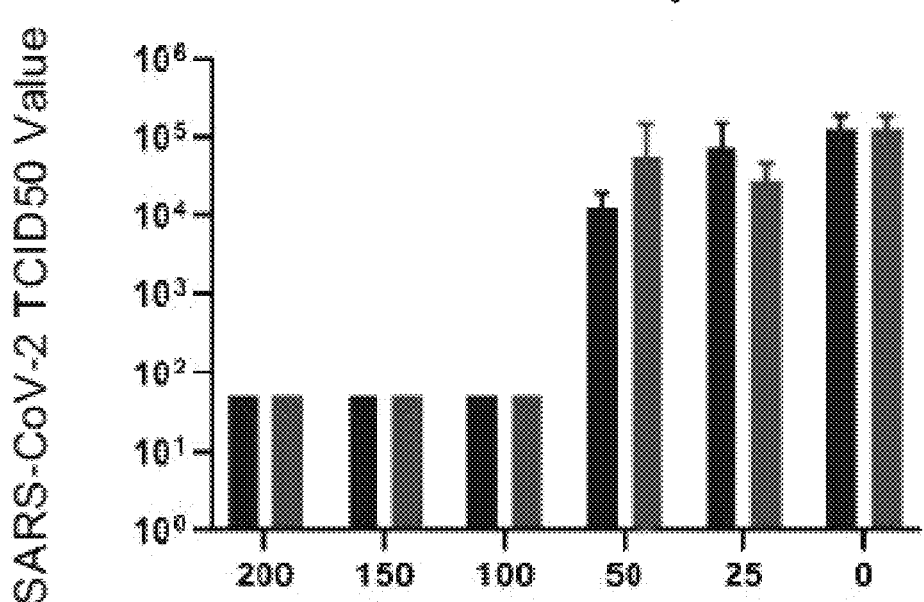
FIGS. 19a and 19b are graphs showing SARS-CoV-2 with Equivir treatment at more than 2 hours at 48 hours and 72 hours, respectively.
Figure 19B:
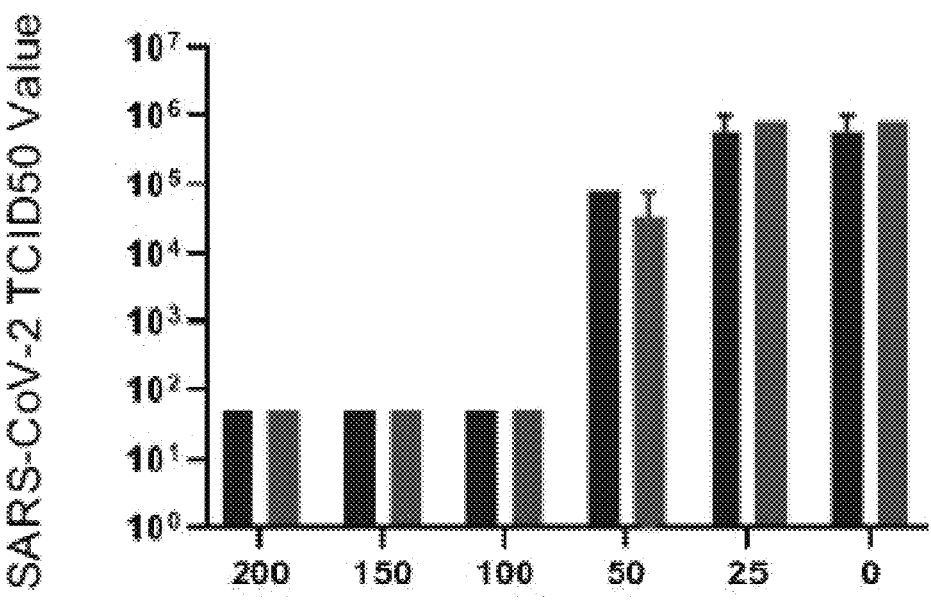
Figure 20:
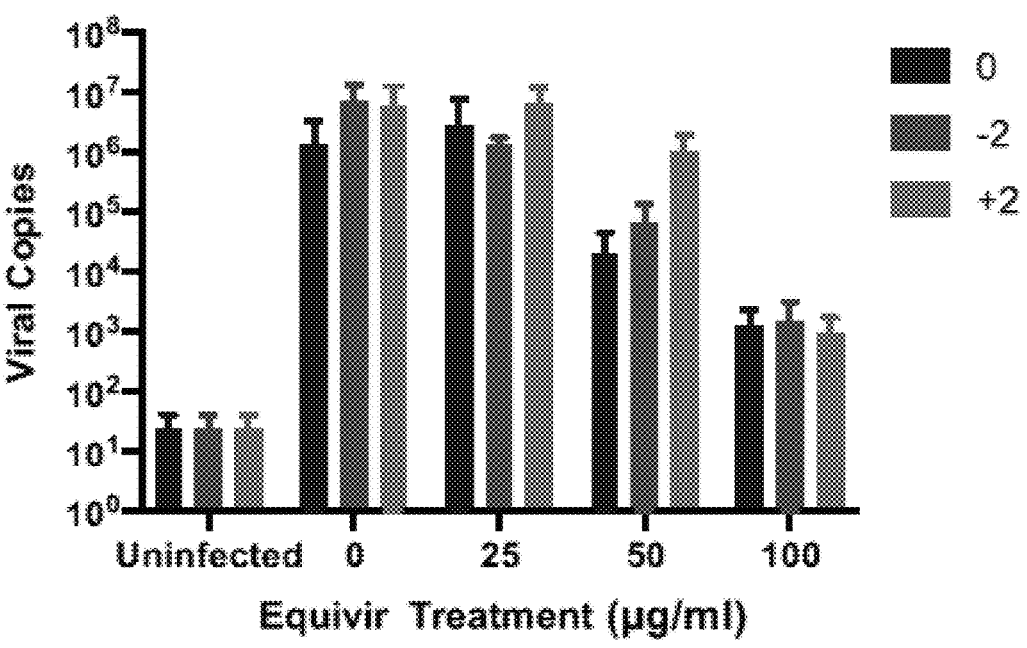
FIG. 20 is a graph showing viral copies versus Equivir.
Figure 21:
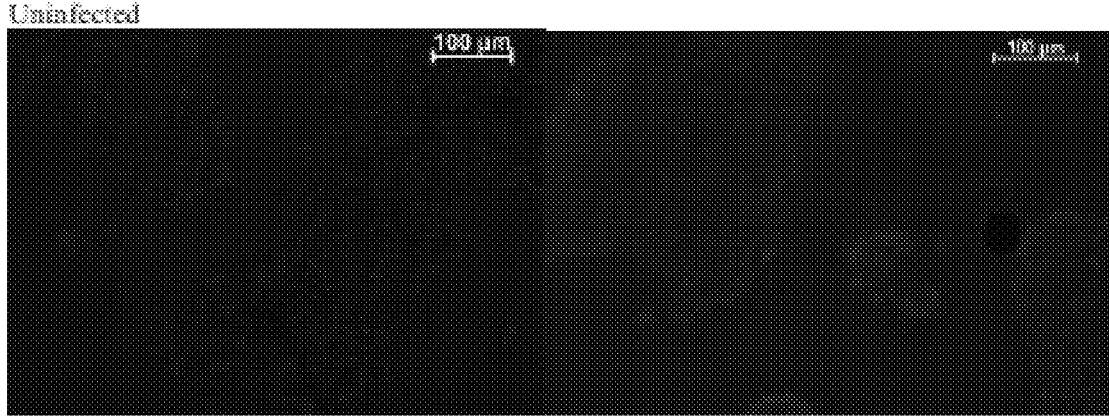
FIG. 21 is a photograph showing uninfected cells.
Figure 22:
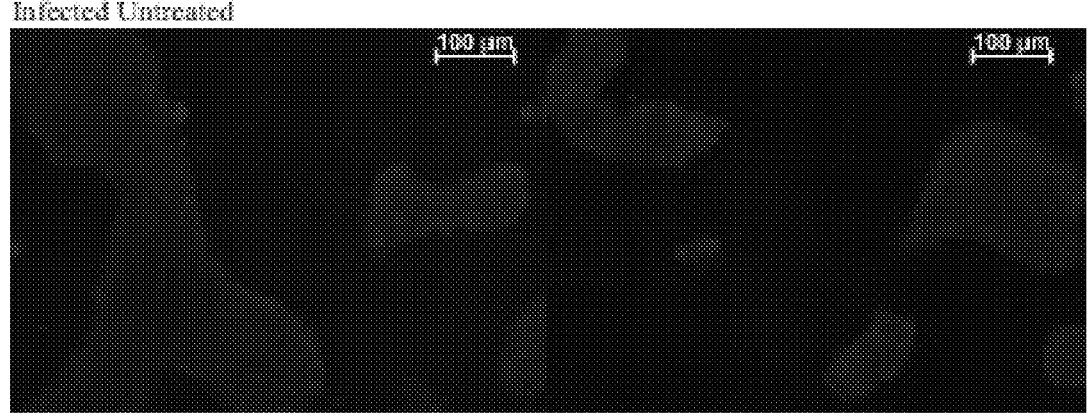
FIG. 22 is a photograph showing infected untreated cells.
Figure 23:
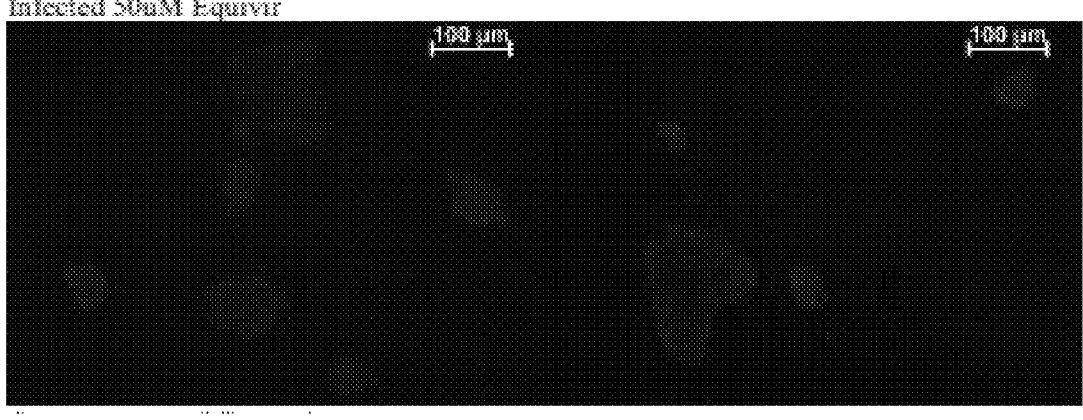
FIG. 23 is a photograph showing infected cells with 50 μM Equivir.
Figure 24:
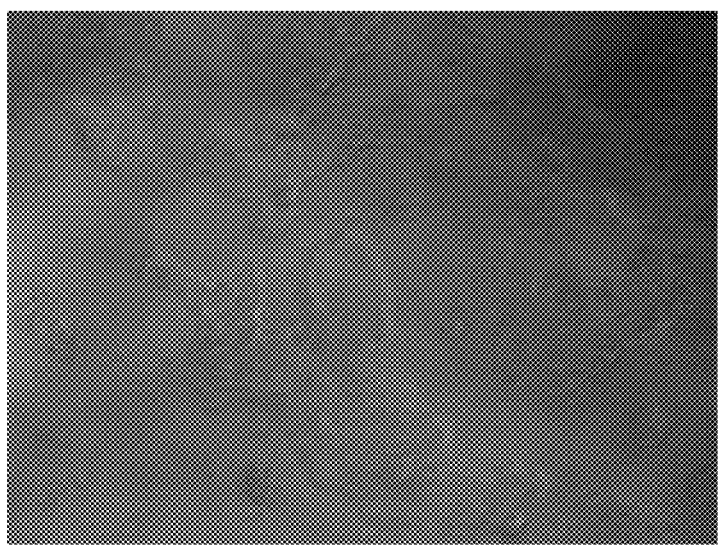
FIG. 24 is an image of Calu-3 from untreated cells.
Figure 25:
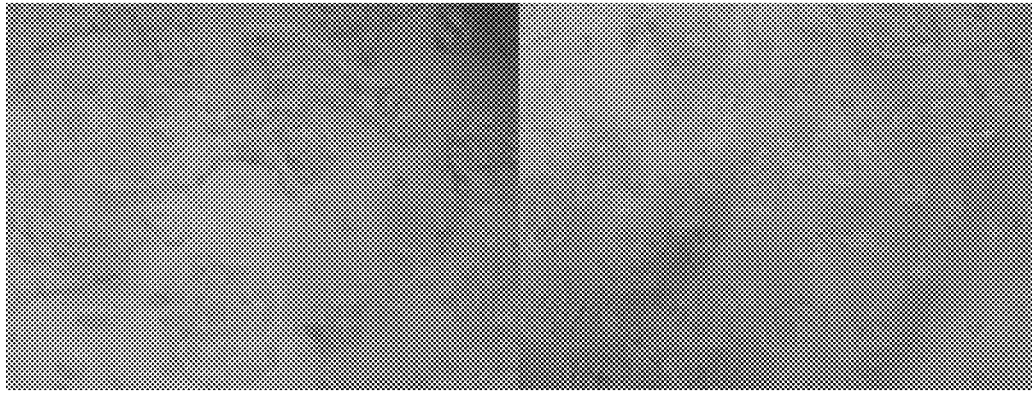
FIG. 25 are images of uninfected cells added to cells 2 hours prior to infection with SARS-CoV-2.
Figure 26:
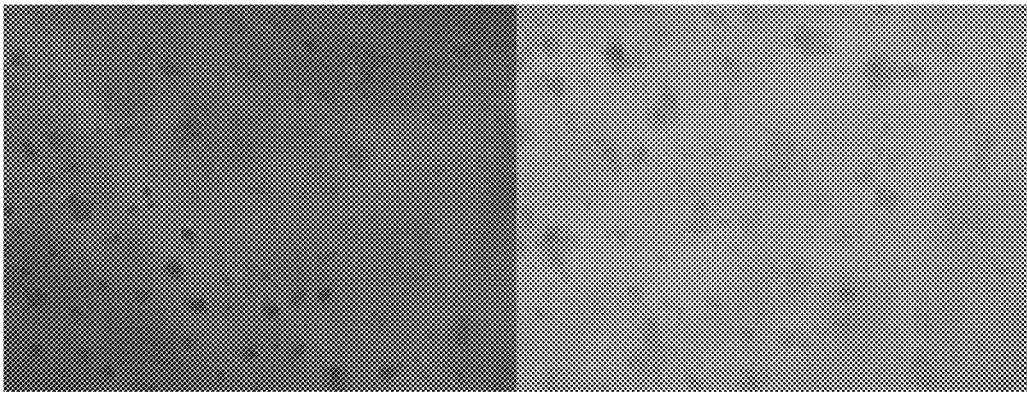
FIG. 26 are images of infected cells with Equivir at 200 μg/ml, added to cells 2 hours prior to infection with SARS-CoV-2.
Figure 27:
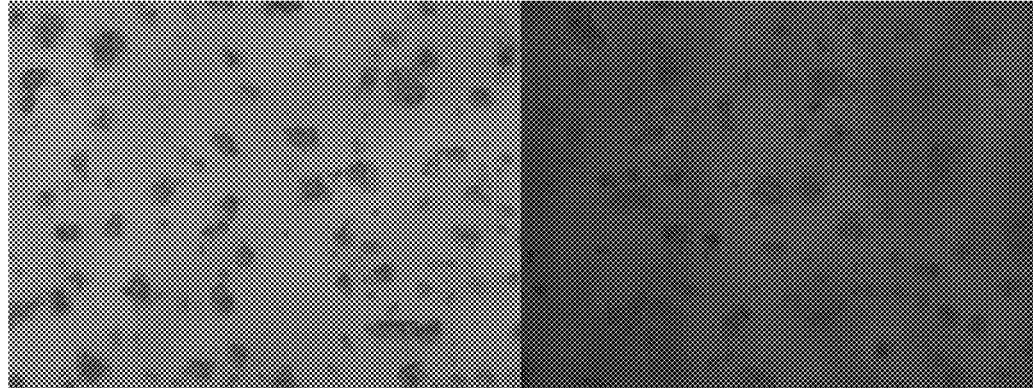
FIG. 27 are images of infected cells with Equivir at 150 μg/ml, added to cells 2 hours prior to infection with SARS-CoV-2.
Figure 28:
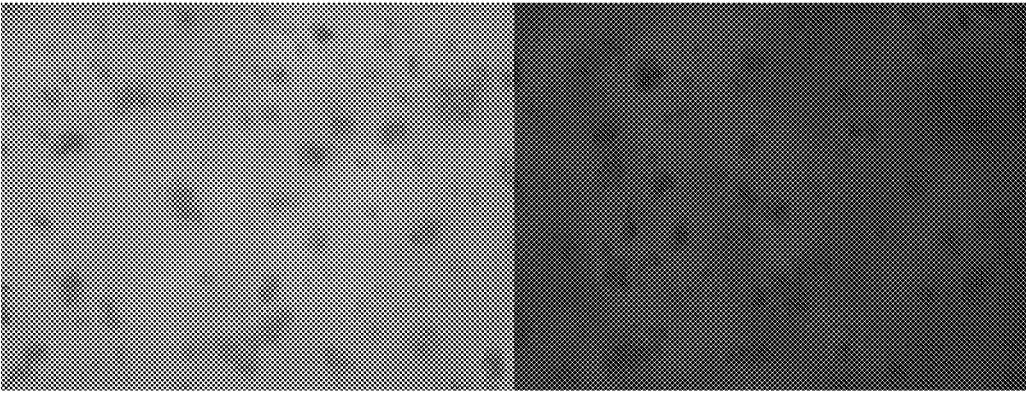
FIG. 28 are images of infected cells with Equivir at 100 μg/ml, added to cells 2 hours prior to infection with SARS-CoV-2.
Figure 29:
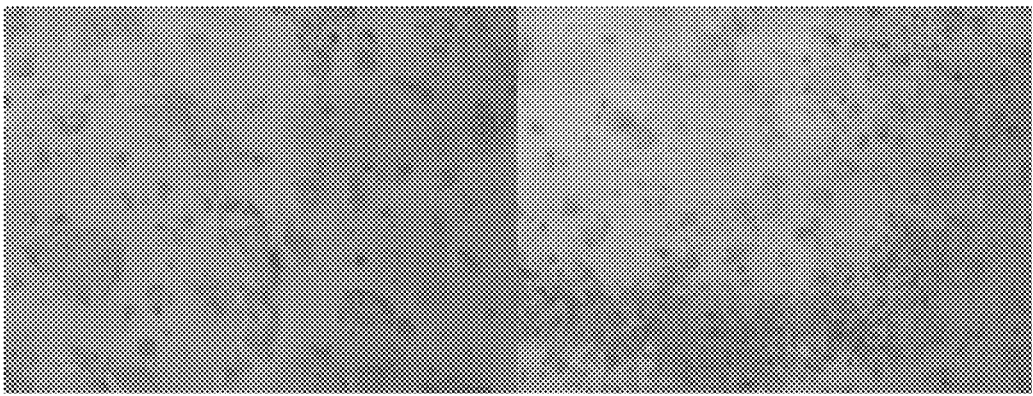
FIG. 29 are images of infected cells with Equivir at 50 μg/ml, added to cells 2 hours prior to infection with SARS-CoV-2.
Figure 30:
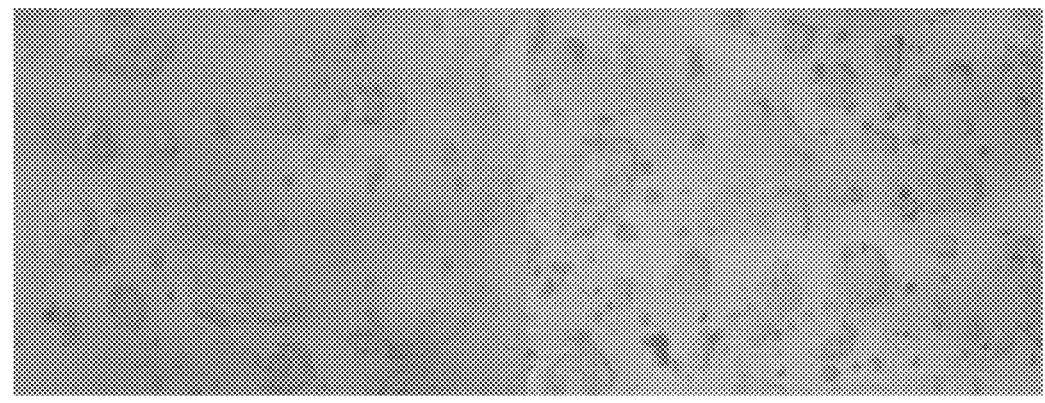
FIG. 30 are images of infected cells with Equivir at 25 μg/ml, added to cells 2 hours prior to infection with SARS-CoV-2.
Figure 31:
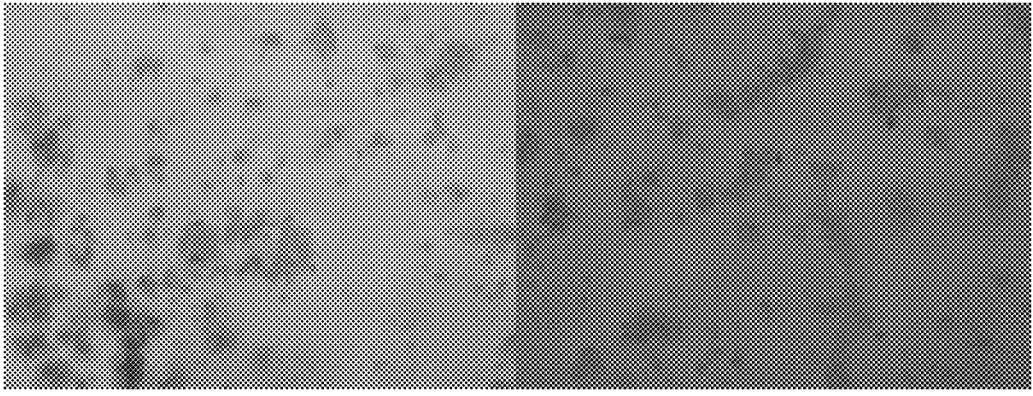
FIG. 31 are images of Equivir 200 μg/ml and gallic acid 20 μg/ml, added to cells 2 hours prior to infection with SARS-CoV-2.
Figure 32:
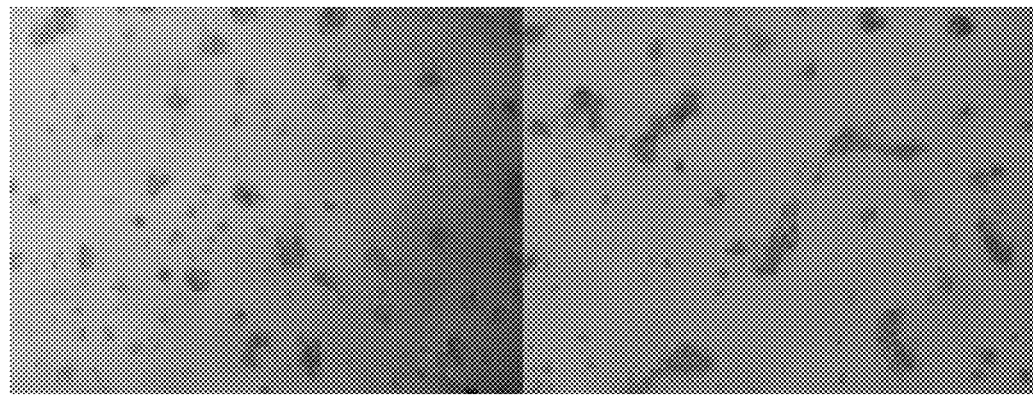
FIG. 32 are images of Equivir 150 μg/ml and gallic acid 15 μg/ml, added to cells 2 hours prior to infection with SARS-CoV-2.
Figure 33:
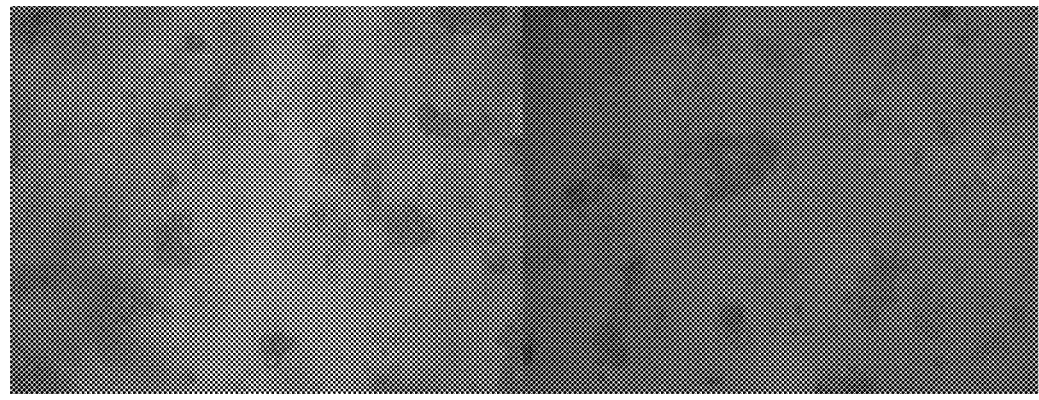
FIG. 33 are images of Equivir 100 μg/ml and gallic acid 10 μg/ml, added to cells 2 hours prior to infection with SARS-CoV-2.
Figure 34:
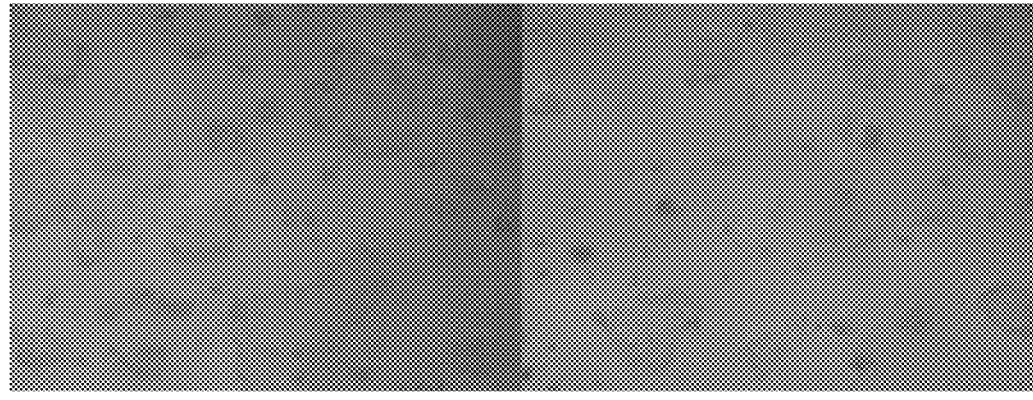
FIG. 34 are images of Equivir 50 μg/ml and gallic acid 5 μg/ml, added to cells 2 hours prior to infection with SARS-CoV-2.
Figure 35:
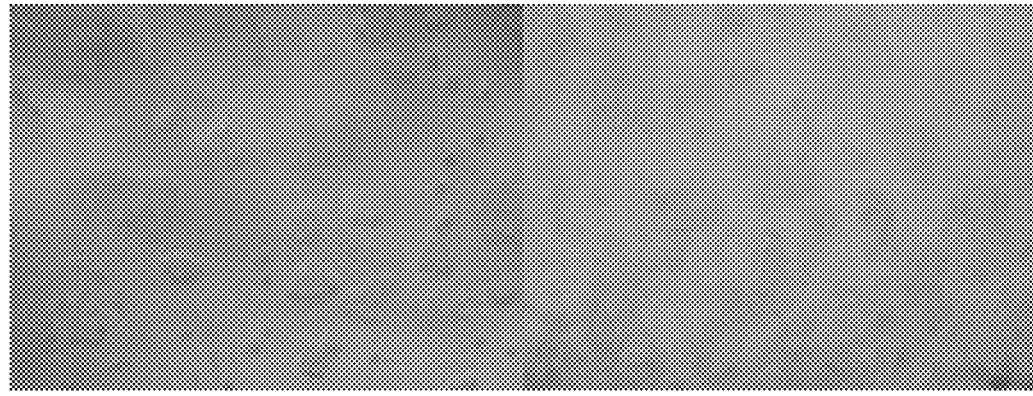
FIG. 35 are images of Equivir 25 μg/ml and gallic acid 2.5 μg/ml, added to cells 2 hours prior to infection with SARS-CoV-2.
Figure 36:
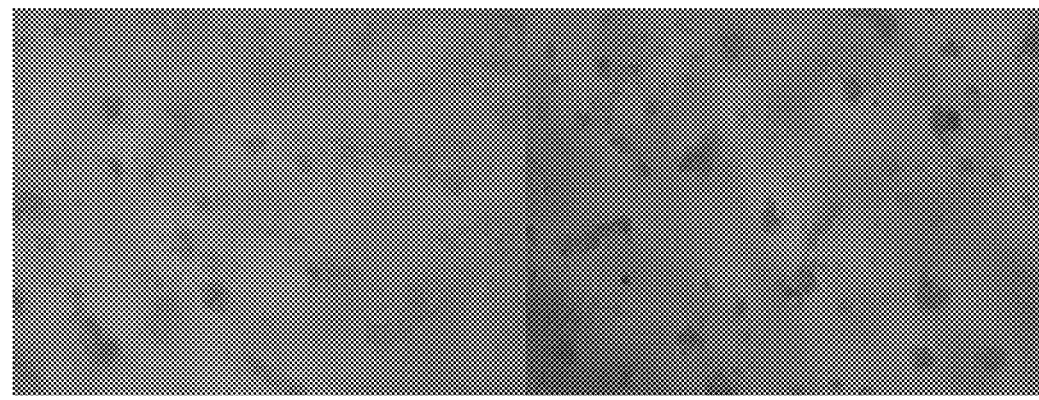
FIG. 36 are images of Equivir 200 μg/ml, added to cells 2 hours after to infection with SARS-CoV-2.
Figure 37:
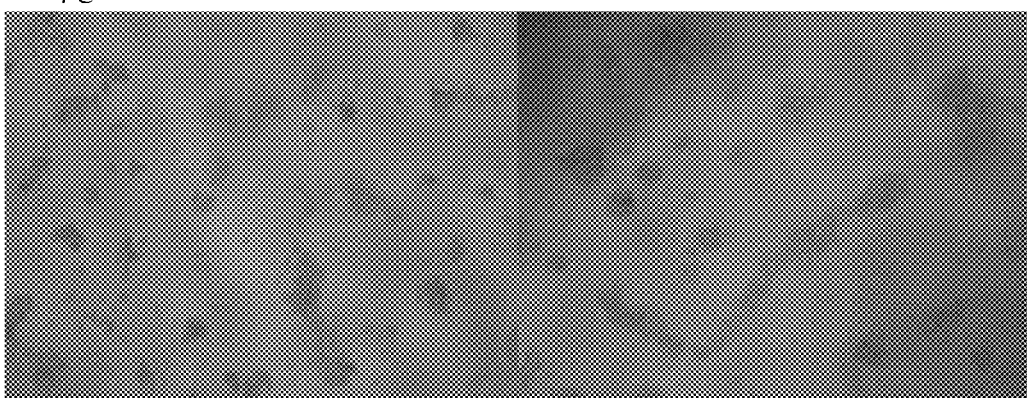
FIG. 37 are images of Equivir 150 μg/ml, added to cells 2 hours after to infection with SARS-CoV-2.
Figure 38:
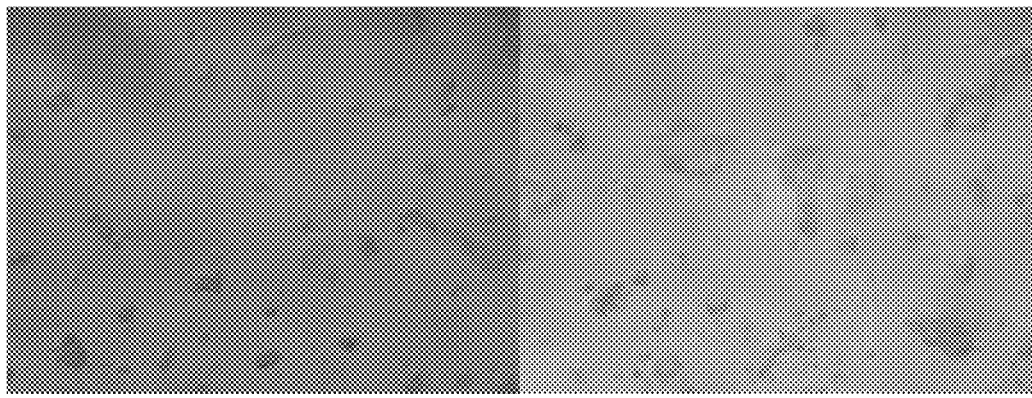
FIG. 38 are images of Equivir 100 μg/ml, added to cells 2 hours after to infection with SARS-CoV-2.
Figure 39:
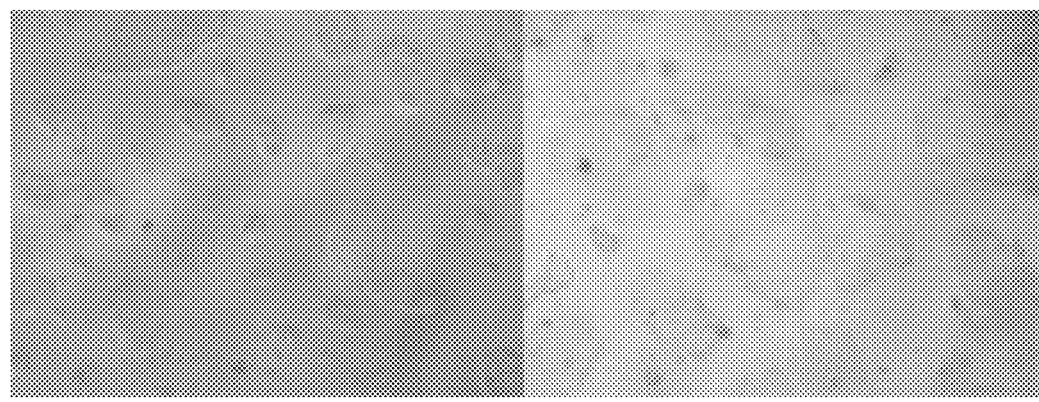
FIG. 39 are images of Equivir 50 μg/ml, added to cells 2 hours after to infection with SARS-CoV-2.
Figure 40:
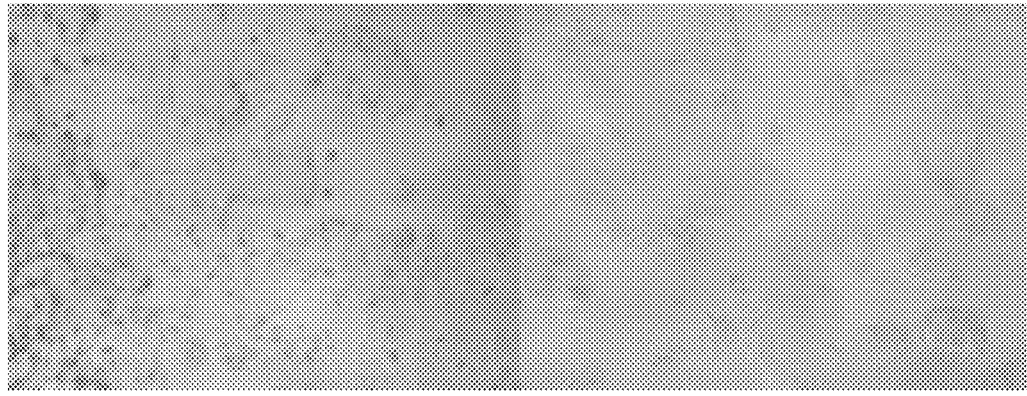
FIG. 40 are images of Equivir 25 μg/ml, added to cells 2 hours after to infection with SARS-CoV-2.
Figure 41:
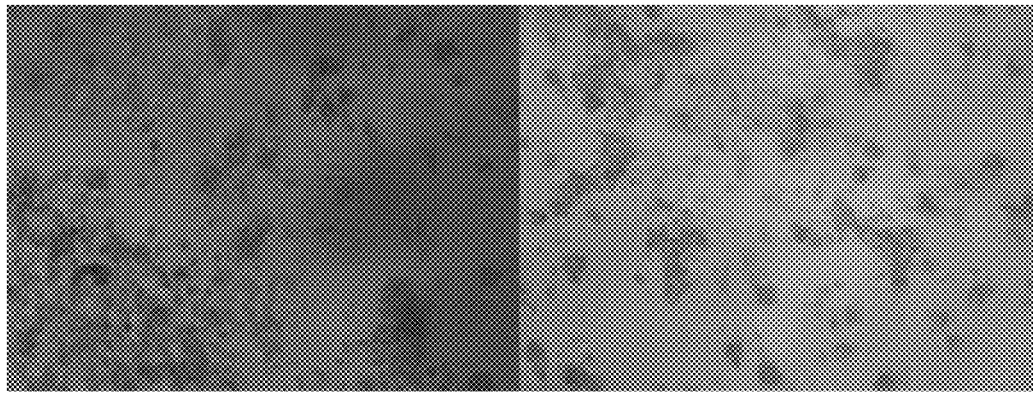
FIG. 41 are images of Equivir 200 μg/ml and gallic acid 20 μg/ml, added to cells 2 hours after to infection with SARS-CoV-2.
Figure 42:
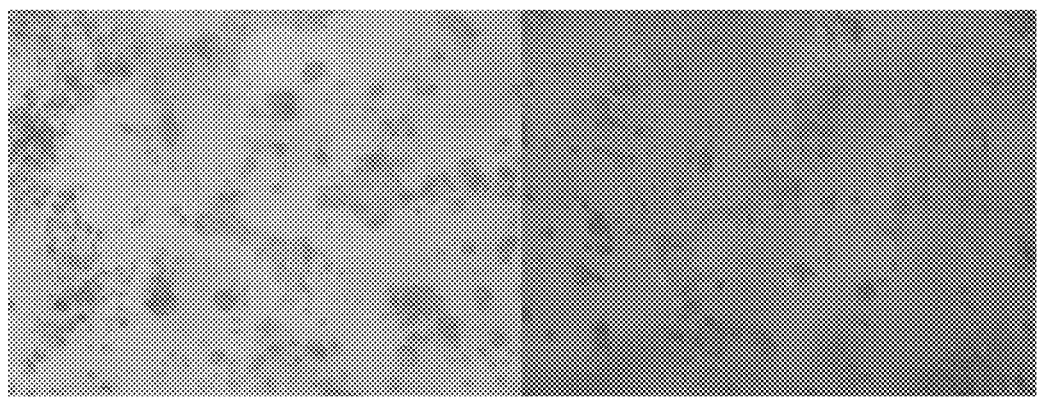
FIG. 42 are images of Equivir 150 μg/ml and gallic acid 15 μg/ml, added to cells 2 hours after to infection with SARS-CoV-2.
Figure 43:
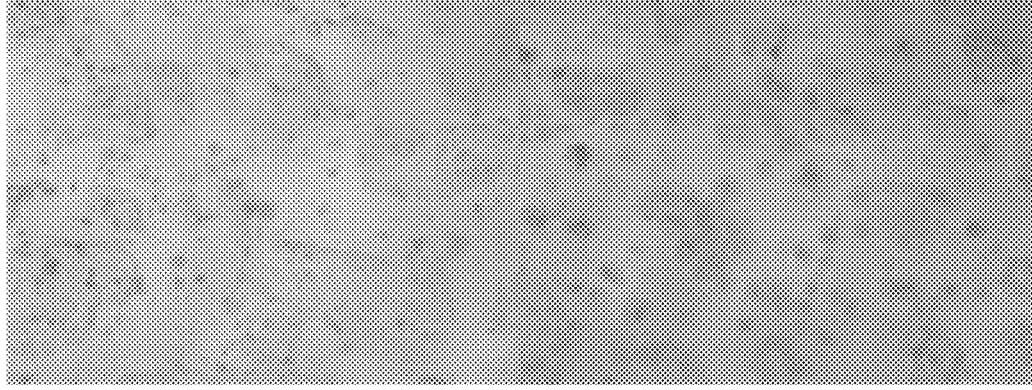
FIG. 43 are images of Equivir 100 μg/ml and gallic acid 10 μg/ml, added to cells 2 hours after to infection with SARS-CoV-2.
Figure 44:
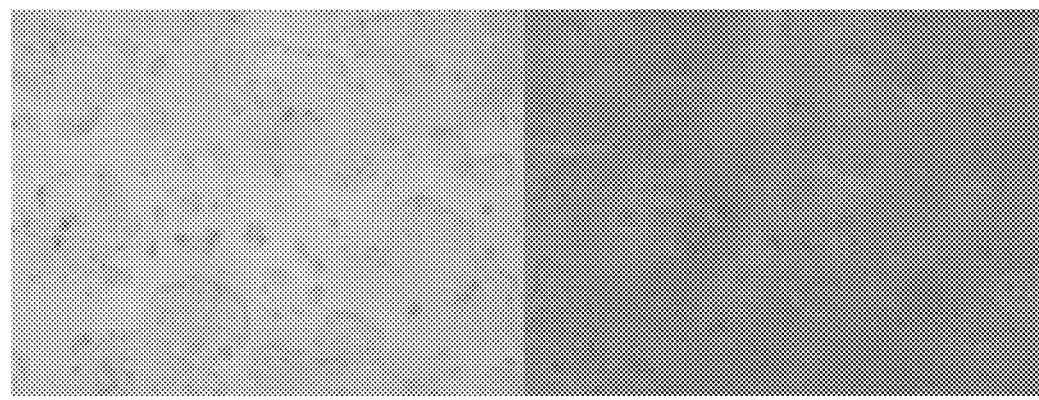
FIG. 44 are images of Equivir 50 μg/ml and gallic acid 5 μg/ml, added to cells 2 hours after to infection with SARS-CoV-2.
Figure 45:
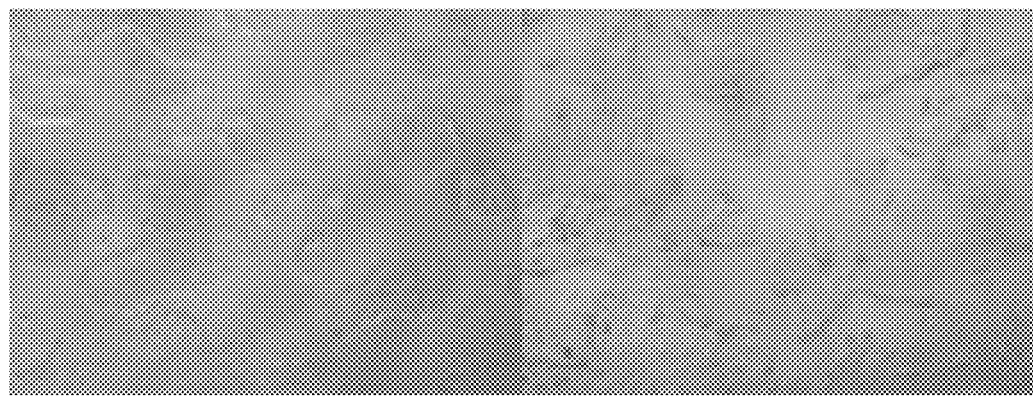
FIG. 45 are images of Equivir 25 μg/ml and gallic acid 2.5 μg/ml, added to cells 2 hours after to infection with SARS-CoV-2.
Figure 46A:
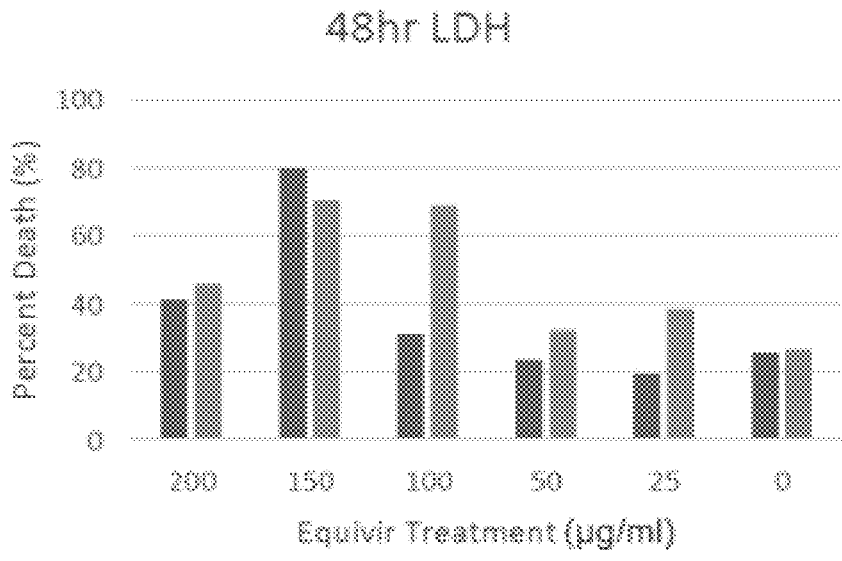
FIG. 46*a* is a graph showing percent depth versus Equivir at 48 hours.
Figure 46B:
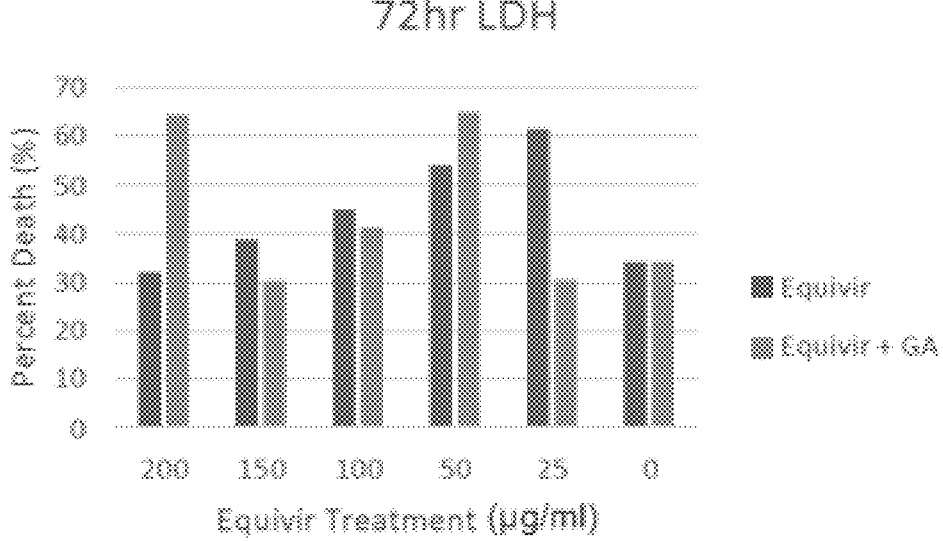
FIG. 46*b* is a graph showing percent depth versus Equivir at 72 hours.
Figure 47:
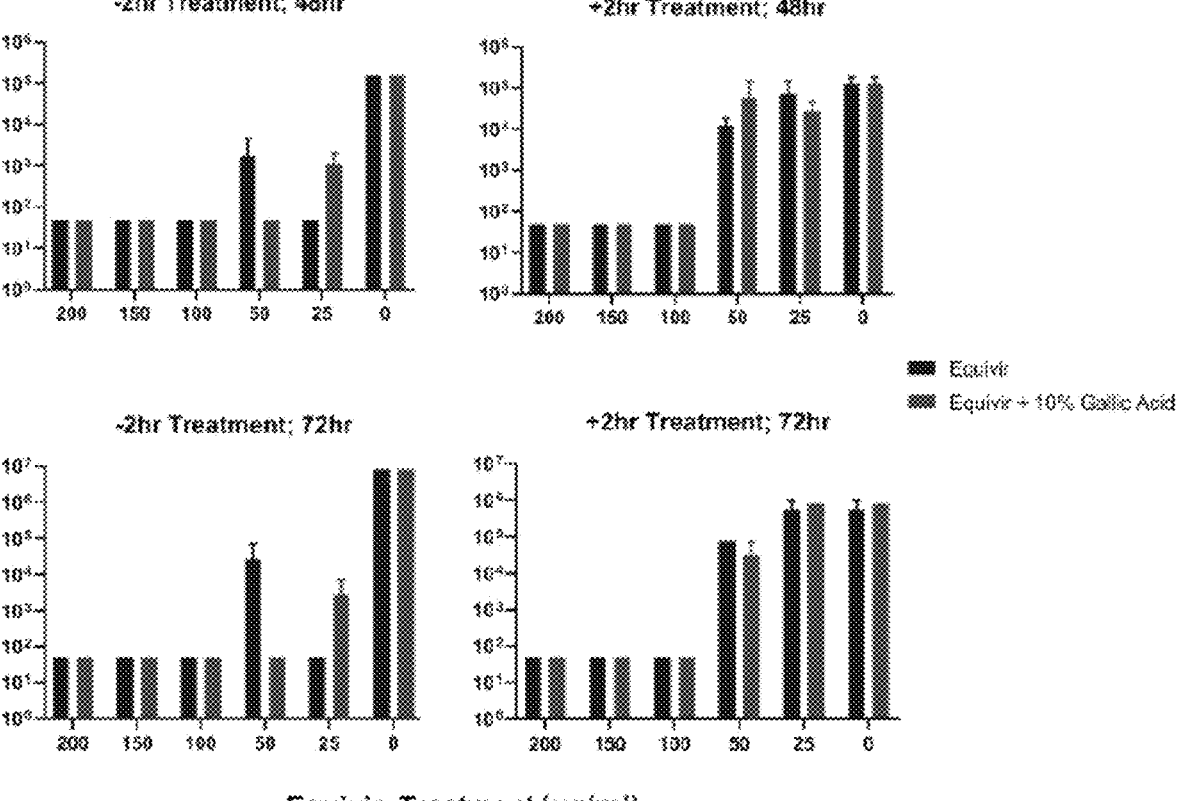
FIG. 47 includes four graphs showing SARS-CoV-2 at various concentrations and less than 2 hours or more than 2 hours for Equivir and Equivir plus 10% gallic acid.

Summary of Results:

Referring to FIGS. 12 and 13, Equivir was toxic (above the control group) to Calu-3 cells at 100 μg/ml and above concentrations at 48- and 72-hours post-treatment.

Study #6

Objective:

To determine the effect of Equivir supplied by GRDG against SARS-CoV-2 in Calu-3 cells when the compound was added at the time infection. Results of this study are shown in FIGS. 14*a*-17.

Experimental Overview:

Calu-3 cells were seeded at a density of $5\times10^5$ cells/well in 24-well plates. Five dilutions of Equivir and vehicle treatment (DMSO) were added simultaneously with SARS-CoV-2 (MOI: 0.05). Each concentration was tested in triplicate wells. After one hour, cells were washed with PBS, and Equivir was added mentioned concentrations. Equivir was maintained in the medium throughout the infection. At 48-hour post-infection, 100 μl of supernatant was removed and viral titer in the media was quantified by TCID50 assay (protocol attached as Appendix). Representative images of each concentrations on day 3 are below.

Concentrations of Equivir Tested:

Equivir (μg/ml): 200, 150, 100, 50 and 25.

Summary of Results:

Effectiveness of Equivir against SARS-CoV-2 was tested by treating Calu-3 cells with various concentrations of Equivir added at the time of infection with a MOI of 0.05. Equivir was toxic at concentrations above 100 μg/ml and not toxic at lower concentrations. Equivir was effective in inhibiting viral replication at non-toxic concentrations of 50 μg/ml. Approximately 3- to 4-log fold reduction at 48- and 72-hours post-infection was statistically significant (One-way ANOVA). Approximately one-log fold reduction in viral titers observed at 25 μg/ml (48 hours PI) was not statistically significant.

FIGS. 14*a*-17 show effectiveness.

Study #7

Objective:

To determine the effect of Equivir supplied by GRDG against SARS-CoV-2 in Calu-3 cells when the compound was added either 2 hours before (−2 hr) or 2 hours after (+2 hr). Results are presented in FIGS. 18*a*-19*b*.

Experimental Overview:

Calu-3 cells were seeded at a density of $5\times10^5$ cells/well in 24-well plates. Five dilutions of Equivir and vehicle treatment (DMSO) were added to a subset of wells. Two hours after treatment (−2 hours), SARS-CoV-2 was added at MOI of 0.05. After one hour, cells were washed with PBS, and Equivir was added mentioned concentrations to the subset of wells that had previously been treated with Equivir. To rest of the wells Equivir was added 1 hour after wash (+2 hr) at indicated concentrations. Equivir was maintained in the medium throughout the infection. Each concentration was tested in triplicate wells. At 48 hours and 72 hours post-infection, 100 μl of supernatant was removed and viral titer in the media was quantified by measuring TCID50 assay (protocol is below).

Concentrations of Equivir Tested:

Equivir (μg/ml): 200, 150, 100, 50 and 25.

Summary of Results:

Effectiveness of Equivir against SARS-CoV-2 was tested by treating Calu-3 cells with various concentrations of Equivir added at 2 hours before or 2 hours after infection with a MOI of 0.05. Equivir was toxic at concentrations above 100 μg/ml and not toxic at lower concentrations.

Equivir was effective in inhibiting viral replication at non-toxic concentrations of 50 μg/ml when treated 2 hours before infection. Approximately 2 log fold reduction at 48- and 72-hours post-infection was statistically significant (One-way ANOVA). Approximately 3- to 4-fold reduction in viral titers observed at 25 μg/ml (48- and 72-hours PI).

There was no statistically significant reduction in viral replication in cells treated with Equivir 2 hours post-infection.

Limitations of the Study:

Effectiveness of the compound was tested on Calu-3 cells.

A MOI of 0.05 was tested. Therefore, effectiveness of the compounds against higher concentrations is not known.

Inhibition of viral replication by 25 μg/ml of Equivir when added 2 hours before infection needs to be repeated as subsequent confirmation by qRT-PCR does not show a similar reduction in viral titers (STUDY #8 below).

Study #8

Objective:

To determine the effect of Equivir supplied by GRDG against SARS-CoV-2 in Calu-3 cells by qRT-PCR.

Experimental Overview:

Calu-3 cells were seeded at a density of $5 \times 10^5$ cells/well in 24-well plates. Five dilutions of Equivir and vehicle treatment (DMSO) were added to a subset of wells. 2 hours after treatment (−2 hours), SARS-CoV-2 was added at MOI of 0.05. Equivir was added to another subset of wells at the time of infection (0 hr). After one hour, cells were washed with PBS, and Equivir was added at mentioned concentrations to the subset of wells that had previously been treated with Equivir. To rest of the wells Equivir was added 1 hour after wash (+2 hr) at indicated concentrations. Equivir was maintained in the medium throughout the infection. Each concentration was tested in triplicate wells. At 72 hours post-infection, 800 μl of supernatant was removed, RNA isolated, and viral titer in the media was quantified by qRT-PCR (protocol attached as Appendix).

Concentrations Equivir Tested:

Equivir (μg/ml): 200, 150, 100, 50, and 25.

Summary of Results:

Effectiveness of Equivir against SARS-CoV-2 was tested by treating Calu-3 cells with various concentrations of Equivir added at th4 time of infection, 2 hours before or 2 hours after infection with a MOI of 0.05. Equivir was toxic at concentrations above 100 μg/ml and not toxic at lower concentrations.

Equivir was effective in inhibiting viral replication at non-toxic concentrations of 50 μg/ml when treated 2 hours before infection or at the time of infection. Approximately 2 log fold reduction at 72-hours post-infection was statistically significant (One-way ANOVA). No significant reduction in viral copies was noted at 25 μg/ml concentration.

There was no statistically significant reduction in viral replication in cells treated with Equivir 2 hours post-infection at 50 and 25 μg/ml concentrations.

Study #9

Objective:

To determine the effect of Equivir against SARS-CoV-2 in Calu-3 cells by Immunofluorescence.

Experimental Overview:

Calu-3 cells were seeded at a density of $5 \times 10^5$ cells/well in 24-well plates upon a glass coverslip. Three dilutions of Equivir and vehicle treatment (DMSO) were added to a subset of wells. Immediately after adding the compound, SARS-CoV-2 was added at MOI of 0.05. After one hour, cells were washed with PBS, and Equivir was added at mentioned concentrations to the subset of wells that had previously been treated with Equivir. Equivir was maintained in the medium throughout the infection. At 48 hours post-infection, all supernatant was removed, cells fixed, and tested for (presence of viral antigens (NP protein) by Immunofluorescence. (protocol attached as Appendix).

Concentrations Equivir Tested:

Equivir (μg/ml): 75, 50, and 25.

Summary of Results:

Effectiveness of Equivir against SARS-CoV-2 at sub-toxic level was tested by treating Calu-3 cells with various concentrations of Equivir added at the time of infection.

A significantly lower antigen level was detected in cells treated with 50 μg/ml Equivir suggesting significantly reduced viral replication when compared to controls cells infected with SARS-CoV-2.

Limitations of the Study:

Effectiveness of the compound was tested on Calu-3 cells.

A MOI of 0.05 was tested. Therefore, effectiveness of the compounds against higher concentrations is not known.

Immunofluorescence imaging for cells treated with Equivir concentrations at 75 μg/ml and 25 μg/ml is pending (will image if required).

Overall Summary of the Studies:

Equivir is not toxic to Calu-3 cells at concentrations below 100 μg/ml.

Equivir is effective in inhibiting SARS-CoV-2 at a MOI of 0.05 in Calu-3 cells at a dose of 50 μg/ml when the virus and the drug is added at the same time as measured by TCID50 at 48- and 72-hours infection.

Equivir is effective in inhibiting SARS-CoV-2 at a MOI of 0.05 in Calu-3 cells at a dose of 50 μg/ml when the drug is added 2 hours before the virus as measured by TCID50 at 48- and 72-hours infection.

Equivir is effective in inhibiting SARS-CoV-2 at a MOI of 0.05 in Calu-3 cells at a dose of 50 μg/ml when the virus and the drug is added at the same time as measured by qRT-PCR at 72-hours infection.

Equivir is effective in inhibiting SARS-CoV-2 at a MOI of 0.05 in Calu-3 cells at a dose of 50 μg/ml when the drug is added 2 hours before virus as measured by qRT-PCR at 72-hours infection.

Less viral antigens were observed in Calu-3 cells that was treated with Equivir at 50 μg/ml when the virus and the drug is added at the same time as measured by Immunofluorescence.

Study #10

Experimental Overview:

Calu-3 cells were seeded at a density of $1.5 \times 10^5$ cells/well in 24-well plates. Specified wells were given pre-designated treatments of Equivir/Equivir+Gallic Acid either 2 hours prior to or following infection with SARS-CoV-2. Cells were washed and fresh media with treatment was added following infection. Supernatant was harvested and wells were imaged at 48 and 72 hr PI. TCID50 analyses were performed for each treatment condition to determine recoverable concentration of infectious virus following treatment, and LDH analysis was conducted for uninfected, treated wells to determine cytotoxicity of the treatment to Calu-3 cells. Results are shown in FIGS. 24-47.

Study #11

Assessment of the Effect of Three Compounds on the Helicase Activity

Summary

The objective of Study #11 is to assess the effect of the three compounds on helicase activity. This will be achieved using a cell-free, fluorescence-based molecular beacon assay. Briefly, paired DNA oligonucleotides—one tagged with a 5' fluorescent molecule and 3' quencher, one not— were hybridized and then incubated with NS3 or RecQ helicase and test articles. As the helicases unwind these oligos, the labeled strand will anneal with itself to form a hairpin structure that brings the fluorophore into the proximity of the quencher, which reduces fluorescence. The greater the fluorescence, the greater the inhibition of helicase activity.

Introduction

Helicases are enzymes that use nucleotide hydrolysis to catalyze RNA/DNA unwinding, with the purpose of preparing nucleic acids for replication, repair or other processes. For double-stranded DNA or RNA viruses, helicases are critical to facilitate viral replication, making them intriguing targets for antiviral therapies.

Background of the Test System

The test system for this study consists of a cell-free, fluorescence-based in vitro helicase assay. Recombinant NS3, a multifunction Hepatitis C Virus protein that acts as a helicase for both RNA and DNA, and RecQ, an *E. coli* helicase, were both tested for this study. The NS3 helicase is present in several virulent pathogens, including Hepatitis C, West Nile virus and yellow fever virus, and has been used successfully in several studies demonstrating test article interference with helicase activity, making it a useful target. While RecQ participates in processes—such as DNA repair and plasmid recombination—that are not found in viruses, the two helicases are members of the same helicase superfamily, superfamily-2, and there are some conserved sequences in the two helicase's C-terminal regions, suggesting that test articles that inhibit one enzyme may inhibit the other.

Molecular beacons are oligonucleotides labeled with fluorescent tags and quenchers. These beacons are annealed to complimentary strands of DNA, which separates the fluorophore from the quencher in the beacon, allowing fluorescence to be detected. As active helicase unwinds this double-stranded DNA, the beacon separates from the complimentary strand and returns to secondary structure, which quenches and fluorescence. Monitoring the rate of this fluorescence loss allows for a measurement of helicase activity and permits the testing of compounds that may inhibit helicase activity.

Materials and Methods

Test Materials

Test Article

1: Gallic acid

2: Hesperidin

3: Myricetin

Control Items

Negative Control

The negative control was wells treated only with 4% DMSO in helicase assay solution and 0.5 mM ATP. Previous studies have found that the final DMSO concentration can go up to 5% without disrupting the assay.

Positive Control

For a positive control, wells with no ATP (and thus no helicase activity) were included.

Test Article Inventory and Disposition

Records of the receipt, distribution, storage, and disposition of test articles were maintained.

Dose Formulation

Eight concentrations of each test article with be tested in each experiment. Final concentrations for each test article were set at 200, 60, 20, 6, 2, 0.6, 0.2, 0.06 µg/mL (~1 µM to ~10 mM). Each test article was originally dissolved at a concentration of 5 mg/mL in DMSO. From that stock, the other seven working stocks were made by serial half-log dilution in DMSO. These 25× concentrations which will then be distributed into the appropriate helicase assay solution.

Experimental Design

Test System

The test works by incubating helicase with a target oligonucleotide annealed with a complimentary molecular beacon that fluoresces while bound. Upon release from the template strand, the molecular beacon forms a secondary structure that quenches fluorescence. A decrease of fluorescence thus acts as a proxy for helicase activity. The annealed probe of a target strand 5'-GGAGCTGGTGGCGTAGG(T)20-3' (SEQ ID NO.: 1) and a beacon strand 5'-/6-FAM/CCTACGCCACCAGCTCCGTAGG/BHQ/-3' (SEQ ID NO.: 2).

As outlined below the recombinant NS3 acquired by CR-CLE contained only the helicase fragment of the NS3 protein. The tests indicate that the NS3 helicase fragment has little to no activity. As helicases have conserved function and sequences among different species, a full-length *E. coli* helicase, RecQ, was used.

Assay Development

Figure 48:
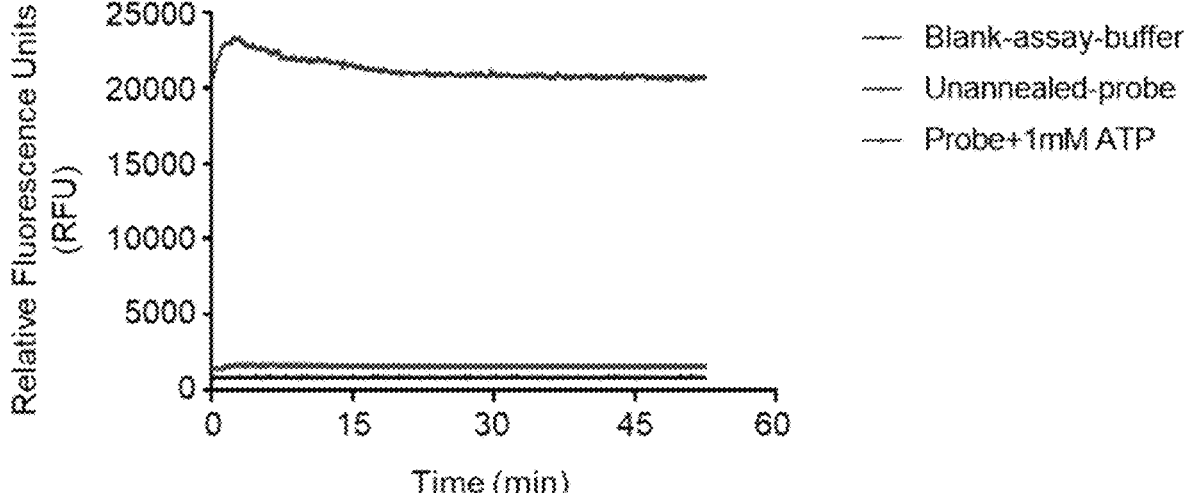
FIG. 48 is a chart comparing relative fluorescent units to time.

Initial experiments were conducted to determine an appropriate annealing protocol. It was established that a 20-minute incubation of a 1:1 molar ratio of probe and target at 95° C., followed by cooling to room temperature and 30 minutes in a 4° C. refrigerator resulted in sufficient annealing as determined by fluorescence (FIG. 48).

Figure 49:
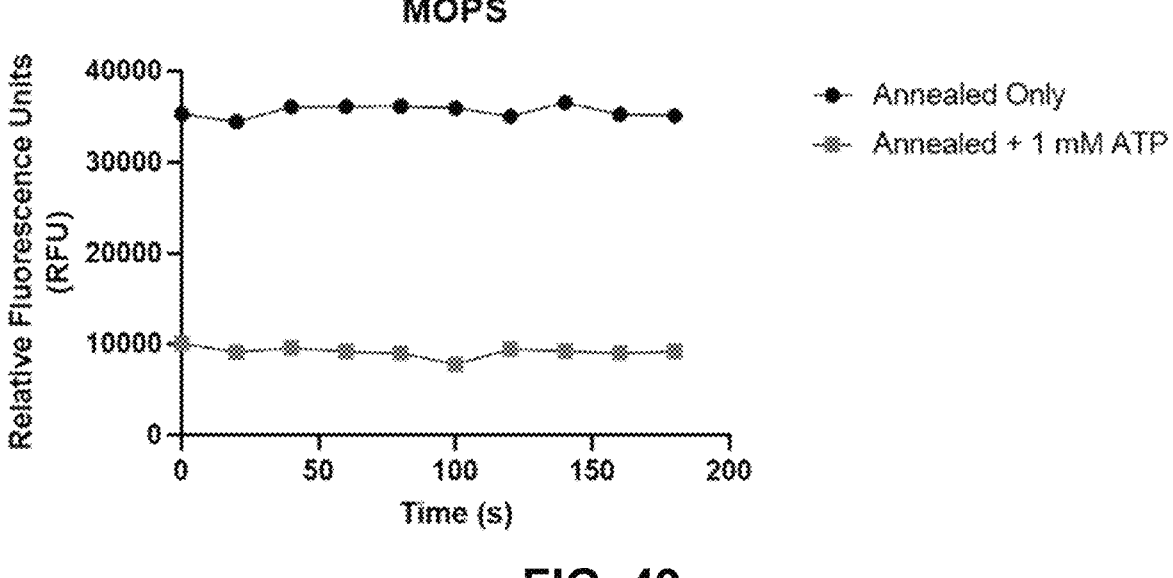
FIG. 49 is a graph comparing relative fluorescent units with time.
Figure 50:
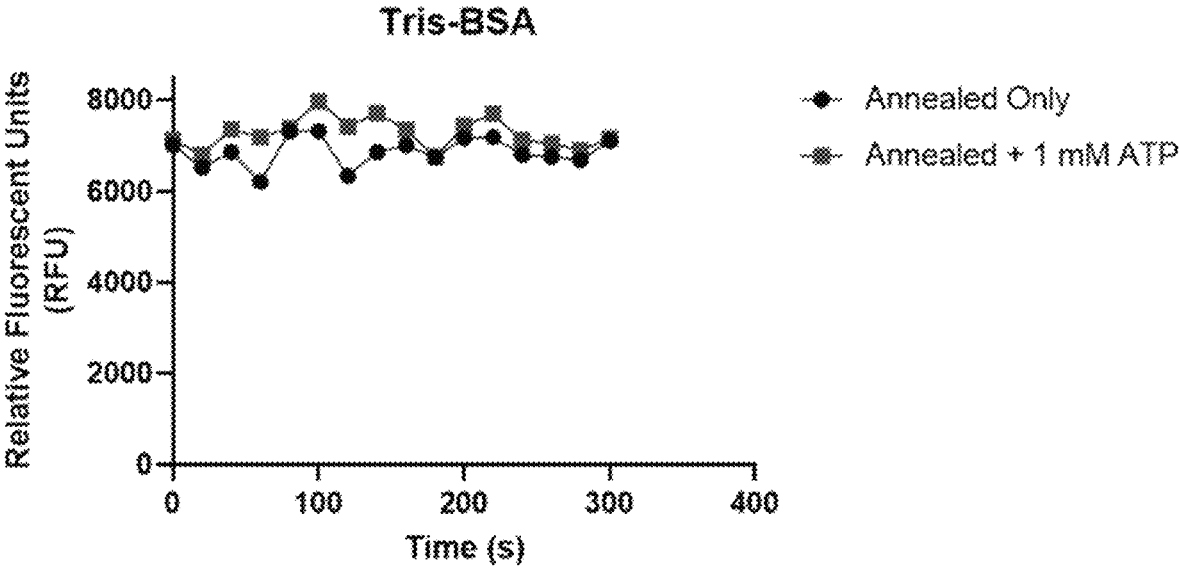
FIG. 50 is a graph comparing relative fluorescent units with time.

It was determined that while using MOPS buffer recommended by the literature, ATP appeared to quench some fluorescent signal without the need for helicase enzyme. Thus, different buffer formulations were tested. A 20 mM Tris-HCl pH 7.5, 10 mM $MgCl_2$, 0.1 mg/mL BSA buffer resulted in limited quenching by ATP (FIG. 49 and FIG. 50). Thus, Tris-BSA was used for all future experiments.

Figure 51:
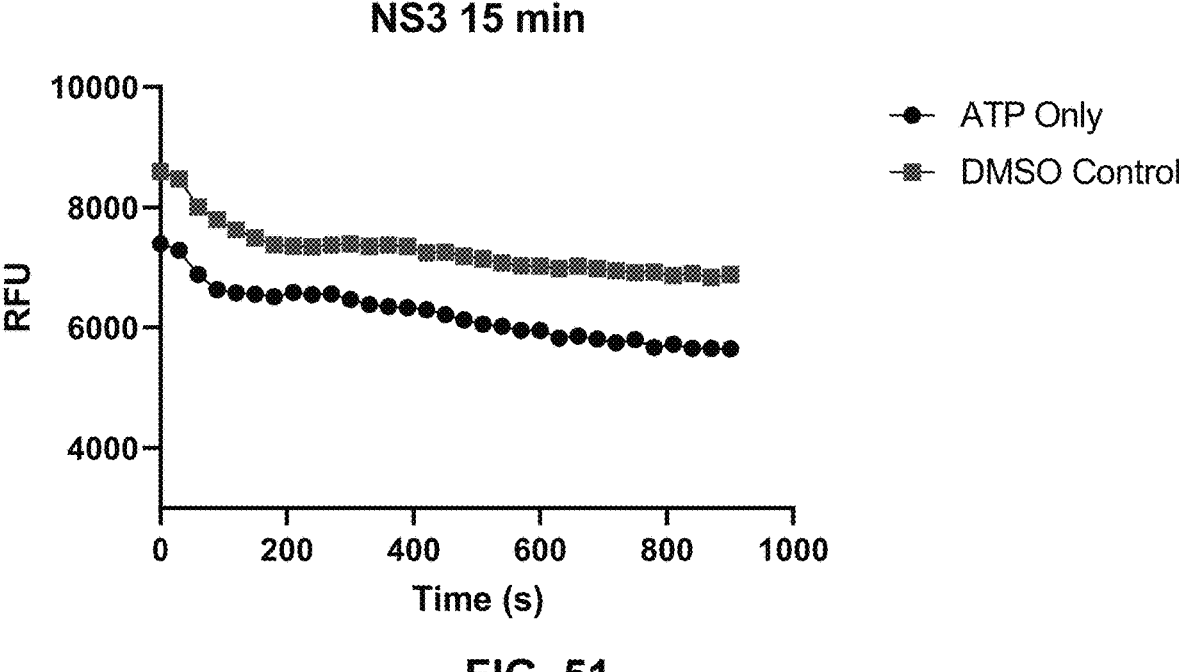
FIG. 51 is a graph comparing RFU with time.
Figure 52:
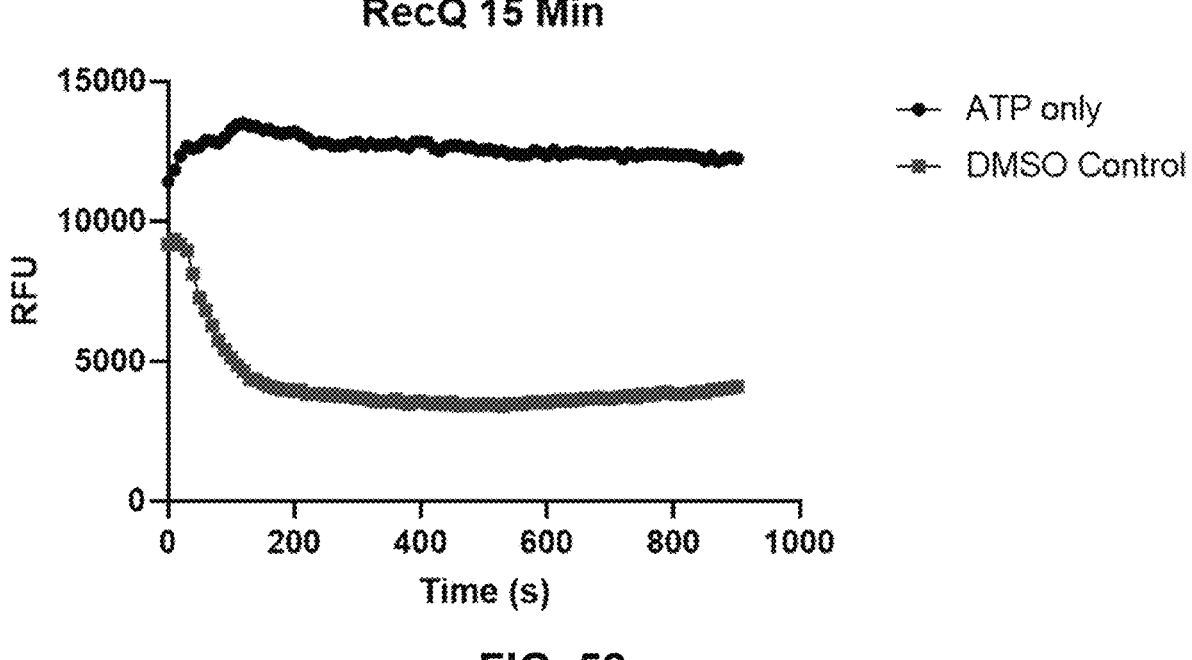
FIG. 52 is a chart comparing RFU with time.

Once an appropriate buffer was chosen, initial tests were performed on the functionality of the NS3 enzyme. Based on the results shown in FIG. 51 and FIG. 52, the NS3 helicase in non-functional, as the addition of ATP does not decrease fluorescence. This may be because the only NS3 enzyme CRL-CLE could source is a 23 kD fragment of the full 70 kD protein. This fragment contains the helicase portion of the protein, but not the N-terminal protease domain. These omissions could affect the stability and function of the helicase.

A full-length bacterial helicase was used in the same superfamily of helicases, RecQ, and found that the addition of this enzyme and ATP to annealed probe strongly decreased fluorescence, indicating active helicase. Therefore, test article experiments with RecQ were performed.

For the final reaction mixture setup, 2 µl of 5 µM enzyme and 2 µl of test article or DMSO was incubated in 43.5 µl of assay buffer for 20 minutes on ice. Prior to the plate read, 2.5 µl of 10 mM ATP was added to the reaction mix, followed by 2 µl of annealed probe. The plate was read immediately following addition of probe.

Data Analysis

Fluorescence readings were transferred to Microsoft Excel to allow further calculations to be performed. Fluorescence measurements are provided by the plate reader in relative fluorescence units (RFU). The % activity (see formula below) for each sample was originally proposed as a readout for helicase inhibition, but raw fluorescence values between wells and conditions varied too widely to make this measurement meaningful.

$$\% \text{ activity} = (RFU_{sample}/\text{mean } RFU_{neg\ control}) * 100.$$

Consequently, results were analysed by calculating the rate of reaction for each condition at 35 minutes, when most reactions had plateaued.

Rate of reaction=$(F_0-F_{35})/35$; where $F_0$ is the RFU value at time 0 and $F_{35}$ is the RFU value 35 minutes into the reaction.

It is possible that the test articles could affect fluorescence independent of helicase activity. Therefore, we performed a run where only annealed probe and test article were mixed in reaction buffer and measured the effect on fluorescence at every concentration (Table 5 below). The ratio of TA fluorescence to buffer only fluorescence and normalized the reaction rates to this ratio.

TABLE 5

|   | 1 | 2 | 3 | 4 | 5 | 6 | 7 | 8 | 9 | 10 | 11 | 12 |
|---|---|---|---|---|---|---|---|---|---|----|----|----|
| A | Blank | Solution + DMSO | No ATP | TA.0.06 | TA 0.2 | TA 0.6 | TA 2 | TA 6 | TA 20 | TA 60 | TA 200 | TA 200 + Buffer |
| B | Blank | Solution + DMSO | No ATP | TA.0.06 | TA 0.2 | TA 0.6 | TA 2 | TA 6 | TA 20 | TA 60 | TA 200 | TA 200 + Buffer |
| C | Blank | Solution + DMSO | No ATP | TA.0.06 | TA 0.2 | TA 0.6 | TA 2 | TA 6 | TA 20 | TA 60 | TA 200 | TA 200 + Buffer |

The mean, standard deviation, standard error of the mean and % coefficient of variation for the normalized rates of reaction were calculated and are presented in Table 5 (above).

Results

Gallic Acid

Figure 53:
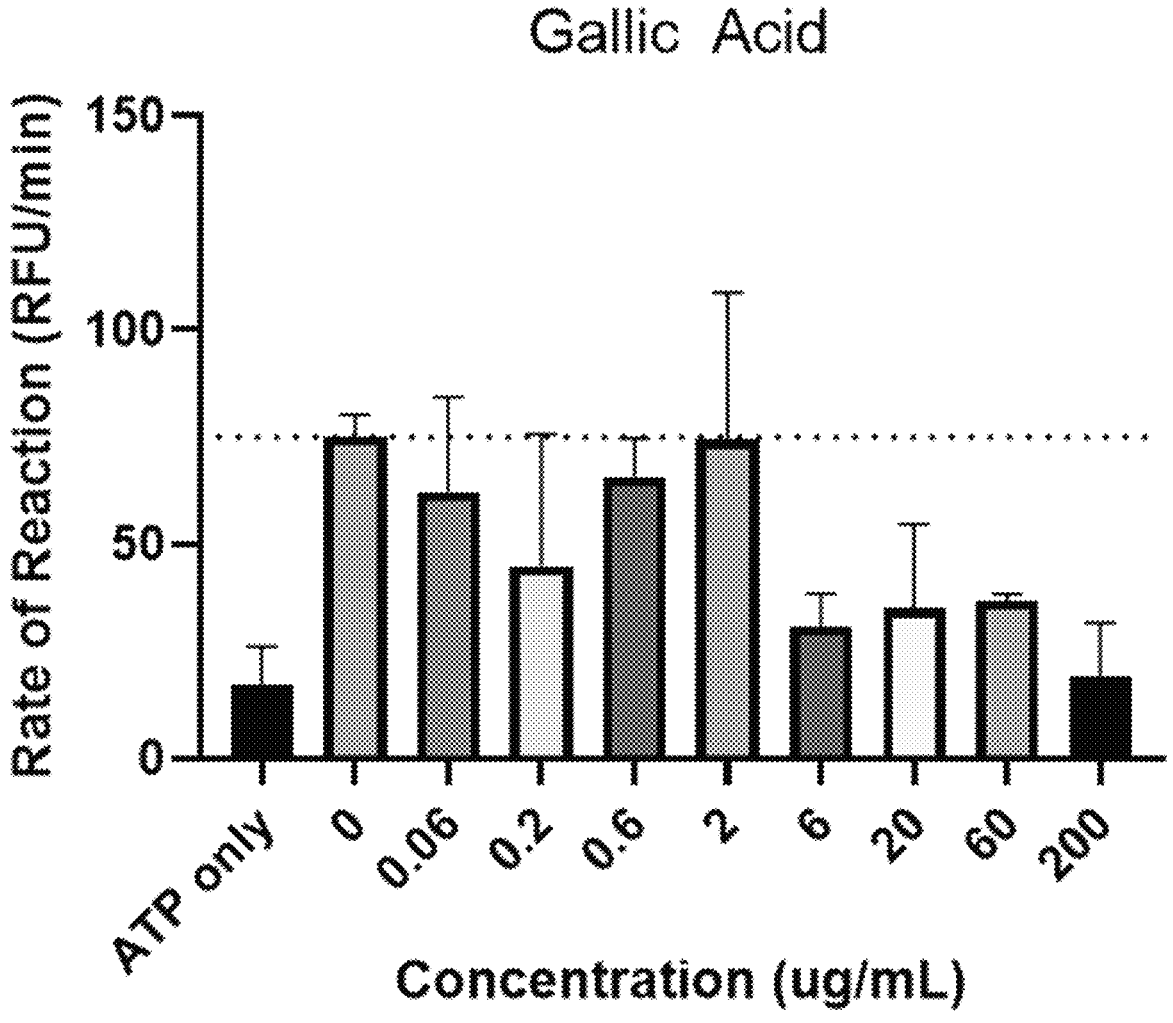
FIG. 53 is a chart comparing rate of reaction with gallic acid concentration.
Figure 54:
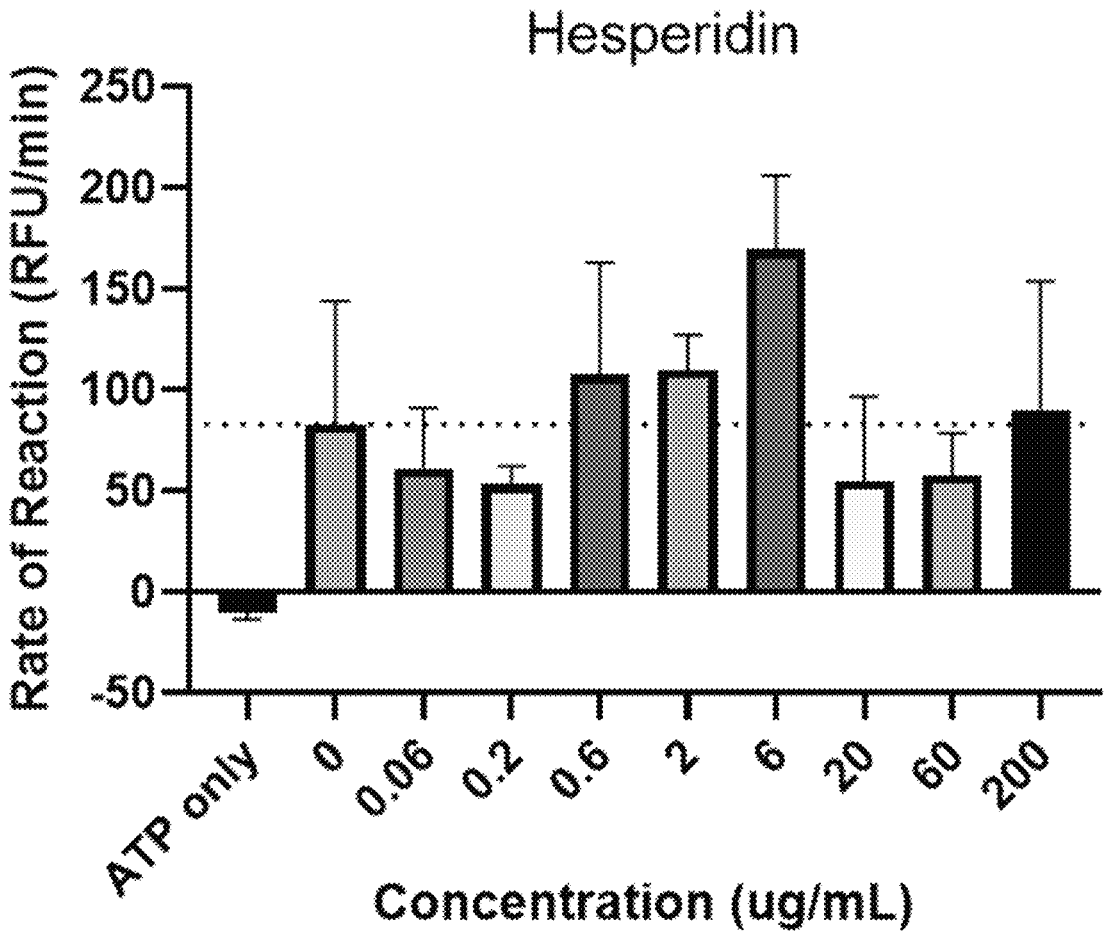
FIG. 54 is a graph comparing rate of reaction with concentration of hesperitin.
Figure 55:
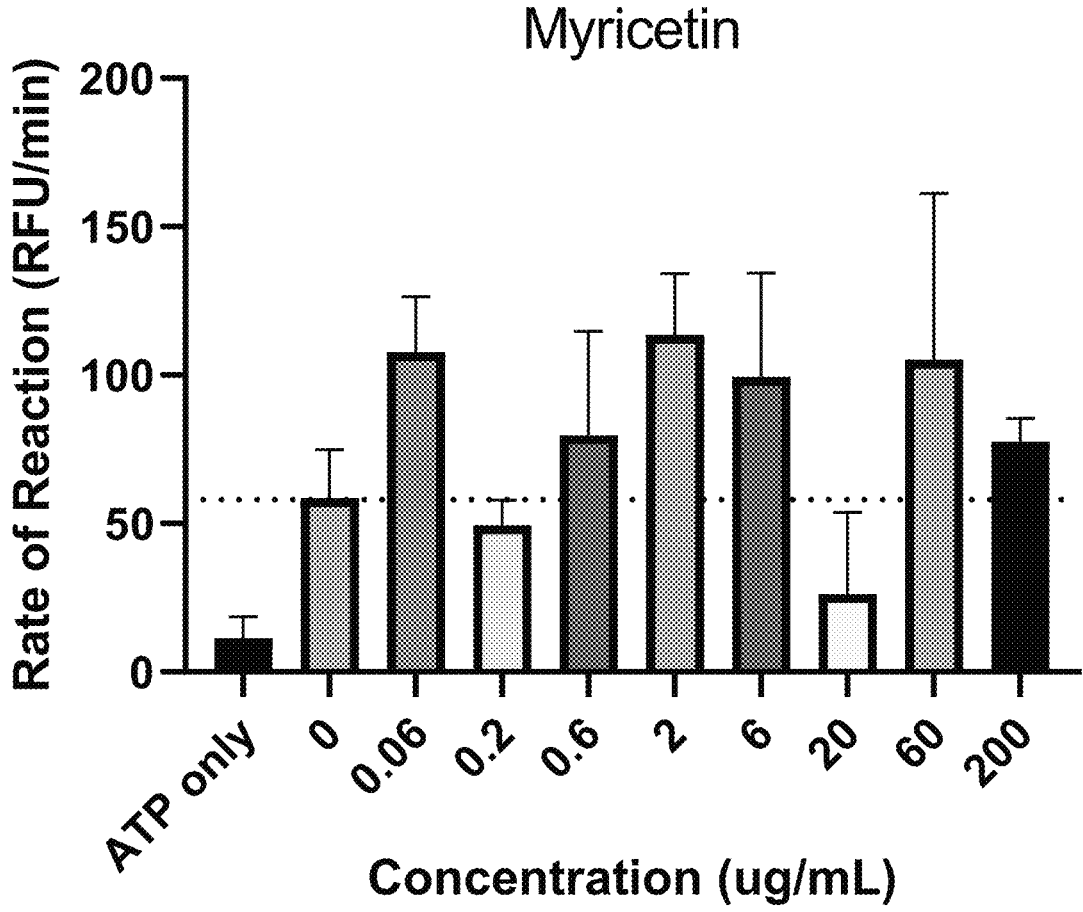
FIG. 55 is a graph comparing rate of reaction with concentration of myricetin.

From 0.06 to 2.0 µg/mL, there appeared to be no clear effect on helicase activity (FIGS. 53-55). However, starting at 6 µg/mL a decrease in helicase activity was observed as measured by the rate of reaction compared to the DMSO control. This decrease was maintained up to and including 200 µg/mL.

Hesperidin

There were no observed clear change in helicase activity at any of the tested concentrations compared to the DMSO control.

Myricetin

There were no observed consistent change in helicase activity at any of the tested concentrations compared to the DMSO control.

TABLE 7

| Run 1 | | | | | | | | | | |
|---|---|---|---|---|---|---|---|---|---|---|
| Gallic Acid | | | | | | | | | | |
| Time | T ° 484.530 | A1 | A2 | A3 | A4 | A5 | A6 | A7 | A8 | A9 |
| 0:00:00 | 22.5 | 770 | 7611 | 7639 | 8891 | 6287 | 7312 | 6525 | 5194 | 5878 |
| 0:35:00 | 22.9 | 724 | 5325 | 6611 | 5772 | 4257 | 5581 | 5425 | 4392 | 5483 |

| Run 1 | | | | | | | | | | |
|---|---|---|---|---|---|---|---|---|---|---|
| Gallic Acid | | | | | | | | | | |
| Time | T ° 484.530 | A10 | A11 | A12 | B1 | B2 | B3 | B4 | B5 | B6 |
| 0:00:00 | 22.5 | 7320 | 5417 | 5227 | 762 | 8224 | 8026 | 5074 | 5266 | 9034 |
| 0:35:00 | 22.9 | 5922 | 5138 | 5425 | 758 | 5441 | 7233 | 4417 | 5773 | 6664 |

| Time | T ° 484.530 | B7 | B8 | B9 | B10 | B11 | B12 | C1 | C2 | C3 |
|---|---|---|---|---|---|---|---|---|---|---|
| 0:00:00 | 22.5 | 7578 | 6945 | 7140 | 8172 | 4722 | 7023 | 766 | 8666 | 6931 |
| 0:35:00 | 22.9 | 5810 | 6148 | 6471 | 6930 | 4496 | 6404 | 759 | 5831 | 6915 |

| Time | T ° 484.530 | C4 | C5 | C6 | C7 | C8 | C9 | C10 | C11 | C12 |
|---|---|---|---|---|---|---|---|---|---|---|
| 0:00:00 | 22.5 | 9132 | 9281 | 8013 | 11476 | 7481 | 8335 | 7531 | 7026 | 6795 |
| 0:35:00 | 22.9 | 6362 | 6105 | 5204 | 6512 | 5863 | 5730 | 6319 | 5495 | 6200 |

TABLE 7-continued

Hesperidin

| Time | T °<br>484.530 | A1 | C1 | B1 | A2 | B2 | C2 | A3 | B3 | C3 |
|---|---|---|---|---|---|---|---|---|---|---|
| 0:00:00 | 20.2 | 873 | 854 | 849 | 7039 | 7767 | 13639 | 8010 | 8699 | 8282 |
| 0:35:00 | 20.7 | 889 | 872 | 867 | 6470 | 6775 | 6455 | 8434 | 9187 | 8411 |

Hesperidin

| Time | T °<br>484.530 | A4 | B4 | C4 | A5 | C5 | B5 | A6 | B6 | C6 |
|---|---|---|---|---|---|---|---|---|---|---|
| 0:00:00 | 20.2 | 5759 | 9125 | 10456 | 7735 | 8642 | 7853 | 14137 | 7347 | 7559 |
| 0:35:00 | 20.7 | 5467 | 6877 | 6542 | 6072 | 6143 | 6397 | 6502 | 5900 | 5304 |

| Time | T °<br>484.530 | A7 | B7 | C7 | A8 | B8 | C8 | A9 | B9 | C9 |
|---|---|---|---|---|---|---|---|---|---|---|
| 0:00:00 | 22.5 | 10359 | 11454 | 8360 | 10222 | 10590 | 17264 | 16242 | 5811 | 8025 |
| 0:35:00 | 22.9 | 6573 | 6526 | 5509 | 6164 | 5213 | 8880 | 11913 | 6518 | 5863 |

| Time | T °<br>484.530 | A10 | B10 | C10 | A11 | B11 | C11 | A12 | B12 | C12 |
|---|---|---|---|---|---|---|---|---|---|---|
| 0:00:00 | 22.5 | 10452 | 7252 | 7210 | 14819 | 7175 | 9180 | 15660 | 9770 | 10477 |
| 0:35:00 | 22.9 | 7008 | 6217 | 5588 | 7231 | 6648 | 7799 | 9497 | 7774 | 9155 |

Myricetin

| Time | T °<br>484.530 | A1 | B1 | C1 | A2 | B2 | C2 | A3 | B3 | C3 | A4 |
|---|---|---|---|---|---|---|---|---|---|---|---|
| 0:00:00 | 20 | 839 | 809 | 821 | 10518 | 4959 | 9908 | 8063 | 7591 | 8190 | 14946 |
| 0:35:00 | 20.6 | 810 | 820 | 790 | 7646 | 4065 | 6093 | 8228 | 7629 | 7884 | 9483 |

Myricetin

| Time | T °<br>484.530 | B4 | C4 | A5 | B5 | C5 | A6 | B6 | C6 |
|---|---|---|---|---|---|---|---|---|---|
| 0:00:00 | 20 | 8957 | 8828 | 10047 | 9670 | 6773 | 11528 | 6477 | 3594 |
| 0:35:00 | 20.6 | 4725 | 5988 | 7144 | 8199 | 5403 | 7961 | 4234 | 5238 |

| Time | T °<br>484.530 | A7 | B7 | C7 | A8 | B8 | C8 | A9 | B9 | C9 |
|---|---|---|---|---|---|---|---|---|---|---|
| 0:00:00 | 22.5 | 12406 | 10235 | 7932 | 13174 | 13286 | 6908 | 12467 | 10604 | 5844 |
| 0:35:00 | 22.9 | 8386 | 5162 | 6669 | 9109 | 7022 | 6649 | 10338 | 6947 | 7412 |

| Time | T °<br>484.530 | A10 | B10 | C10 | A11 | B11 | C11 | A12 | B12 | C12 |
|---|---|---|---|---|---|---|---|---|---|---|
| 0:00:00 | 22.5 | 10868 | 13010 | 5890 | 6608 | 4850 | 6196 | 8965 | 8207 | 5165 |
| 0:35:00 | 22.9 | 8883 | 7317 | 6795 | 5004 | 3826 | 4747 | 4495 | 5122 | 3022 |

Run 2

| Time | DMSO +<br>Enzyme | DMSO +<br>Enzyme | No<br>ATP | No<br>ATP | H<br>0.06 | H<br>0.06 | M 0.06 | M 0.06 | H 0.2 | H 0.2 |
|---|---|---|---|---|---|---|---|---|---|---|
| 0 | 3448 | 3345 | 6515 | 6426 | 5870 | 7788 | 8083 | 5195 | 15786 | 14387 |
| 35:00:00 | 2019 | 2182 | 5834 | 5208 | 2987 | 3023 | 3385 | 3391 | 2237 | 2984 |

Run 2

| Time | DMSO +<br>Enzyme | M 0.2 | M 0.2 | H 0.6 | H 0.6 | M 0.6 | M 0.6 | H 2 | H 2 |
|---|---|---|---|---|---|---|---|---|---|
| 0 | 3448 | 5788 | 4210 | 9523 | 7721 | 9244 | 9661 | 4834 | 11846 |
| 35:00:00 | 2019 | 3820 | 2972 | 2677 | 2621 | 4426 | 3662 | 2624 | 2801 |

TABLE 7-continued

| Time | M 2 | M 2 | H 6 | H 6 | M 6 | M 6 | H 20 | H 20 | M 20 | M 20 |
|---|---|---|---|---|---|---|---|---|---|---|
| 0 | 8530 | 9826 | 8127 | 9570 | 4555 | 9305 | 4464 | 8870 | 5466 | 5022 |
| 35:00:00 | 4289 | 4448 | 2526 | 2818 | 3604 | 4445 | 3653 | 3927 | 5336 | 5025 |

| | Time | H 60 | H 60 | M 60 | M 60 | H 200 | H 200 | M 200 | M 200 |
|---|---|---|---|---|---|---|---|---|---|
| | 0 | 4134 | 3133 | 10879 | 4255 | 3505 | 7126 | 4555 | 3893 |
| | 35:00:00 | 4250 | 4180 | 4100 | 3834 | 3913 | 4063 | 2562 | 2378 |

TABLE 8

|  | Statistics Gallic Acid | | | | |
|---|---|---|---|---|---|
|  | Rate (Triplicate) | Average | S.D. | S.E. | % CV |
| ATP Only | 29.37143 22.65714 0.457143 | 17.49524 | 15.13251 | 8.73676 | 86.49503 |
| DMSO Control | 65.31429 79.51429 81 | 75.27619 | 8.659186 | 4.999383 | 11.50322 |
| 0.06 | 89.11429 18.77143 79.14286 | 62.34286 | 38.06192 | 21.97506 | 61.05257 |
| 0.2 | 58 −14.4857 90.74286 | 44.75238 | 53.8506 | 31.09066 | 120.3301 |
| 0.6 | 49.45714 67.71429 80.25714 | 65.80952 | 15.4881 | 8.942056 | 23.53473 |
| 2.0 | 108.1714 140.8 81.45714 | 74.59048 | 59.00667 | 34.06752 | 79.10751 |
| 6.0 | 115.9429 153.6286 239.5429 | 30.6381 | 13.50194 | 7.795347 | 44.06911 |
| 20.0 | 123.6857 −20.2 61.77143 | 34.94286 | 34.41893 | 19.87178 | 98.50062 |
| 60.0 | 98.4 29.57143 46.34286 | 36.68571 | 2.85314 | 1.647261 | 7.777251 |
| 200.0 | 216.8 15.05714 39.45714 | 19.39048 | 21.10337 | 12.18403 | 108.8337 |

TABLE 9

|  | Statistics Hesperidin | | | | |
|---|---|---|---|---|---|
|  | Rate (Triplicate) | Average | S.D. | S.E. | % CV |
| ATP Only | −12.1143 −13.9429 −3.68571 | −9.91429 | 5.471037 | 3.158705 | −55.1834 |
| DMSO Control | 16.25714 28.34286 205.2571 | 83.28571 | 105.8031 | 61.08543 | 127.0363 |
| 0.06 | 8.342857 64.22857 111.8286 | 61.46667 | 51.79811 | 29.90565 | 84.27025 |
| 0.2 | 47.51429 71.4 41.6 | 53.50476 | 15.77734 | 9.10905 | 29.48772 |
| 0.6 | 218.1429 41.34286 64.42857 | 107.9714 | 96.10695 | 55.48737 | 89.01146 |

TABLE 9-continued

|  | Statistics Hesperidin | | | | |
|---|---|---|---|---|---|
|  | Rate (Triplicate) | Average | S.D. | S.E. | % CV |
| 2.0 | 108.1714 140.8 81.45714 | 110.1429 | 29.72051 | 17.15914 | 26.9836 |
| 6.0 | 115.9429 153.6286 239.5429 | 169.7048 | 63.34882 | 36.57446 | 37.32884 |
| 20.0 | 123.6857 −20.2 61.77143 | 55.08571 | 72.17547 | 41.67053 | 131.0239 |
| 60.0 | 98.4 29.57143 46.34286 | 58.10476 | 35.89011 | 20.72116 | 61.76793 |
| 200.0 | 216.8 15.05714 39.45714 | 90.4381 | 110.1106 | 63.57237 | 121.7524 |

TABLE 10

| | | Statistics Myricetin | | | |
|---|---|---|---|---|---|
| | Rate (Triplicate) | Average | S.D. | S.E. | % CV |
| ATP Only | −4.71429 −1.08571 8.742857 | 0.980952 | 6.962543 | 4.019826 | 709.7738 |
| DMSO Control | 82.05714 25.54286 109 | 72.2 | 42.59279 | 24.59096 | 58.99279 |
| 0.06 | 156.0857 120.9143 81.14286 | 119.381 | 37.49495 | 21.64772 | 31.40782 |
| 0.2 | 82.94286 42.02857 39.14286 | 54.70476 | 24.49744 | 14.1436 | 44.78118 |
| 0.6 | 101.9143 64.08571 −46.9714 | 39.67619 | 77.38609 | 44.67888 | 195.0442 |
| 2.0 | 114.8571 144.9429 36.08571 | 98.62857 | 56.21383 | 32.45507 | 56.99548 |
| 6.0 | 123.2906 189.9857 7.855414 | 107.0439 | 92.1457 | 53.20034 | 86.08215 |
| 20.0 | 64.3324 110.5042 −47.3806 | 42.48536 | 81.17803 | 46.86816 | 191.0729 |
| 60.0 | 74.73798 214.3492 −34.0744 | 85.00425 | 124.5296 | 71.89721 | 146.4981 |
| 200.0 | 81.98167 52.33742 74.0595 | 69.45953 | 15.34813 | 8.861248 | 22.09651 |

Conclusion

Gallic acid, at concentrations at or above 6 ug/mL, inhibits RecQ helicase activity, while hesperidin and myricetin have no effect. Whether these results carry over into the viral helicase, NS3, is unknown, and will likely require further testing with a full-length enzyme.

Study #12

Evaluation of In Vitro LPS Induced Cytokine Release Inhibition In Human PBMC

LIST OF ABBREVIATIONS

| Abbreviation | Definition |
|---|---|
| LPS | Lipopolysaccharide |
| Myr | Myricetin |
| HES | Hesperidin |
| GA | Gallic Acid |
| MH | Myricetin + Hesperidin |
| GMH | Gallic Acid + Myricetin + Hesperidin |
| PBMC | Peripheral Blood Mononuclear Cell |
| IL | Interleukin |
| IL-1b | Interleukin 1 beta |
| IL-2 | Interleukin 2 |
| IL-6 | Interleukin 6 |
| IFN-g | Interferon gamma |
| TNF-a | Tumour Necrosis Factor alpha |
| DMSO | Dimethylsulfoxide |
| LLOQ | Lower Limit of Quantitation |

Summary

The objective of this study was to determine the effects of polyphenols myricetin and hesperidin and the phenolic acid gallic acid alone or in combination on LPS stimulated secretion of the cytokines IL-1b, IL-2, IL-6, IFN-g and TNF-α using an in vitro stimulation assay with human PBMCs.

Stimulation with 1 ng/mL LPS resulted in a robust secretion of IL-1b, IL-6 and TNF-α after 8 hours. No secretion of IL-2 or IFN-g was detectable.

Incubation of cells with hesperidin (200 mM) or the combination of myricetin (200 mM) and hesperidin (200 mM) resulted in an increase in LPS stimulated secretion of IL-1b after 8 hours, while incubation with gallic acid (200 mM) or the combination of gallic acid (200 mM) myricetin (200 mM) and hesperidin (200 mM) resulted in a decrease in LPS stimulated secretion of IL-1b and IL-6 after 8 hours.

Introduction

The objective of this study was to determine the immunomodulatory potential of myricetin, hesperidin and gallic acid alone or in combination on proinflammatory cytokine production in human PBMCs following LPS stimulation in an in vitro setting.

This study was conducted in two phases. The first phase was conducted to determine the optimal LPS concentration and stimulation time to observe cytokine release and enable the detection of cytokine release inhibition by various compounds. The second phase was conducted to identify any effect of the test chemicals myricetin, hesperidin and gallic acid alone or in combination on LPS stimulated cytokine secretion.

Materials and Methods

Phase 1: LPS Concentration Optimization and Compound-Alone Controls

Whole blood was collected from 3 human donors and peripheral blood mononuclear cells (PBMC) were isolated using the Ficoll-Paque density gradient method. PBMC were then plated and left untouched for 2 hours to account for a 2 hours pretreatement period (see below for details), and incubated for 8 or 24 hours in a humidified incubator set to maintain 37° C. with 5% $CO_2$, with different concentrations of LPS as per Table 11 in order to determine the optimal stimulation conditions to detect cytokine release. In parallel, the immunomodulatory effects of myricetin, hesperidin and gallic acid on PBMC cytokine production, in the absence of LPS, was assessed in a soluble stimulation format. Cells were treated with the chemicals alone or in combinations (Myr & HES; Myr, HES & GA) for 10 or 26 hours to account for a 2 hour pretreatment with the compounds followed by an 8 or 24 hour stimulation. RPMI medium alone or supplemented with 0.1% DMSO (to mimic treatment conditions) were used as negative controls.

The treatment conditions are presented in Table 11.

TABLE 11

Phase 1 Treatment Conditions

| Treatment | Concentration | DMSO | LPS |
|---|---|---|---|
| RPMI alone | — | — | — |
| DMSO control | — | 0.1% | — |
| LPS | — | 0.1% | 1000 ng/mL |
| | | | 100 ng/mL |
| | | | 50 |
| Myricetin | 100 μm | 0.1% | — |
| Hesperidin | 10 μm | | |
| Gallic Acid | 1 μm | | |
| Myricetin + Hesperidin[a] | | | |
| Gallic Acid + Myricetin + Hesperidin[a] | | | |

[a]Each individual compound added at concentration indicated
— Not applicable

At the end of the incubation period, supernatant samples were recovered and stored at −80° C. until analysis (in duplicate) using a Luminex platform with the Milliplex MAP Human High Sensitivity T Cell Panel Immunology Multiplex Assay (Cat. No. HSTCMAG-28SK) with the following selected cytokines of interest: IL-1, IL-2, IL-6, IFN-g and TNF-α. Each assay was defined by one calibration curve and 2 sets of QCs and the results were expressed as pg/mL.

Phase 2: LPS Stimulation with Myricetin, Hesperidin and Gallic Acid Treatment

Whole blood was collected from 3 human donors and peripheral blood mononuclear cells (PBMC) were isolated using the Ficoll-Paque density gradient method.

The immunomodulatory effects of myricetin, hesperidin and gallic acid on LPS stimulated PBMC cytokine production was assessed in a soluble stimulation format. Cells were pretreated with the chemicals alone or in combinations (Myr & HES; Myr, HES & GA) for 2 hours followed by stimulation with 1 ng/mL of LPS for 8 hours. Treatment was carried out in a humidified incubator set to maintain 37° C. with 5% $CO_2$. RPMI medium alone, RPMI supplemented with 0.2% DMSO (to mimic treatment conditions) or LPS stimulation alone were used as controls.

The treatment conditions are presented in Table 12.

TABLE 12

Phase 2 Treatment Conditions

| Treatment | Concentration | DMSO | LPS |
|---|---|---|---|
| RPMI alone | — | — | — |
| DMSO control | — | 0.2% | — |
| LPS Alone | — | 0.2% | 1 ng/mL |
| Myricetin | 200 μm | 0.2% | 1 ng/mL |

TABLE 12-continued

Phase 2 Treatment Conditions

| Treatment | Concentration | DMSO | LPS |
|---|---|---|---|
| Hesperidin | 100 μm | | |
| Gallic Acid | 10 μm | | |
| Myricetin + Hesperidin[a] | | | |
| Gallic Acid + Myricetin + Hesperidin[a] | | | |

[a]Each individual compound added at concentration indicated
— Not applicable

Results and Discussion

Phase 1

Individual responses for each concentration of LPS are presented in Table 13 (below) for 8 hours and Table 14 (below) for 24 hours.

TABLE 13

Cytokine Levels in Supernatant Following 8-Hour LPS Treatment

| | Mean Concentration (pg/mL) | | | | |
|---|---|---|---|---|---|
| Treatment | TNF-α | IL-1β | IL-6 | IL-2 | IFN-g |
| | Donor 1 | | | | |
| RPMI Alone | 10.66 | <LLOQ | <LLOQ | <LLOQ | <LLOQ |
| DMSO | 9.94 | <LLOQ | 1.13 | <LLOQ | <LLOQ |
| LPS 1000 ng/mL | 498.68 | 441.01 | 166.25 | <LLOQ | <LLOQ |
| LPS 100 ng/mL | 386.41 | 298.82 | 37.62 | <LLOQ | <LLOQ |
| LPS 50 ng/mL | 511.42 | 327.69 | 75.24 | <LLOQ | <LLOQ |
| LPS 10 ng/mL | 912.13 | 404.91 | 192.2 | <LLOQ | <LLOQ |
| LPS 1 ng/mL | 670.9 | 403.43 | 64.83 | <LLOQ | <LLOQ |
| | Donor 2 | | | | |
| RPMI Alone | 7.74 | <LLOQ | 3.76 | <LLOQ | <LLOQ |
| DMSO | 7.95 | <LLOQ | 4.01 | <LLOQ | <LLOQ |
| LPS 1000 ng/mL | 1276.06 | 1008.83 | 895.76 | <LLOQ | <LLOQ |
| LPS 100 ng/mL | 1313.93 | 873.62 | 820.5 | <LLOQ | <LLOQ |
| LPS 50 ng/mL | 1143.84 | 1002.11 | 880.71 | <LLOQ | <LLOQ |
| LPS 10 ng/mL | 955.81 | 879.72 | 830.13 | <LLOQ | <LLOQ |
| LPS 1 ng/mL | 817.83 | 575.75 | 659.3 | <LLOQ | <LLOQ |
| | Donor 3 | | | | |
| RPMI Alone | 2.92 | <LLOQ | 1.39 | <LLOQ | <LLOQ |
| DMSO | 9.75 | 3.10 | 8.71 | <LLOQ | <LLOQ |
| LPS 1000 ng/mL | 1481.27 | 1979.93 | 1251.62 | <LLOQ | <LLOQ |
| LPS 100 ng/mL | 868.83 | 1222.41 | 817.27 | <LLOQ | <LLOQ |
| LPS 50 ng/mL | 1051.41 | 1751.4 | 1096.09 | <LLOQ | <LLOQ |
| LPS 10 ng/mL | 1113.95 | 1768.06 | 1084.03 | <LLOQ | <LLOQ |
| LPS 1 ng/mL | 1149.23 | 1756.56 | 1103.64 | <LLOQ | <LLOQ |
| LPS 1 ng/mL | 1149.23 | 1756.56 | 1103.64 | <LLOQ | <LLOQ |

IL-1b LLOQ = 2.337 pg/mL, IL-6 LLOQ = 0.870 pg/mL, IL-2 LLOQ = 2.387 pg/mL, IFN-g LLOQ = 2.872 pg/mL

TABLE 14

Cytokine levels in supernatant following 24-hour LPS treatment.

| | Mean Concentration (pg/mL) | | | | |
|---|---|---|---|---|---|
| Treatment | TNF-α | IL-1β | IL-6 | IL-2 | IFN-g |
| | Donor 1 | | | | |
| RPMI Alone | 26.31 | 2.40 | 4.37 | <LLOQ | <LLOQ |
| DMSO | 24.63 | <LLOQ | 3.89 | <LLOQ | <LLOQ |
| LPS 1000 ng/mL | 1675.83 | 799.96 | 1363.37 | 349.73 | <LLOQ |
| LPS 100 ng/mL | 1792.89 | 913.95 | 1390.38 | <LLOQ | <LLOQ |
| LPS 50 ng/mL | 1680.24 | 899.92 | 1317.99 | <LLOQ | <LLOQ |
| LPS 10 ng/mL | 2316.87 | 986.68 | 1393.01 | <LLOQ | <LLOQ |
| LPS 1 ng/mL | 1768.29 | 923.42 | 1284.85 | <LLOQ | <LLOQ |

TABLE 14-continued       TABLE 15-continued

Cytokine levels in supernatant following 24-hour LPS treatment.

| Treatment | Mean Concentration (pg/mL) | | | | |
|---|---|---|---|---|---|
| | TNF-α | IL-1β | IL-6 | IL-2 | IFN-g |
| Donor 2 | | | | | |
| RPMI Alone | 35.09 | <LLOQ | 3.31 | <LLOQ | <LLOQ |
| DMSO | 29.50 | <LLOQ | 2.99 | <LLOQ | <LLOQ |
| LPS 1000 ng/mL | 2286.74 | 1145.77 | 1519.68 | <LLOQ | <LLOQ |
| LPS 100 ng/mL | 1332.65 | 1182.07 | 1243.06 | <LLOQ | <LLOQ |
| LPS 50 ng/mL | 1378.24 | 1170.32 | 1333.24 | <LLOQ | <LLOQ |
| LPS 10 ng/mL | 1605.58 | 1038.39 | 1167.49 | <LLOQ | <LLOQ |
| LPS 1 ng/mL | 2299.94 | 1164.43 | 1269.72 | <LLOQ | <LLOQ |
| Donor 3 | | | | | |
| RPMI Alone | 11.45 | <LLOQ | 2.36 | <LLOQ | <LLOQ |
| DMSO | 11.76 | <LLOQ | 2.21 | <LLOQ | <LLOQ |
| LPS 1000 ng/mL | 3069.72 | 2192.5 | 2426.8 | <LLOQ | <LLOQ |
| LPS 100 ng/mL | 2343.08 | 2282.4 | 2083.25 | <LLOQ | <LLOQ |
| LPS 50 ng/mL | 1954.44 | 2216.54 | 1966.58 | <LLOQ | <LLOQ |
| LPS 10 ng/mL | 2139.91 | 2391.98 | 2016.76 | <LLOQ | <LLOQ |
| LPS 1 ng/mL | 2108.58 | 2396.79 | 1897.32 | <LLOQ | <LLOQ |

IL-1β LLOQ = 2.337 pg/mL, IL-6 LLOQ = 0.870 pg/mL, IL-2 LLOQ = 2.387 pg/mL, IFN-g LLOQ = 2.872 pg/mL

Figure 56A:
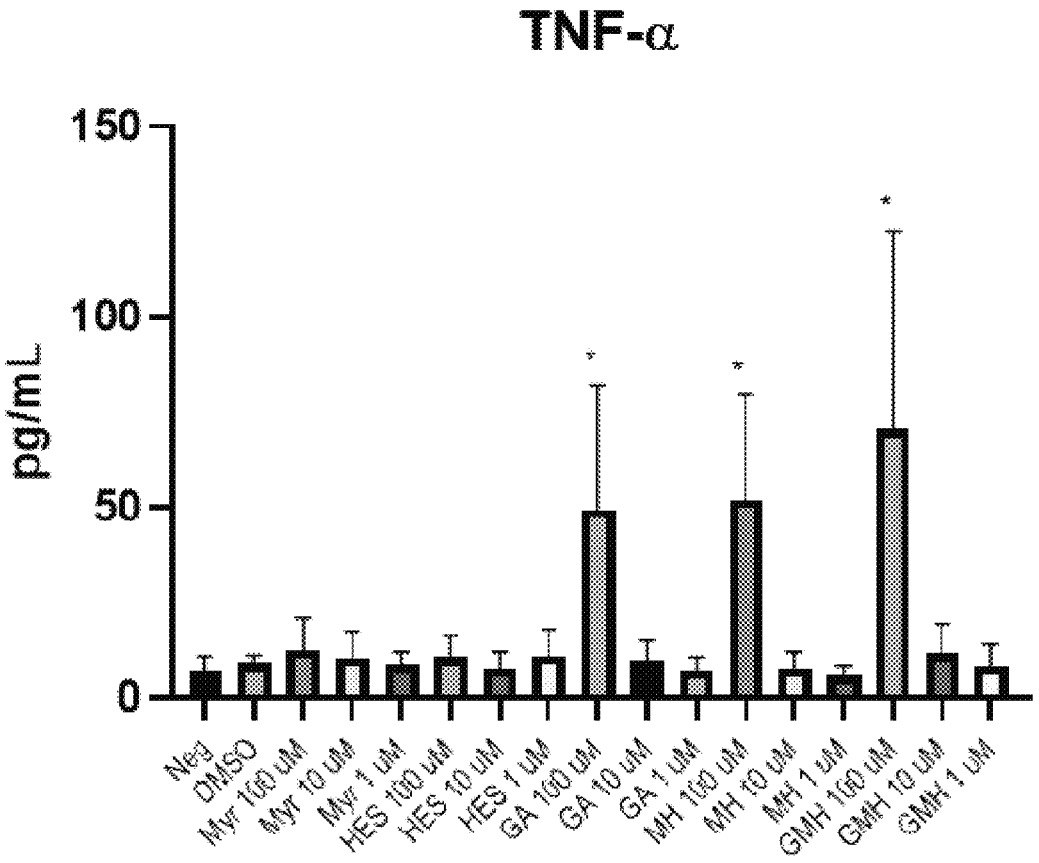
Figure 56B:
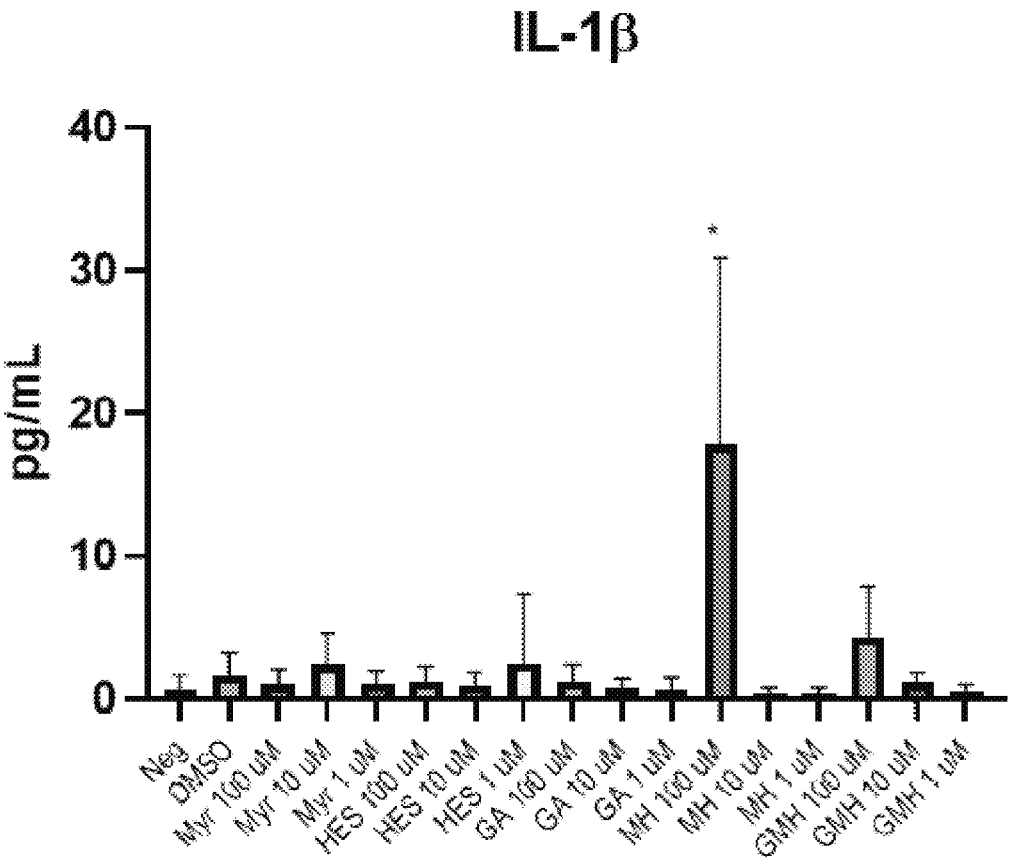
Figure 56C:
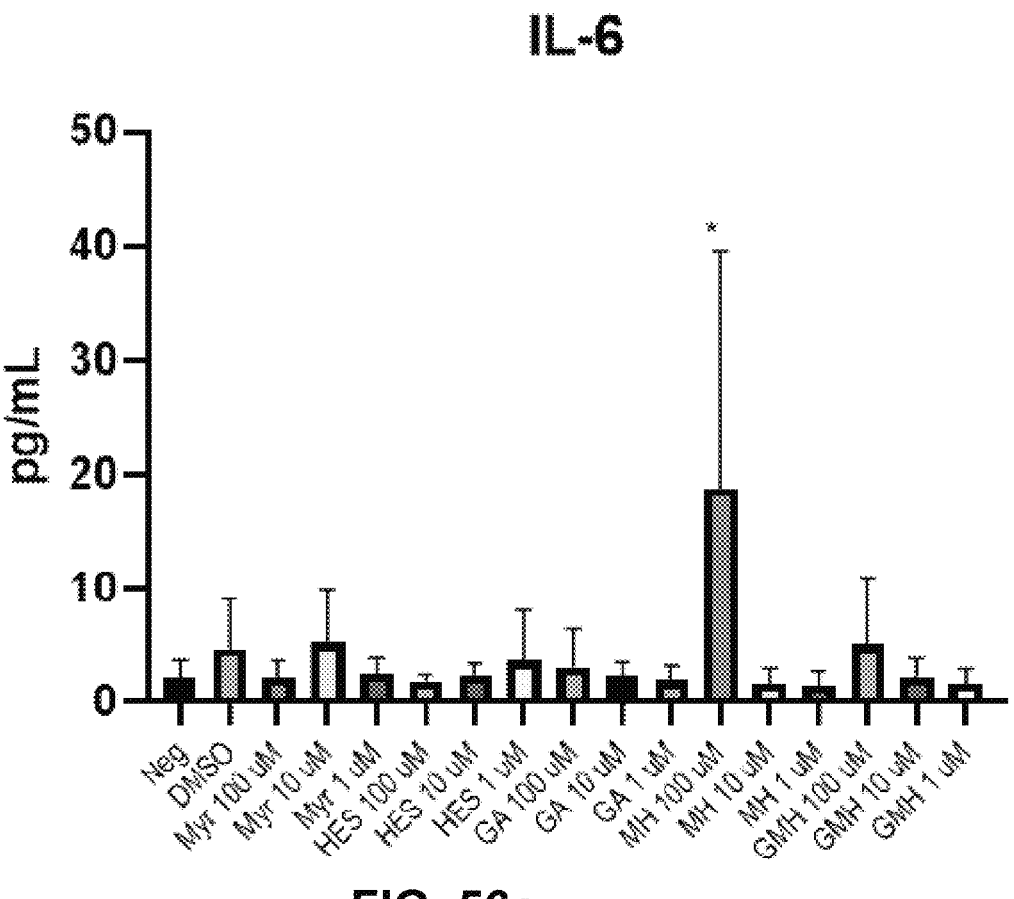

Individual responses for each analyte at 10 hours are presented in Table 11 and mean results are presented in FIG. 62. Individual responses for each analyte at 26 hours are presented in Table 15 (below) and mean results are presented in FIGS. 56a-56c.

TABLE 15

Cytokine Levels in Supernatant Following 10-Hour Treatment

| Treatment | Concentration (pg/mL) | | | | |
|---|---|---|---|---|---|
| | TNF-α | IL-1β | IL-6 | IL-2 | IFN-g |
| Donor 1 | | | | | |
| RPMI Alone | 10.66 | <LLOQ | 0.83 | <LLOQ | <LLOQ |
| DMSO | 9.94 | <LLOQ | 1.13 | <LLOQ | <LLOQ |
| Myr 100 mM | 21.98 | <LLOQ | 1.48 | <LLOQ | <LLOQ |
| Myr 10 mM | 15.35 | 2.98 | 2.84 | <LLOQ | <LLOQ |
| Myr 1 mM | 12.37 | <LLOQ | 1.38 | <LLOQ | <LLOQ |
| HES 100 mM | 14.12 | <LLOQ | 2.13 | <LLOQ | <LLOQ |
| HES 10 mM | 11.72 | <LLOQ | 2.07 | <LLOQ | <LLOQ |
| HES 1 mM | 10.31 | <LLOQ | 1.32 | <LLOQ | <LLOQ |
| GA 100 mM | 46.81 | <LLOQ | <LLOQ | <LLOQ | <LLOQ |
| GA 10 mM | 15.97 | <LLOQ | 1.27 | <LLOQ | <LLOQ |
| GA 1 mM | 10.25 | <LLOQ | <LLOQ | <LLOQ | <LLOQ |
| MH 100 mM | 37.37 | 6.89 | 3.22 | <LLOQ | 3.11 |
| MH 10 mM | 11.48 | <LLOQ | 0.89 | <LLOQ | <LLOQ |
| MH 1 mM | 8.36 | <LLOQ | <LLOQ | <LLOQ | <LLOQ |
| GMH 100 mM | 54.00 | <LLOQ | 1.02 | <LLOQ | <LLOQ |
| GMH 10 mM | 20.60 | <LLOQ | 1.63 | <LLOQ | <LLOQ |
| GMH 1 mM | 14.00 | <LLOQ | 1.07 | <LLOQ | <LLOQ |
| Donor 2 | | | | | |
| RPMI Alone | 7.74 | <LLOQ | 3.76 | <LLOQ | <LLOQ |
| DMSO | 7.95 | <LLOQ | 4.01 | <LLOQ | 2.95 |
| Myr 100 mM | 12.06 | <LLOQ | 3.80 | <LLOQ | <LLOQ |
| Myr 10 mM | 10.78 | 3.14 | 9.50 | <LLOQ | <LLOQ |
| Myr 1 mM | 7.78 | <LLOQ | 2.79 | <LLOQ | <LLOQ |
| HES 100 mM | 14.12 | 4.89 | 2.13 | <LLOQ | <LLOQ |
| HES 10 mM | 8.02 | <LLOQ | 3.08 | <LLOQ | <LLOQ |
| HES 1 mM | 8.33 | <LLOQ | 2.46 | <LLOQ | <LLOQ |
| GA 100 mM | 86.46 | 2.58 | 7.16 | <LLOQ | <LLOQ |
| GA 10 mM | 8.12 | <LLOQ | 2.80 | <LLOQ | <LLOQ |
| GA 1 mM | 7.84 | <LLOQ | 3.05 | <LLOQ | <LLOQ |
| MH 100 mM | 32.00 | 12.31 | 7.62 | <LLOQ | <LLOQ |
| MH 10 mM | 8.66 | <LLOQ | 3.17 | <LLOQ | <LLOQ |
| MH 1 mM | 6.35 | <LLOQ | 2.90 | <LLOQ | <LLOQ |
| GMH 100 mM | 135.11 | 8.91 | 12.52 | <LLOQ | 3.03 |

TABLE 15-continued

Cytokine Levels in Supernatant Following 10-Hour Treatment

| Treatment | Concentration (pg/mL) | | | | |
|---|---|---|---|---|---|
| | TNF-α | IL-1β | IL-6 | IL-2 | IFN-g |
| GMH 10 mM | 10.98 | <LLOQ | 4.02 | <LLOQ | <LLOQ |
| GMH 1 mM | 8.53 | <LLOQ | 3.11 | <LLOQ | <LLOQ |
| Donor 3 | | | | | |
| RPMI Alone | 2.92 | <LLOQ | 1.39 | <LLOQ | <LLOQ |
| DMSO | 9.75 | 3.17 | 8.71 | <LLOQ | <LLOQ |
| Myr 100 mM | 2.94 | <LLOQ | <LLOQ | <LLOQ | <LLOQ |
| Myr 10 mM | 5.17 | <LLOQ | 3.12 | <LLOQ | <LLOQ |
| Myr 1 mM | 5.90 | <LLOQ | 3.06 | <LLOQ | <LLOQ |
| HES 100 mM | 3.49 | <LLOQ | 1.10 | <LLOQ | <LLOQ |
| HES 10 mM | 3.21 | <LLOQ | 1.58 | <LLOQ | <LLOQ |
| HES 1 mM | 13.62 | 6.93 | 6.83 | <LLOQ | <LLOQ |
| GA 100 mM | 14.91 | <LLOQ | 1.55 | <LLOQ | <LLOQ |
| GA 10 mM | 4.62 | <LLOQ | 2.57 | <LLOQ | <LLOQ |
| GA 1 mM | 3.56 | <LLOQ | 1.56 | <LLOQ | <LLOQ |
| MH 100 mM | 86.13 | 34.13 | 45.36 | <LLOQ | <LLOQ |
| MH 10 mM | 2.98 | <LLOQ | <LLOQ | <LLOQ | <LLOQ |
| MH 1 mM | 2.45 | <LLOQ | <LLOQ | <LLOQ | <LLOQ |
| GMH 100 mM | 23.09 | 2.4 | 1.36 | <LLOQ | <LLOQ |
| GMH 10 mM | 3.06 | <LLOQ | <LLOQ | <LLOQ | <LLOQ |
| GMH 1 mM | 2.21 | <LLOQ | <LLOQ | <LLOQ | <LLOQ |

IL-1β LLOQ = 2.317 pg/mL, IL-6 LLOQ = 0.836 pg/mL, IL-2 LLOQ = 2.410 pg/mL, IFN-g LLOQ = 2.791 pg/mL

For all donors, LPS at a concentration ≥1 ng/mL triggered a robust production of TNF-α, IL-1β, and IL-6 at 8 and 24 hours. Measurements of TNF-α, IL-1β, and IL-6 production following LPS stimulation varied between donors, but cytokine production was higher at 24 hours than at 8 hours. No spontaneous cytokine release was induced when samples were incubated with RPMI medium alone or with DMSO (negative controls). No significant production of IFN-g or IL-2 was detected regardless of treatments, timepoints or donors. Based on these results, the lowest concentration of LPS tested (1 ng/mL), with the shortest stimulation time was selected for phase 2 of the study.

Incubation of PBMC with the compounds alone or in combination did not induce cytokine secretion at 1 or 10 μM. However, mild levels of cytokine release was observed at 100 uM. Indeed, treatment with MH, GA and GMH alone at 100 mM resulted in minor increases in TNF-α, IL-1β, and/or IL-6 production at 10 hours. Moreover, at 26 hours, most compounds alone or in combination induced mild levels of TNF-α secretion at 100 μM and in one donor, secretion of IL-1β, and IL-6 was also observed with hesperidin. Based on these results, secretion of cytokines is expected to be minimal following a 10 hour incubation period with the compounds alone. It should be noted that the concentrations of the compounds tested was increased up to 200 μM in the second phase of the study, given that 100 μM might be below the threshold at which the test compounds may have an effect. Given that minimal cytokine induction was measured at the 100 μM concentrations following a 10 hour incubation period, this change was considered acceptable following consultation with the sponsor.

Phase 2

Individual responses for each analyte after 8 hours LPS stimulation are presented in Table 16 (below) and mean results are presented as fold-change relative to LPS treatment alone in Table 17 (below). Graphical representation of pooled results are presented in FIGS. 58a-58c.

TABLE 16

Cytokine Levels in Supernatant Following 26-Hour Treatment

| Treatment | TNF-α | IL-1β | IL-6 | IL-2 | IFN-g |
|---|---|---|---|---|---|
| | | Donor 1 | | | |
| RPMI Alone | 26.32 | 2.61 | 4.4 | <LLOQ | <LLOQ |
| DMSO | 24.63 | <LLOQ | 3.89 | <LLOQ | <LLOQ |
| Myr 100 mM | 51.16 | <LLOQ | 8.6 | <LLOQ | <LLOQ |
| Myr 10 mM | 25.47 | <LLOQ | 4.09 | <LLOQ | <LLOQ |
| Myr 1 mM | 26.5 | <LLOQ | 4.15 | <LLOQ | <LLOQ |
| HES 100 mM | 85.86 | 53.61 | 29.18 | 3.97 | <LLOQ |
| HES 10 mM | 29.56 | <LLOQ | 4.15 | 2.19 | <LLOQ |
| HES 1 mM | 35.31 | <LLOQ | 4.76 | <LLOQ | <LLOQ |
| GA 100 mM | 307.11 | <LLOQ | 15.87 | <LLOQ | <LLOQ |
| GA 10 mM | 45.29 | <LLOQ | 6.42 | <LLOQ | <LLOQ |
| GA 1 mM | 34.31 | <LLOQ | 5.08 | <LLOQ | <LLOQ |
| MH 100 mM | 80.51 | 3.19 | 12.59 | 3.24 | <LLOQ |
| MH 10 mM | 28.7 | <LLOQ | 4.42 | <LLOQ | <LLOQ |
| MH 1 mM | 24.78 | <LLOQ | 3.83 | <LLOQ | <LLOQ |
| GMH 100 mM | 334.82 | 3.59 | 16.73 | <LLOQ | <LLOQ |
| GMH 10 mM | 48.42 | <LLOQ | 6.64 | <LLOQ | <LLOQ |
| GMH 1 mM | 32.51 | <LLOQ | 5.11 | <LLOQ | <LLOQ |
| | | Donor 2 | | | |
| RPMI Alone | 35.1 | <LLOQ | 3.31 | <LLOQ | <LLOQ |
| DMSO | 29.59 | <LLOQ | 2.99 | <LLOQ | 2.95 |
| Myr 100 mM | 48.77 | <LLOQ | 3.91 | <LLOQ | <LLOQ |
| Myr 10 mM | 25.65 | <LLOQ | 2.93 | <LLOQ | <LLOQ |
| Myr 1 mM | 33.06 | <LLOQ | 3.39 | <LLOQ | <LLOQ |
| HES 100 mM | 92.66 | 70.17 | 54.28 | <LLOQ | <LLOQ |
| HES 10 mM | 39.01 | <LLOQ | 3.59 | <LLOQ | <LLOQ |
| HES 1 mM | 37.48 | <LLOQ | 3.56 | <LLOQ | <LLOQ |
| GA 100 mM | 109.71 | <LLOQ | 3.96 | <LLOQ | <LLOQ |

TABLE 16-continued

Cytokine Levels in Supernatant Following 26-Hour Treatment

| Treatment | TNF-α | IL-1β | IL-6 | IL-2 | IFN-g |
|---|---|---|---|---|---|
| GA 10 mM | 51.99 | <LLOQ | 4.29 | <LLOQ | <LLOQ |
| GA 1 mM | 40.27 | <LLOQ | 3.62 | <LLOQ | <LLOQ |
| MH 100 mM | 56.61 | 3.36 | 4.66 | <LLOQ | <LLOQ |
| MH 10 mM | 20.15 | <LLOQ | 2.58 | <LLOQ | <LLOQ |
| MH 1 mM | 24.97 | <LLOQ | 2.91 | <LLOQ | <LLOQ |
| GMH 100 mM | 90.19 | <LLOQ | 3.67 | <LLOQ | 3.03 |
| GMH 10 mM | 36.61 | <LLOQ | 3.73 | <LLOQ | <LLOQ |
| GMH 1 mM | 25.36 | <LLOQ | 2.98 | <LLOQ | <LLOQ |
| | | Donor 3 | | | |
| RPMI Alone | 11.47 | <LLOQ | 2.36 | <LLOQ | <LLOQ |
| DMSO | 11.76 | <LLOQ | 2.21 | <LLOQ | <LLOQ |
| Myr 100 mM | 17.16 | <LLOQ | 2.31 | <LLOQ | <LLOQ |
| Myr 10 mM | 11.87 | <LLOQ | 2.13 | <LLOQ | <LLOQ |
| Myr 1 mM | 11.8 | <LLOQ | 1.8 | <LLOQ | <LLOQ |
| HES 100 mM | 960.39 | 1975.6 | 1184.51 | <LLOQ | 6.33 |
| HES 10 mM | 13.92 | <LLOQ | 2.35 | <LLOQ | <LLOQ |
| HES 1 mM | 15.78 | <LLOQ | 2.33 | <LLOQ | <LLOQ |
| GA 100 mM | 90.93 | <LLOQ | 3.09 | <LLOQ | <LLOQ |
| GA 10 mM | 17.51 | <LLOQ | 2.07 | <LLOQ | <LLOQ |
| GA 1 mM | 11.63 | <LLOQ | 1.8 | <LLOQ | <LLOQ |
| MH 100 mM | 27.75 | 2.57 | 3.21 | <LLOQ | <LLOQ |
| MH 10 mM | 11.37 | <LLOQ | 1.9 | <LLOQ | <LLOQ |
| MH 1 mM | 11.2 | <LLOQ | 1.81 | <LLOQ | <LLOQ |
| GMH 100 mM | 122.71 | <LLOQ | 3.93 | <LLOQ | <LLOQ |
| GMH 10 mM | 28.74 | <LLOQ | 7.22 | <LLOQ | <LLOQ |
| GMH 1 mM | 15.03 | <LLOQ | 2.63 | <LLOQ | <LLOQ |

IL-1β LLOQ = 2.512 pg/mL, IL-2 LLOQ = 2.269 pg/mL, IFN-g LLOQ = 3.023 pg/mL

TABLE 17

Cytokine Levels in Supernatant Following 8-Hour 1 ng/mL LPS Stimulation

| Treatment | TNF-α | IL-1β | IL-6 | IL-2 | IFN-g |
|---|---|---|---|---|---|
| | | Donor 1 | | | |
| RPMI Alone[a] | <LLOQ | <LLOQ | <LLOQ | <LLOQ | <LLOQ |
| DMSO Alone[a] | <LLOQ | <LLOQ | <LLOQ | <LLOQ | <LLOQ |
| LPS Alone | 1417.82 | 2362.87 | 863.49 | <LLOQ | <LLOQ |
| Myr 200 mM | 1811.82 | 2923.92 | 781.22 | <LLOQ | <LLOQ |
| Myr 100 mM | 1251.59 | 2858.12 | 767.01 | <LLOQ | <LLOQ |
| Myr 10 mM | 1496.9 | 3079.47 | 884.11 | <LLOQ | <LLOQ |
| HES 200 mM | 2290.76 | 4853.62 | 1485.45 | <LLOQ | <LLOQ |
| HES 100 mM | 2577.7 | 3955.41 | 1441.95 | <LLOQ | <LLOQ |
| HES 10 mM | 1889.91 | 3059.18 | 1099.07 | <LLOQ | <LLOQ |
| GA 200 mM | 1973.87 | 905.16 | 466.09 | <LLOQ | <LLOQ |
| GA 100 mM | 2673.83 | 2029.63 | 776.23 | <LLOQ | <LLOQ |
| GA 10 mM | 2295.37 | 4009.57 | 1244.44 | <LLOQ | <LLOQ |
| MH 200 mM | 2127.76 | 4448.24 | 1059.64 | <LLOQ | <LLOQ |
| MH 100 mM | 1758.6 | 2617.61 | 805.01 | <LLOQ | <LLOQ |
| MH 10 mM | 1617.53 | 2849.44 | 1098.42 | <LLOQ | <LLOQ |
| GMH 200 mM | 2402.6 | 1512.58 | 581.33 | <LLOQ | <LLOQ |
| GMH 100 mM | 2568.75 | 2382.65 | 686.4 | <LLOQ | <LLOQ |
| GMH 10 mM | 1584.04 | 3224.72 | 744.9 | <LLOQ | <LLOQ |
| | | Donor 2 | | | |
| RPMI Alone[a] | <LLOQ | <LLOQ | <LLOQ | <LLOQ | <LLOQ |
| DMSO Alone[a] | <LLOQ | <LLOQ | <LLOQ | <LLOQ | <LLOQ |
| LPS Alone | 1375.72 | 2485.92 | 760.26 | <LLOQ | <LLOQ |
| Myr 200 mM | 1021.2 | 2501.45 | 649.98 | <LLOQ | <LLOQ |
| Myr 100 mM | 1597.26 | 3046.49 | 833.84 | <LLOQ | <LLOQ |
| Myr 10 mM | 1006.28 | 2517.48 | 685.49 | <LLOQ | <LLOQ |
| HES 200 mM | 1621.58 | 3244.42 | 1082.76 | <LLOQ | <LLOQ |
| HES 100 mM | 1254.84 | 2344.12 | 851.1 | <LLOQ | <LLOQ |
| HES 10 mM | 1091.56 | 2855.56 | 884.11 | <LLOQ | <LLOQ |
| GA 200 HIM | 1867.55 | 858.76 | 426.3 | <LLOQ | <LLOQ |
| GA 100 mM | 2001.65 | 1867.42 | 694.6 | <LLOQ | <LLOQ |

TABLE 17-continued

Cytokine Levels in Supernatant Following 8-Hour 1 ng/mL LPS Stimulation

| | Concentration (pg/mL) | | | | |
|---|---|---|---|---|---|
| Treatment | TNF-α | IL-1β | IL-6 | IL-2 | IFN-g |
| GA 10 mM | 924.89 | 2259.03 | 547.26 | <LLOQ | <LLOQ |
| MH 200 mM | 1151.85 | 2640.26 | 577.16 | <LLOQ | <LLOQ |
| MH 100 mM | 962.33 | 2367.56 | 456.09 | <LLOQ | <LLOQ |
| MH 10 mM | 1157.39 | 1934.62 | 651.89 | <LLOQ | <LLOQ |
| GMH 200 mM | 1132.96 | 564.16 | 169.1 | <LLOQ | <LLOQ |
| GMH 100 mM | 1648.38 | 1692.36 | 602.72 | <LLOQ | <LLOQ |
| GMH 10 mM | 2279.17 | 3951.71 | 1055.9 | <LLOQ | <LLOQ |
| | Donor 3 | | | | |
| RPMI Alone[a] | <LLOQ | <LLOQ | <LLOQ | <LLOQ | <LLOQ |
| DMSO Alone[a] | <LLOQ | <LLOQ | <LLOQ | <LLOQ | <LLOQ |
| LPS Alone | 4449.11 | 3881.34 | 760.26 | <LLOQ | <LLOQ |
| Myr 200 mM | 2528.98 | 2756.81 | 649.98 | <LLOQ | <LLOQ |
| Myr 100 mM | 3225.93 | 3293.89 | 833.84 | <LLOQ | <LLOQ |
| Myr 10 mM | 4121.89 | 3880.95 | 685.49 | <LLOQ | <LLOQ |
| HES 200 mM | 2731.72 | 4883.06 | 1082.76 | <LLOQ | <LLOQ |
| HES 100 mM | 3808.52 | 4941.84 | 851.1 | <LLOQ | <LLOQ |
| HES 10 mM | 3632.86 | 3800.6 | 884.11 | <LLOQ | <LLOQ |
| GA 200 mM | 4121.3 | 1478.91 | 426.3 | <LLOQ | <LLOQ |
| GA 100 mM | 3070.21 | 1788.4 | 694.6 | <LLOQ | <LLOQ |
| GA 10 mM | 4990.73 | 4065.13 | 547.26 | <LLOQ | <LLOQ |
| MH 200 mM | 4817.57 | 5495.71 | 577.16 | <LLOQ | <LLOQ |
| MH 100 mM | 4147.04 | 4837.22 | 456.09 | <LLOQ | <LLOQ |
| MH 10 mM | 3546.84 | 3678.65 | 651.89 | <LLOQ | <LLOQ |
| GMH 200 mM | 2912.31 | 1514.26 | 169.1 | <LLOQ | <LLOQ |
| GMH 100 mM | 3303.86 | 2432.53 | 760.26 | <LLOQ | <LLOQ |
| GMH 10 mM | 3901.11 | 3929.84 | 649.98 | <LLOQ | <LLOQ |

TNF-α LLOQ = 2.018 pg/mL, IL-1β LLOQ = 2.299 pg/mL, IL-6 LLOQ = 0.831, IL-2 LLOQ = 1.698 pg/mL, IFN-g LLOQ = 2.792 pg/mL
[a]Samples were not stimulated with LPS No significant production of IFN-g or IL-2 was detected with any treatments or donors.

Except for the two negative control conditions, all 3 donors responded to all experimental conditions tested with the secretion of TNF-α, IL-1β, and IL-6 albeit with a high degree of variability. Any changes greater than 1.5 fold was considered significant if it was observed in at least 2 out of 3 donors.

Gallic Acid showed an inhibition of LPS stimulated production of IL-1β and IL-6, when used alone or in combination with hesperidin at a concentration of 200 mM. On the other hand, hesperidin, when used alone or in combination with myricetin at 200 μM, appeared to enhance the secretion of IL-1. Interestingly, when hesperidin was used in combination with gallic acid at 200 μM, gallic acid appeared to override the enhancement observed by hesperidin as the suppression of LPS induced IL1-β and IL-6 was maintained.

TABLE 18

Fold-change in cytokine
production relative to LPS treatment alone.

| | Mean Fold-Change (Relative to LPS alone) | | |
|---|---|---|---|
| Treatment | TNF-α | IL-1β | IL-6 |
| Myr 200 mM | 0.86 | 0.98 | 0.75 |
| Myr 100 mM | 0.93 | 1.09 | 0.88 |
| Myr 10 mM | 0.90 | 1.10 | 0.97 |
| HES 200 mM | 1.14 | 1.54 | 1.25 |
| HES 100 mM | 1.20 | 1.30 | 1.24 |
| HES 10 mM | 0.98 | 1.14 | 1.10 |
| GA 200 mM | 1.23 | 0.37 | 0.58 |

TABLE 18-continued

Fold-change in cytokine
production relative to LPS treatment alone.

| | Mean Fold-Change (Relative to LPS alone) | | |
|---|---|---|---|
| Treatment | TNF-α | IL-1β | IL-6 |
| GA 100 mM | 1.34 | 0.69 | 0.75 |
| GA 10 mM | 1.14 | 1.22 | 1.11 |
| MH 200 mM | 1.15 | 1.45 | 0.97 |
| MH 100 mM | 0.96 | 1.10 | 0.83 |
| MH 10 mM | 0.93 | 0.98 | 0.97 |
| GMH 200 mM | 1.06 | 0.42 | 0.41 |
| GMH 100 mM | 1.26 | 0.77 | 0.69 |
| GMH 10 mM | 1.63 | 1.32 | 0.98 |

Note:
All conditions include 1 ng/mL LPS stimulation for 8 hours.

Myricetin did not appear to have any effect on LPS stimulated cytokine secretion under any conditions tested.

CONCLUSIONS

Based on our experimental design, these results suggest that 1) hesperidin by itself can potentiate the effect of LPS stimulation on IL-1β production, 2) gallic acid inhibits LPS induced secretion of IL-1β and IL-6 and 3) myricetin has no effect on LPS induced secretion of the cytokines tested.

The inhibitory effect of gallic acid, alone and combined with myricetin and hesperidin, is in line with previous studies demonstrating the anti-inflammatory effect of this molecule. Furthermore, based on the inhibition observed, it appears that the effect may be due entirely to the presence of gallic acid as no noticeable inhibition is observed with either myricetin or hesperidin.

It should be noted that the effects described herein were all observed at test compound concentrations of 200 mM which were not tested during Phase 1. Therefore, the effect of the compounds alone on cytokine production cannot be evaluated at the highest dose tested. Moreover, due to the combination of different donors used, the small sample size and the overall inter-donor variability the data interpretation was limited.

The invention claimed is:

1. A method limiting the occurrence of or treating viral infections comprising administering a composition comprising therapeutically effective amounts of (i) myricetin, (ii) inhibitor, and (iii) gallic acid, to a patient at risk of or diagnosed with a viral infection, to thereby limit the occurrence of or treating the viral infection by mitigating a cytokine response associate with the viral infection.

2. A composition for treating viral infections comprising therapeutically effective amounts of myricetin, hesperidin and gallic acid, wherein, when the composition is administered to an individual in need of treatment therefrom, the composition limits the occurrence of or treats the viral infection, by mitigating a cytokine response in the individual, associated with the viral infection.

3. The composition of claim 2, wherein about 40 to about 75% weight myricetin; about 30 to about 50% hesperidin and 5 to about 30% gallic acid, based on the total weight of the mixture, are present in the composition.

4. The composition of claim 1, wherein the composition comprises 400 mg myricetin, 300 mg hesperidin and 300 mg gallic acid.

5. The composition of claim 1, wherein a weight ratio of myricetin to hesperidin to gallic acid is 4:3:3.

6. A method limiting the occurrence of or treating a viral infection in a human comprising administering a composition comprising 40% myricetin, 30% hesperidin, and 30% gallic acid, based on the total weight of the mixture, to a human at risk of or diagnosed with the viral infection.

7. A method limiting the occurrence of or treating a viral infection in a human comprising administering a composition comprising 50% myricetin, 40% hesperidin, and 10% gallic acid, based on the total weight of the composition, to a human at risk of or diagnosed with the viral infection.

8. A method of limiting the occurrence or treating a virus infection in a human comprising administering a composition comprising myricetin, hesperidin, and gallic acid in a ratio of 4:3:3 based on the total weight of the mixture, to a human at risk of or diagnosed with the viral infection.

* * * * *